(12) United States Patent
King-Underwood et al.

(10) Patent No.: US 9,321,773 B2
(45) Date of Patent: *Apr. 26, 2016

(54) COMPOUNDS

(71) Applicant: Respivert Ltd, Buckinghamshire (GB)

(72) Inventors: John King-Underwood, Pendock (GB); Kazuhiro Ito, London (GB); Peter John Murray, London (GB); George Hardy, Robertsbridge (GB); Frederick Arthur Brookfield, Abingdon (GB); Christopher John Brown, Abingdon (GB)

(73) Assignee: Respivert, Ltd., Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/220,650

(22) Filed: Mar. 20, 2014

(65) Prior Publication Data

US 2014/0249164 A1 Sep. 4, 2014

Related U.S. Application Data

(63) Continuation of application No. 13/502,465, filed as application No. PCT/EP2010/065746 on Oct. 19, 2010, now Pat. No. 8,741,909.

(30) Foreign Application Priority Data

Oct. 19, 2009 (GB) .................................. 0918249.4

(51) Int. Cl.
C07D 487/04 (2006.01)

(52) U.S. Cl.
CPC .................... C07D 487/04 (2013.01)

(58) Field of Classification Search
CPC .................................................. C07D 487/04
See application file for complete search history.

(56) References Cited

U.S. PATENT DOCUMENTS

| 7,186,401 B2 | 3/2007 | Keller et al. | |
|---|---|---|---|
| 2006/0239932 A1 | 10/2006 | Monteith et al. | |
| 2007/0037805 A1 | 2/2007 | Hayakawa et al. | |
| 2011/0135655 A1* | 6/2011 | Katsikis et al. ............ | 424/158.1 |
| 2012/0082727 A1 | 4/2012 | Cocconi et al. | |
| 2013/0231355 A1* | 9/2013 | King-Underwood et al. .......................... | 514/262.1 |

FOREIGN PATENT DOCUMENTS

| CA | 2347856 | | 5/2000 |
|---|---|---|---|
| EP | 1232745 | A1 | 8/2002 |
| EP | 1277738 | | 1/2003 |
| EP | 1604981 | | 12/2005 |
| EP | 1661879 | | 5/2006 |
| EP | 1790637 | | 5/2007 |
| EP | 1829533 | A2 | 9/2007 |
| EP | 2311434 | A1 | 4/2011 |
| WO | | 87/05213 A1 | 9/1987 |
| WO | | 00/28979 A1 | 5/2000 |
| WO | WO 00/42042 | | 7/2000 |
| WO | | 00/53157 A1 | 9/2000 |
| WO | WO 01/81346 | | 11/2001 |
| WO | WO 01/83456 | | 11/2001 |
| WO | WO 02/051831 | | 7/2002 |
| WO | WO 03/006628 | | 1/2003 |
| WO | WO 03/007955 | | 1/2003 |
| WO | WO 03/035075 | | 5/2003 |
| WO | WO 2004/037176 | | 5/2004 |
| WO | WO 2004/080966 | | 9/2004 |
| WO | WO 2004/083174 | | 9/2004 |

(Continued)

OTHER PUBLICATIONS

Knight et al., "A Pharmacological Map of the PI-K Family Defines a Role for p100α in Insulin Signaling" Cell, vol. 125, 2006, pp. 733-747.
Aspel et al., "Targeted polypharmacology:discovery of dual inhibitors of tyrosine and phosphoinositide kinases", Nature Chemical Biology, vol. 4, 2008, pp. 691-699.
Laplante, et al., "Assessing Atropisomer Axial Chemistry Chirality in Drug Discovery and Development", Journal of Medicinal Chemistry, 2011; vol. 54, pp. 7005-7011.
Clayden, et al., "The Challenge of Atropisomerism in Drug Discovery", Angew. Chem. Int. Ed. 2009; vol. 48, pp. 6398-6401.
Brana et al., "Clinical development of phosphatidylinositol 3-kinase inhibitors for cancer treatment", BMC Medicine, 2012; vol. 10: 161, pp. 1-15.

(Continued)

*Primary Examiner* — Rebecca Anderson
*Assistant Examiner* — Karen Cheng
(74) *Attorney, Agent, or Firm* — Bradley E. Davis

(57) ABSTRACT

The present invention relates to compounds of formula (I)

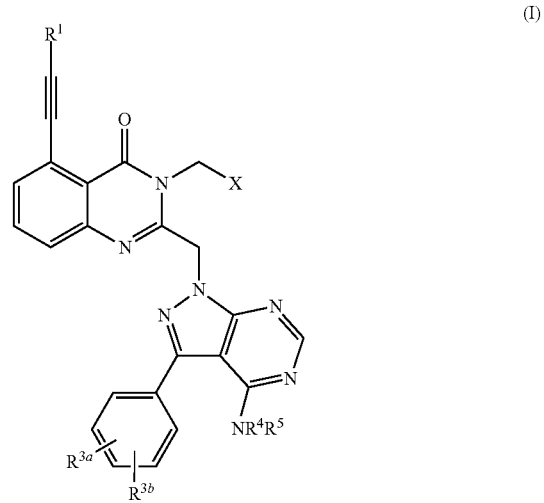

and to compositions comprising the same and to the use of the compounds and their compositions in treatment, for example in the treatment of inflammatory diseases, in particular respiratory inflammatory disease. The invention also extends to methods of making said compounds.

1 Claim, 5 Drawing Sheets

(56) References Cited

FOREIGN PATENT DOCUMENTS

| | | |
|---|---|---|
| WO | WO 2005/007085 | 1/2005 |
| WO | WO 2005/012221 | 2/2005 |
| WO | WO 2005/016348 | 2/2005 |
| WO | WO 2005/016349 | 2/2005 |
| WO | 2005/046636 A1 | 5/2005 |
| WO | WO 2005/067901 | 7/2005 |
| WO | WO 2005/112935 | 12/2005 |
| WO | WO 2005/113554 | 12/2005 |
| WO | WO 2005/113556 | 12/2005 |
| WO | WO 2005/117889 | 12/2005 |
| WO | WO 2005/120511 | 12/2005 |
| WO | WO 2006/030925 | 3/2006 |
| WO | WO 2006/089106 | 8/2006 |
| WO | 2007/068443 A1 | 6/2007 |
| WO | WO 2007/114926 | 10/2007 |
| WO | WO 2008/005262 | 1/2008 |
| WO | 2008/058691 A2 | 5/2008 |
| WO | WO 2008/058402 | 5/2008 |
| WO | WO 2008/067219 | 6/2008 |
| WO | WO 2008/104077 | 9/2008 |
| WO | WO 2008/127226 | 10/2008 |
| WO | WO 2008/138834 | 11/2008 |
| WO | WO 2008/140750 | 11/2008 |
| WO | WO 2009/088986 | 7/2009 |
| WO | WO 2009/088990 | 7/2009 |
| WO | WO 2010/036380 | 4/2010 |
| WO | WO 2010/059593 | 5/2010 |
| WO | WO 2010/065923 | 6/2010 |
| WO | WO 2010/065932 | 6/2010 |
| WO | WO 2010/111432 | 9/2010 |
| WO | WO 2011/015037 | 2/2011 |
| WO | 2011/048111 A1 | 4/2011 |
| WO | WO 2012/052753 | 4/2012 |
| WO | WO 2013/136075 | 9/2013 |
| WO | WO 2013/136076 | 9/2013 |

OTHER PUBLICATIONS

Thomas et al., "Inhibition of PI-3 kinase for treating respiratory disease: good idea or bad idea?", Current Opinion in Pharmacology, 2008; vol. 8, pp. 267-274.

Ramen, L. E. and Cantley, L. C. "The Role of Phosphoinositide 3-Kinase Lipid Products in Cell Function", J. Biol. Chem., 1999, 274:8347-8350.

Ito, K. et al., "Therapeutic Potential of Phosphatidylinositol 3-Kinase Inhibitors in Inflammatory Respiratory Disease", J Pharmacol. Exp. Ther., 2007, 321:1-8.

Lee, K. S. et al., "Phosphoinositide 3-kinase- σ inhibitor recudes vascular permeability in a murine model of asthma", J. Allergy Clin. Immunol., 2006, 118:403-409.

Lee, K. S. et al.,"Inhibition of phosphoinositide σ attenuates allergic airway inflammation and hyperresponsiveness in murine asthma model", 3-kinase FASEB J., 2006, 20:455-65.

Sadhu, .et al., "Selective role of PI3K σ in neutrophil inflammatory responses", Biochem. Biophys. Res. Commun., 2003, 308:764-9.

Doukas, J. et al., "Aerosolized Phosphoinositide 3-Kinase γ σ Inhibitor TG100-115 {3-{2,4-Diamino-6-(3- hydroxyphenyl)pteridin-7-yl}phenol} as a Therapeutic Candidate for Asthma and Chronic Obstructive Pulmonary Disease" , J Pharmacol. Exp. Ther., 2009, 328:758-765.

To, Y. et al., "Targeting Phosphoinositide-3-Kinase-σ with Theophylline Reserves Corticosteriod Insensitivity in Chronic Obstructive Polmonary Disease", Am. J. Respir. Crit. Care Med., 2010, 182:897-904.

Gautier et al., "Contribution à l'étude des ethers-0xydes propargyliques", Annales Pharmaceutigues Francaises, 1971, 29, 39-50.

Medicherla, S. et al., "p38α-Selective Mitogen-Activated Protein Kinase Inhibitor Sd-282 Reduces Inflammation in a Subchronic Model of Tobacco smole-Induced Airway Inflammation", J. Pharamcol. Exp. Ther 2009, 342: 921-9.

Brittain, H.G., Polymorphism in Pharmaceutical Solids (Second Edition), 2009, vol. 192; ISBN:9781420073 1218/1420073214; pp. 1-5; 14-19; 88-95; 120-121; 234-237; 240-241; 318-346; 347-380 and 381-430.

Jordan, V.C., "Tamoxifen:A Most Unlikely Pioneering Medicine", Nature Reviews; Drug Discovery, 2, 2003, p. 2005.

Hackman, et al., "Translation of Research Evidence From Animals to Humans", JAMA, 296(14), 2006, pp. 1731-1732.

Shah et al, "Evaluation of Two New Tablet Lubricants—Sodium Stearyl Fumarate and Glyceryl Behenate. Measurement of Physical Parameters (Compaction, Ejection and Residual Forces) in the Tableting Process and the Effect on the Dissolution Rate", Drug development and Industrial pharmacy 1986, vol. 12 No. 8-9, pp. 1329-1346.

* cited by examiner

Figure 1: Chiral Stationary Phase HPLC Analysis of PIK294:
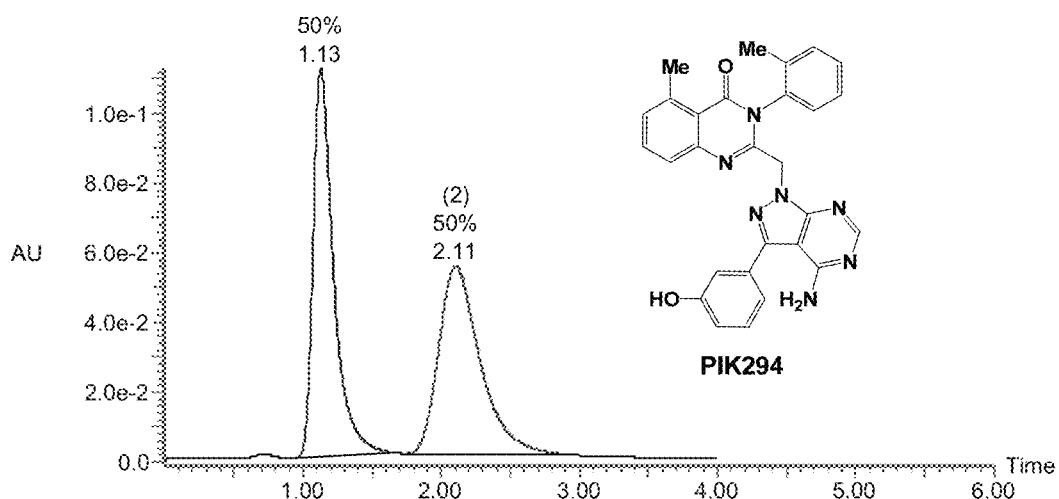
Conditions: Chiralpak AD-H eluting with 70:30 Heptane:IPA, UV detection at 254 nm.

Figure 2: Preparative Chiral HPLC Separation of the Atropisomers of PIK294
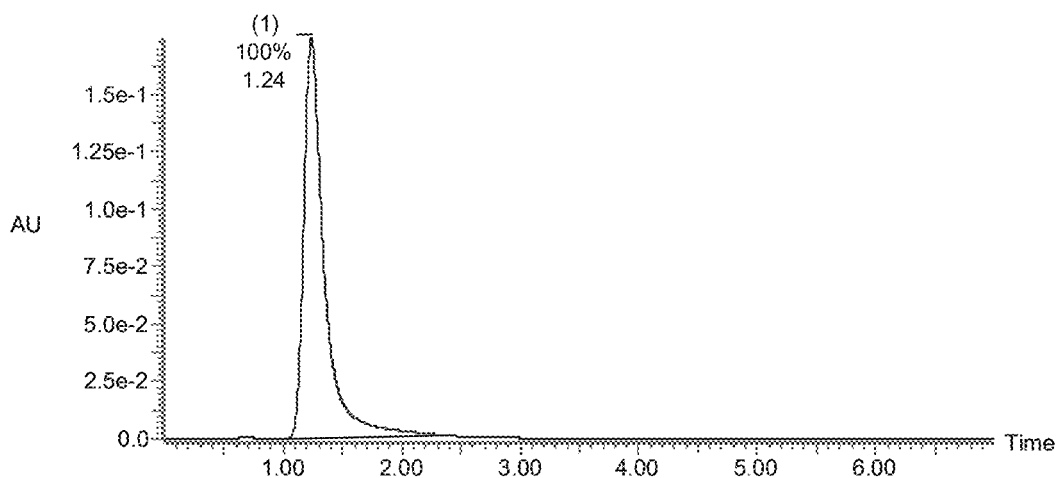
Conditions: Chiralpak AD-H column, 70:30 heptane:IPA: Isomer 1: $R^t$ =1.24 min.
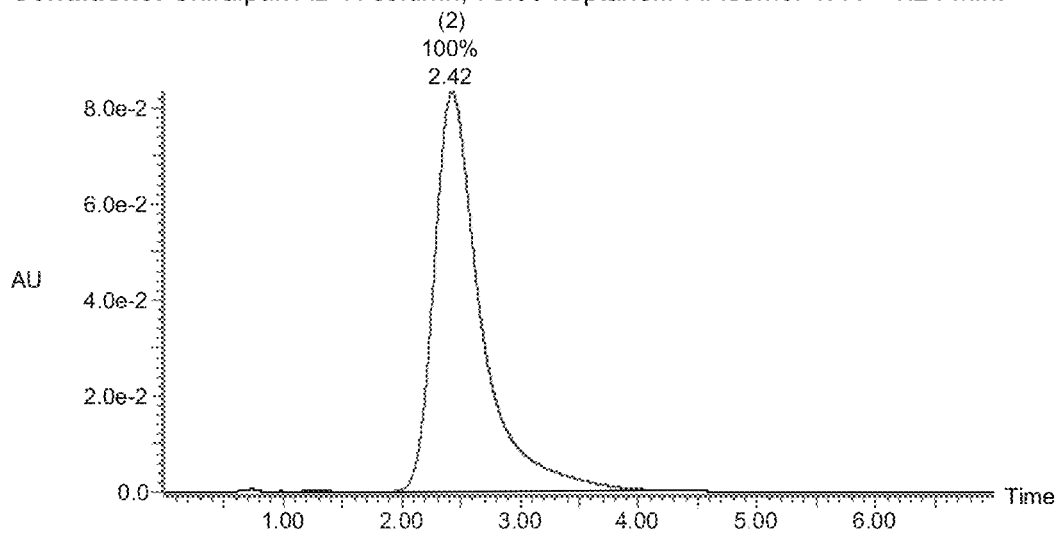
Conditions: Chiralpak AD-H column, 70:30 heptane:IPA: Isomer 2: $R^t$ =2.42 min;.

Figure 3: N-3 Aryl Quinazolinones Separated into Atropisomers by Chiral HPLC
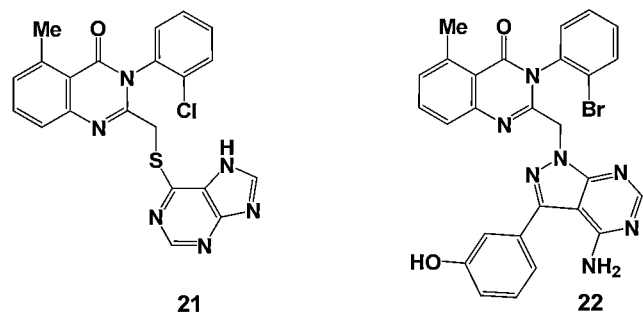

Figure 4: Inhibition of LPS-induced neutrophilia in the mouse by the compound of Example 1
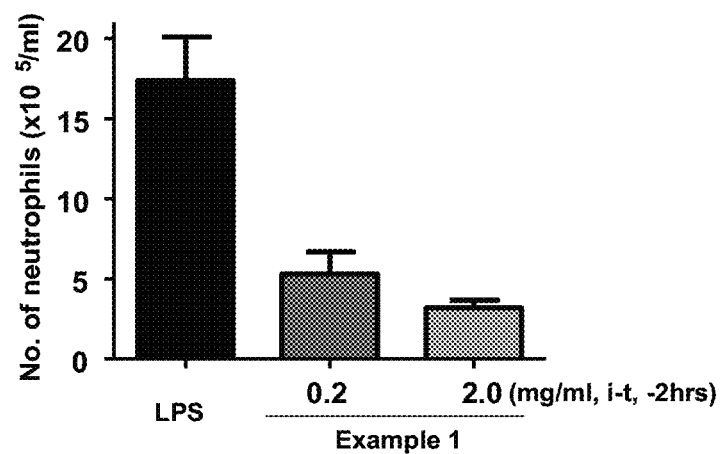
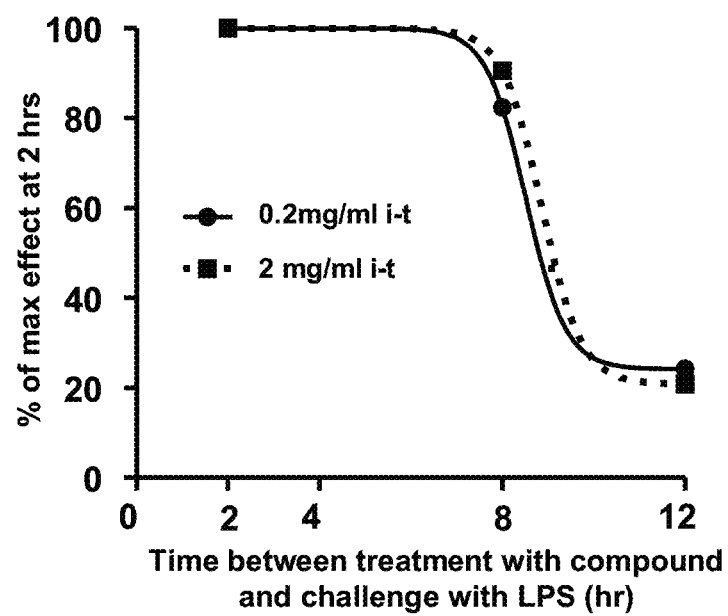

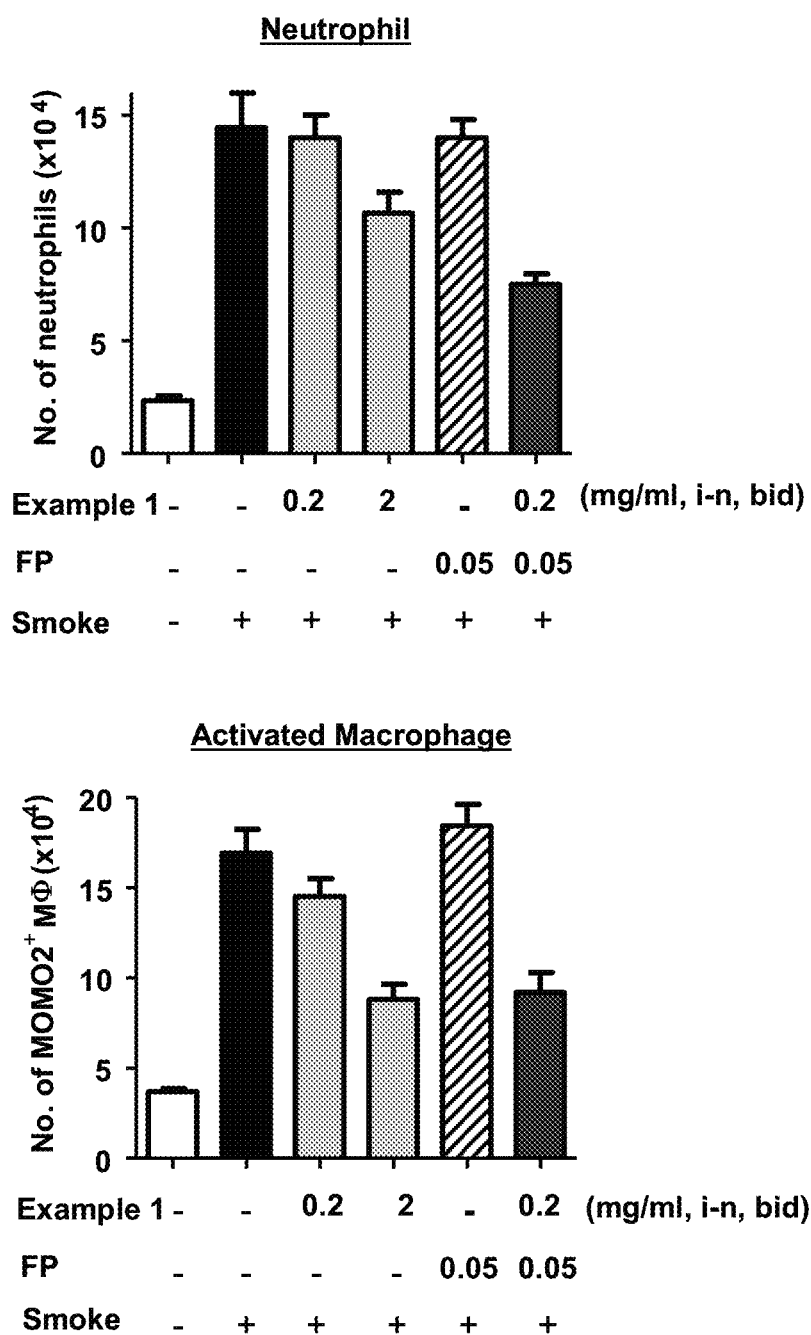
Figure 5: Inhibition by the compound of Example 1 of cigarette smoke-induced pulmonary macrophage and neutrophil influx in the mouse

COMPOUNDS

This application is a continuation of U.S. Ser. No. 13/502,465, filed on Apr. 17, 2012, which is a National Stage application under 35 U.S.C. 371 of PCT International Application No. PCT/EP2010/065746, filed Oct. 19, 2010, which claims priority from Great Britain patent application number GB 0918249.4, filed Oct. 19, 2009, the contents of which are hereby incorporated by reference in their entirety.

FIELD OF THE INVENTION

The invention relates to compounds which are inhibitors of phosphoinositide 3-kinases, (PI3 kinases). In particular the invention relates to compounds that inhibit the PI3 kinase delta sub-type and optionally, in addition, the gamma and alpha sub-types thereof, and their use in therapy, including in pharmaceutical combinations, especially in the treatment of inflammatory diseases, including inflammatory diseases of the lung, such as COPD and asthma. The disclosure also extends to methods of preparing said compounds and pharmaceutical compositions comprising same.

BACKGROUND OF THE INVENTION

Lipid kinases catalyse the phosphorylation of lipids to produce species involved in the regulation of a wide range of physiological processes, including cellular migration and adhesion. The PI3-kinases belong to this class of enzymes and are membrane associated proteins which catalyse the phosphorylation of lipids which are themselves associated with cell membranes. The PI3-kinase delta (δ) isozyme (PI3 kinase δ) is one of four isoforms of type I PI3 kinases responsible for generating various 3'-phosphorylated phosphoinositides, that mediate cellular signalling and have been implicated in a number of cellular processes such as inflammation, growth factor signalling, malignant transformation and immunity (See Review by Rameh, L. E. and Cantley, L. C. *J. Biol. Chem.*, 1999, 274:8347-8350).

Involvement of PI3 kinases in controlling inflammation has been confirmed in several models using pan-PI3 kinase inhibitors, such as LY-294002 and wortmannin (Ito, K. et al., *J Pharmacol. Exp. Ther.*, 2007, 321:1-8). Recent studies have been conducted using either selective PI3 kinase inhibitors or in knock-out mice lacking a specific enzyme isoform. These studies have demonstrated the role of the pathways controlled by PI3 kinase enzymes in inflammation. The PI3 kinase δ selective inhibitor IC-87114 was found to inhibit airway hyper-responsiveness, IgE release, pro-inflammatory cytokine expression, inflammatory cell accumulation into the lung and vascular permeability in ovalbumin-sensitized, ovalbumin-challenged mice [Lee, K. S. et al., *J. Allergy Clin. Immunol.*, 2006, 118:403-409 and Lee, K. S. et al., *FASEB J.*, 2006, 20:455-65]. In addition, IC-87114 lowered neutrophil accumulation in the lungs of mice and neutrophil function, stimulated by TNFα [Sadhu, C. et al., *Biochem. Biophys. Res. Commun.*, 2003, 308:764-9]. The PI3 kinase δ isoform is activated by insulin and other growth factors, as well as G-protein coupled protein signaling and inflammatory cytokines. Recently the PI3 kinase dual δ/γ inhibitor TG100-115 was reported to inhibit pulmonary eosinophilia, interleukin-13 as well as mucin accumulation and airways hyperesponsiveness in a murine model, when administered by aerosolisation. The same authors also reported that the compound was able to inhibit pulmonary neutrophilia elicited by either LPS or cigarette smoke [Doukas, J. et al., *J. Pharmacol. Exp. Ther.*, 2009, 328:758-765]

Since it is also activated by oxidative stress, the PI3 kinase δ isoform is likely to be relevant as a target for therapeutic intervention in those diseases where a high level of oxidative stress is implicated. Downstream mediators of the PI3 kinase signal transduction pathway include Akt (a serine/threonine protein kinase) and the mammalian target of rapamycin, the enzyme mTOR. Recent work has suggested that activation of PI3 kinase δ, leading to phosphorylation of Akt, is able to induce a state of corticosteroid resistance in otherwise corticosteroid-sensitive cells [To, Y. et al., *Am. J. Respir. Crit. Care Med.*, 2010, 182:897-904]. These observations have led to the hypothesis that this signalling cascade could be one mechanism responsible for the corticosteroid-insensitivity of inflammation observed in the lungs of patients suffering from COPD, as well as those asthmatics who smoke, thereby subjecting their lungs to increased oxidative stress. Indeed, theophylline, a compound used in the treatment of both COPD and asthma, has been suggested to reverse steroid insensitivity through mechanisms involving interaction with pathways controlled by PI3 kinase δ [To, Y. et al., *Am. J. Respir. Crit. Care Med.*, 2010, 182:897-904].

At present the mainstay of treatment for both asthma and COPD is inhaled therapy, using a combination of corticosteroids, muscarinic antagonists and $\beta_2$-agonists, as judged clinically appropriate. One way of addressing the unmet medical needs in COPD and asthma is to identify new therapeutic agents, for example suitable for use as inhaled medicines, which have the potential to provide significant benefit when used as a monotherapy or in combination with one or more medicaments from these three pharmacological classes. Therefore, there remains a need to identify and develop isoform selective PI3 kinase inhibitors which have the potential to provide enhanced therapeutic efficacy in asthma, COPD and other inflammatory diseases.

SUMMARY OF THE INVENTION

According to the invention, there is provided a compound of formula (I):

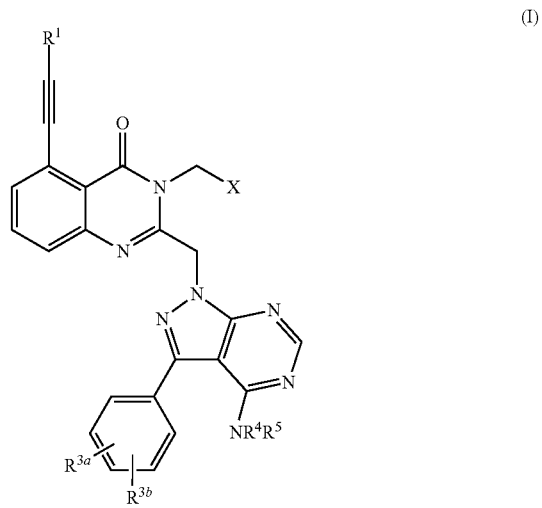

wherein
$R^1$ is H, a saturated or unsaturated, branched or unbranched $C_{1-15}$ alkyl chain, wherein optionally one or more carbons (for example 1, 2 or 3 carbons, suitably 1 or 2, in particular 1) is/are replaced by a heteroatom selected from O, N, S(O)$_p$, (for example a CH$_2$, group is replaced with O, or with NH, or with S, or with SO$_2$ or a —CH$_3$ group at the terminus of the chain or on a branch is replaced with OH or with NH$_2$) wherein said chain is optionally substituted by one or more groups (for example 1 to 3, such as 2 groups) independently selected from oxo, halogen, an aryl group, a heteroaryl group, a carbocyclyl group or a heterocyclyl group, each aryl, heteroaryl, carbocyclyl or heterocyclyl group bearing:
0 to 3 substituents selected from halogen, -hydroxyl, —C$_{1-6}$ alkyl, —C$_{1-6}$ alkoxy, —C$_{2-3}$ alkoxy-OC$_{1-3}$ alkyl, —C$_{2-3}$ alkylOC$_{1-3}$ alkyl, —C$_{1-3}$ hydroxyalkyl, —C$_{1-6}$ haloalkyl, amino, —C$_{1-4}$ mono or —C$_{2-8}$ di-alkyl amino, —C$_{1-4}$ mono or —C$_{2-8}$ di-acyl amino, —C$_{0-6}$ alkylS(O)$_p$C$_{1-6}$ alkyl, —C$_{0-6}$ alkylS(O)$_p$NR$^6$R$^7$, —C$_{0-6}$ alkylNR$^8$C$_{0-6}$alkylS(O)$_p$C$_{1-6}$ alkyl, —C$_{0-6}$ alkylC(O)OC$_{0-6}$ alkyl, —NR$^8$C$_{0-6}$ alkylC(O)NR$^6$R$^7$—NR$^8$C$_{0-6}$ alkylC(O)C$_{0-6}$ alkyl, —C$_{0-6}$ alkylC(O)NR$^6$R$^7$, and —C$_{0-6}$ alkylC(O)C$_{1-6}$ alkyl; and/or one aryl, heterocyclyl or carbocyclyl;

X is C$_{6-10}$ aryl or a C$_{5-9}$ heteroaryl each substituted by R$^{2a}$ and by R$^{2b}$ wherein R$^{2a}$ is selected from hydrogen, —C$_{1-3}$ alkyl, halo, hydroxyl, cyano, —C$_{1-3}$ haloalkyl, —C$_{1-3}$ alkoxy, —C$_{2-3}$ alkoxy-OC$_{1-3}$ alkyl, —C$_{2-3}$ alkylOC$_{1-3}$ alkyl, —C$_{1-3}$ hydroxyalkyl, —C$_{0-6}$ alkylS(O)$_q$C$_{1-3}$ alkyl, —C$_{0-6}$ alkylS(O)$_p$NR$^6$R$^7$, —C$_{0-6}$ alkylNR$^8$C$_{0-6}$alkylS(O)$_p$C$_{1-6}$ alkyl, —C$_{0-6}$ alkylC(O)OH, —C$_{0-6}$ alkylC(O)OC$_{1-6}$ alkyl, —NR$^8$C$_{0-6}$ alkylC(O)NR$^6$R$^7$, —NR$^8$C$_{0-6}$ alkylC(O)C$_{1-6}$ alkyl, —C$_{0-6}$ alkylC(O)NR$^6$R$^7$ and —C$_{0-6}$ alkylC(O)C$_{1-6}$ alkyl; and R$^{2b}$ is selected from hydrogen, C$_{1-3}$ alkyl, halo, hydroxyl, cyano, —C$_{1-3}$ haloalkyl, —C$_{1-3}$ alkoxy, and —C$_{0-6}$ alkylS(O)$_q$C$_{1-3}$ alkyl;

R$^{3a}$ is hydroxyl;

R$^{3b}$ is selected from hydrogen, hydroxyl, halo, cyano, —C$_{1-3}$ haloalkyl, —C$_{1-3}$ hydroxyalkyl, —C$_{1-3}$ alkoxy, and —S(O)$_q$C$_{1-3}$ alkyl;

R$^4$ is hydrogen or —C$_{1-3}$ alkyl;

R$^5$ is hydrogen or —C$_{1-3}$ alkyl;

R$^6$ is hydrogen or —C$_{1-6}$ alkyl;

R$^7$ is hydrogen or —C$_{1-6}$ alkyl;

R$^8$ is hydrogen or —C$_{1-6}$ alkyl;

p is 0 or an integer 1 or 2;

q is o or an integer 1 or 2 or a pharmaceutically acceptable salt thereof, including all stereoisomers, tautomers and isotopic derivatives thereof.

In one embodiment R$^1$ is H, a saturated or unsaturated, branched or unbranched C$_{1-12}$ alkyl chain, wherein optionally one or more carbons (for example 1, 2 or 3 carbons, suitably 1 or 2, in particular 1) is/are replaced by a heteroatom selected from O, N, S(O)$_p$, (for example a CH$_2$, group is replaced with O, or with NH, or with S, or with SO$_2$ or a —CH$_3$ group at the terminus of the chain or on a branch is replaced with OH or with NH$_2$) wherein said chain is optionally substituted by one or more groups (for example 1 to 3, such as 2 groups) independently selected from oxo, halogen, an aryl group, a heteroaryl group, a carbocyclyl group or a heterocyclyl group, each aryl, heteroaryl, carbocyclyl or heterocyclyl group bearing:
0 to 3 substituents selected from halogen, hydroxyl, —C$_{1-6}$ alkyl, —C$_{1-6}$ alkoxy, —C$_{2-3}$ alkylOC$_{1-3}$ alkyl, —C$_{2-3}$ alkoxy-OC$_{1-3}$ alkyl, —C$_{1-3}$ hydroxyalkyl, —C$_{1-6}$ haloalkyl, amino, —C$_{1-4}$ mono or —C$_{2-8}$ di-alkyl amino, —C$_{1-4}$ mono or —C$_{2-8}$ di-acyl amino, —C$_{0-6}$ alkylS(O)$_p$C$_{1-6}$ alkyl, —C$_{0-6}$ alkylS(O)$_p$NR$^6$R$^7$, —C$_{0-6}$ alkylNR$^8$C$_{0-6}$alkylS(O)$_p$C$_{1-6}$ alkyl, —C$_{0-6}$ alkylC(O)OC$_{0-6}$ alkyl, —NR$^8$C$_{0-6}$ alkylC(O)NR$^6$R$^7$—NR$^8$C$_{0-6}$ alkylC(O)C$_{0-6}$ alkyl, —C$_{0-6}$ alkylC(O)NR$^6$R$^7$, and —C$_{0-6}$ alkylC(O)C$_{1-6}$ alkyl; and/or one aryl, heterocyclyl or carbocyclyl.

BRIEF DESCRIPTION OF THE DRAWINGS

FIG. 1 shows chiral stationary phase HPLC analysis of PIK294

FIG. 2 shows preparative chiral HPLC separation of the atropisomers of PIK294

FIG. 3 shows N-3 aryl quinazolinones separated into atropisomers by chiral HPLC

FIG. 4 shows Inhibition of LPS-induced neutrophilia in the mouse by the compound of Example 1.

FIG. 5 shows inhibition by the compound of Example 1 of cigarette smoke-induced pulmonary macrophage and neutrophil influx in the mouse

DETAILED DESCRIPTION

In one embodiment there is provided a compound of formula (I)

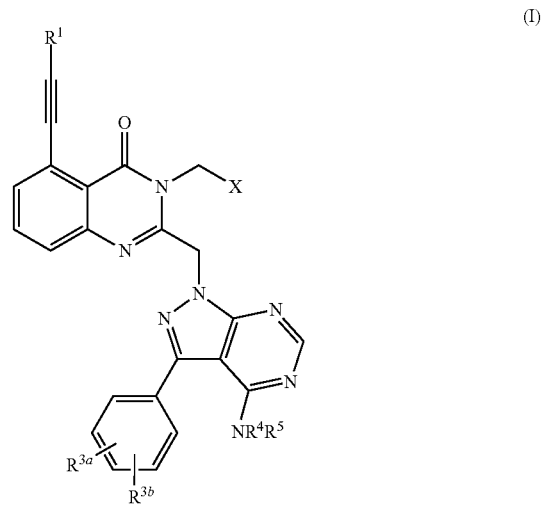

(I)

wherein

R$^1$ is H, a saturated or unsaturated, branched or unbranched C$_{1-10}$ alkyl chain, wherein optionally one or more carbons (for example 1, 2 or 3 carbons, suitably 1 or 2, in particular 1) is/are replaced by a heteroatom selected from O, N, S(O)$_p$, (for example a CH$_2$, group is replaced with O, or with NH, or with S, or with SO$_2$ or a —CH$_3$ group at the terminus of the chain or on a branch is replaced with OH or with NH$_2$) wherein said chain is optionally substituted by one or more groups (for example 1 to 3, such as 2 groups) independently selected from oxo, halogen, an aryl group, a heteroaryl group, a carbocyclyl group or a heterocyclyl group, each aryl, heteroaryl, carbocyclyl or heterocyclyl group bearing:
0 to 3 substituents selected from halogen, —C$_{1-6}$ alkyl, —C$_{1-6}$ alkoxy, —C$_{2-3}$ alkoxy-OC$_{1-3}$ alkyl, —C$_{1-6}$ haloalkyl, amino, —C$_{1-4}$ mono or —C$_{2-8}$ di-alkyl amino, —C$_{1-4}$ mono or —C$_{2-8}$ di-acyl amino, —C$_{0-6}$ alkylS(O)$_p$C$_{1-6}$ alkyl, —C$_{0-6}$ alkylS(O)$_p$NR$^6$R$^7$, —C$_{0-6}$ alkylNR$^8$C$_{0-6}$alkylS(O)$_p$C$_{1-6}$ alkyl, —C$_{0-6}$ alkylC(O)OC$_{0-6}$ alkyl, —NC$_{0-6}$ alkylC(O)NR$^6$R$^7$—NC$_{0-6}$ alkylC(O)C$_{0-6}$ alkyl, —C$_{0-6}$ alkylC(O)NR$^6$R$^7$, and —C$_{0-6}$ alkylC(O)C$_{1-6}$ alkyl; and/or one aryl, heterocyclyl or carbocyclyl;

X is C$_{6-10}$ aryl or a C$_{5-9}$ heteroaryl each substituted by R$^{2a}$ and optionally by R$^{2b}$
  wherein R$^{2a}$ is hydrogen, —C$_{1-3}$ alkyl, halo, hydroxyl, cyano, —C$_{1-3}$ haloalkyl, —C$_{1-3}$ alkoxy, —C$_{2-3}$ alkoxy-OC$_{1-3}$ alkyl, —C$_{1-3}$ hydroxyalkyl, —C$_{0-6}$ alkylS(O)$_q$ C$_{1-3}$ alkyl, —C$_{0-6}$ alkylS(O)$_p$NR$^6$R$^7$, —C$_{0-6}$ alkylNR$^8$C$_{0-6}$alkylS(O)$_p$C$_{1-6}$ alkyl, —C$_{0-6}$ alkylC(O)OH, —C$_{0-6}$ alkylC(O)OC$_{1-6}$ alkyl, —NC$_{0-6}$ alkylC(O)NR$^6$R$^7$, —NR$^8$C$_{0-6}$ alkylC(O)C$_{1-6}$ alkyl, —C$_{0-6}$ alkylC(O)NR$^6$R$^7$ and —C$_{0-6}$ alkylC(O)C$_{1-6}$ alkyl; and
  R$^{2b}$ is hydrogen, C$_{1-3}$ alkyl, halo, cyano, —C$_{1-3}$ haloalkyl, —C$_{1-3}$ alkoxy, —C$_{0-6}$ alkylS(O)$_q$C$_{1-3}$ alkyl;

R$^{3a}$ is hydroxyl;
R$^{3b}$ is hydrogen, hydroxyl, halo, cyano, —C$_{1-3}$ haloalkyl, —C$_{1-3}$ hydroxyalkyl, —C$_{1-3}$ alkoxy, —S(O)$_q$C$_{1-3}$ alkyl;
R$^4$ is hydrogen or —C$_{1-3}$ alkyl;
R$^5$ is hydrogen or —C$_{1-3}$ alkyl;
R$^6$ is hydrogen or —C$_{1-6}$ alkyl;
R$^7$ is hydrogen or —C$_{1-6}$ alkyl;
R$^8$ is hydrogen or —C$_{1-6}$ alkyl;
p is 0 or an integer 1 or 2;
q is 0 or an integer 1 or 2
or a pharmaceutically acceptable salt thereof, including all stereoisomers, tautomers and isotopic derivatives thereof.

In one embodiment the present disclosure provides a compound of formula (IA'):

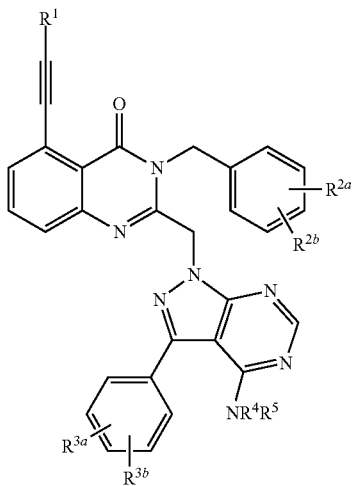

(IA')

R$^1$ is H, a saturated or unsaturated, branched or unbranched C$_{1-15}$ alkyl chain, wherein optionally one or more carbons (for example 1, 2 or 3 carbons, suitably 1 or 2, in particular 1) is/are replaced by a heteroatom selected from O, N, S(O)$_p$, (for example a CH$_2$, group is replaced with O, or with NH, or with S, or with SO$_2$ or a —CH$_3$ group at the terminus of the chain or on a branch is replaced with OH or with NH$_2$) wherein said chain is optionally substituted by one or more groups (for example 1 to 3, such as 2 groups) independently selected from oxo, halogen, an aryl group, a heteroaryl group, a carbocyclyl group or a heterocyclyl group, each aryl, heteroaryl, carbocyclyl or heterocyclyl group bearing:
  0 to 3 substituents selected from halogen, -hydroxyl, —C$_{1-6}$ alkyl, —C$_{1-6}$ alkoxy, —C$_{2-3}$ alkoxy-OC$_{1-3}$ alkyl, —C$_{2-3}$ alkylOC$_{1-3}$ alkyl, —C$_{1-3}$ hydroxyalkyl, —C$_{1-6}$ haloalkyl, amino, —C$_{1-4}$ mono or —C$_{2-8}$ di-alkyl amino, —C$_{1-4}$ mono or —C$_{2-8}$ di-acyl amino, —C$_{0-6}$ alkylS(O)$_p$C$_{1-6}$ alkyl, —C$_{0-6}$ alkylS(O)$_p$NR$^6$R$^7$, —C$_{0-6}$ alkylNR$^8$C$_{0-6}$alkylS(O)$_p$C$_{1-6}$ alkyl, —C$_{0-6}$ alkylC(O)OC$_{0-6}$ alkyl, —NR$^8$C$_{0-6}$ alkylC(O)NR$^6$R$^7$—NR$^8$C$_{0-6}$ alkylC(O)C$_{0-6}$ alkyl, —C$_{0-6}$ alkylC(O)NR$^6$R$^7$, and —C$_{0-6}$ alkylC(O)C$_{1-6}$ alkyl; and/or one aryl, heterocyclyl or carbocyclyl;

R$^{2a}$ is hydrogen, —C$_{1-3}$ alkyl, halo, hydroxyl, cyano, —C$_{1-3}$ haloalkyl, —C$_{1-3}$ alkoxy, —C$_{2-3}$ alkoxy-OC$_{1-3}$ alkyl, —C$_{1-3}$ hydroxyalkyl, —C$_{0-6}$ alkylS(O)$_p$C$_{1-3}$ alkyl, —C$_{0-6}$ alkylS(O)$_p$NR$^6$R$^7$, —C$_{0-6}$ alkylNR$^8$C$_{0-6}$alkylS(O)$_p$C$_{1-6}$ alkyl, —C$_{0-6}$ alkylC(O)OH, —C$_{0-6}$ alkylC(O)OC$_{1-6}$ alkyl, —NC$_{0-6}$ alkylC(O)NR$^6$R$^7$, —NR$^8$C$_{0-6}$ alkylC(O)C$_{1-6}$ alkyl, —C$_{0-6}$ alkylC(O)NR$^6$R$^7$ and —C$_{0-6}$ alkylC(O)C$_{1-6}$ alkyl;

R$^{2b}$ is hydrogen, C$_{1-3}$ alkyl, halo, cyano, C$_{1-3}$ haloalkyl, C$_{1-3}$ alkoxy, C$_{0-6}$ alkylS(O)$_p$C$_{1-3}$ alkyl;

R$^{3a}$ is hydroxyl;
R$^{3b}$ is hydrogen, hydroxyl, halo, cyano, C$_{1-3}$ haloalkyl, C$_{1-3}$ hydroxyalkyl, C$_{1-3}$ alkoxy, S(O)$_q$C$_{1-3}$ alkyl;
R$^4$ is hydrogen or —C$_{1-3}$ alkyl;
R$^5$ is hydrogen or —C$_{1-3}$ alkyl;
R$^6$ is hydrogen or —C$_{1-6}$ alkyl;
R$^7$ is hydrogen or —C$_{1-6}$ alkyl;
R$^8$ is hydrogen or —C$_{1-6}$ alkyl;
p is 0 or an integer 1 or 2;
q is 0 or an integer 1 or 2
or a pharmaceutically acceptable salt thereof, including all stereoisomers, tautomers and isotopic derivatives thereof.

In one embodiment the present disclosure provides a compound of formula (IA):

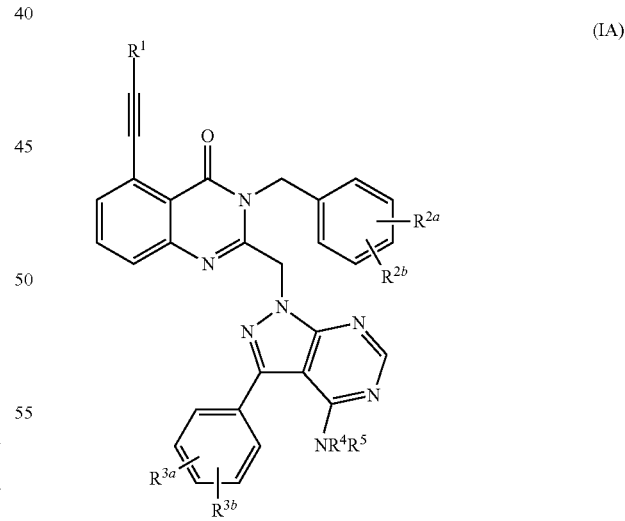

(IA)

R$^1$ is H, a saturated or unsaturated, branched or unbranched C$_{1-15}$ alkyl chain (such as a C$_{1-12}$ alkyl chain or a C$_{1-10}$ alkyl chain), wherein optionally one or more carbons (for example 1, 2 or 3 carbons, suitably 1 or 2, in particular 1) is/are replaced by a heteroatom selected from O, N, S(O)$_p$, (for example a CH$_2$, group is replaced with O, or with NH, or with S, or with SO$_2$ or a —CH$_3$ group at the terminus of the chain or on a branch is replaced with OH or with NH$_2$) wherein said chain is optionally substituted by one or more groups independently selected from oxo, halogen, an aryl group, a heteroaryl group, a carbocyclyl group or a heterocyclyl group each aryl, heteroaryl, carbocyclyl or heterocyclyl group bearing:
0 to 3 substituents selected from halogen, —C$_{1-6}$ alkyl, —C$_{1-6}$ alkoxy, —C$_{2-3}$ alkoxy-OC$_{1-3}$ alkyl, —C$_{1-6}$ haloalkyl, amino, —C$_{1-4}$ mono or —C$_{2-8}$ di-alkyl amino, —C$_{1-4}$ mono or —C$_{2-8}$ di-acyl amino, —C$_{0-6}$ alkylS(O)$_p$C$_{1-6}$ alkyl, —C$_{0-6}$ alkylS(O)$_p$NR$^6$R$^7$, —C$_{0-6}$ alkylNR$^8$C$_{0-6}$alkylS(O)$_p$C$_{1-6}$ alkyl, —C$_{0-6}$ alkylC(O)OC$_{0-6}$ alkyl, —NC$_{0-6}$ alkylC(O)NR$^6$R$^7$—NC$_{0-6}$ alkylC(O)C$_{0-6}$ alkyl, —C$_{0-6}$ alkylC(O)NR$^6$R$^7$, and —C$_{0-6}$ alkylC(O)C$_{1-6}$ alkyl; and/or one aryl, heterocyclyl or carbocyclyl;

R$^{2a}$ is hydrogen, —C$_{1-3}$ alkyl, halo, hydroxyl, cyano, —C$_{1-3}$ haloalkyl, —C$_{1-3}$ alkoxy, —C$_{2-3}$ alkoxy-OC$_{1-3}$ alkyl, —C$_{1-3}$ hydroxyalkyl, —C$_{0-6}$ alkylS(O)$_q$C$_{1-3}$ alkyl, —C$_{0-6}$ alkylS(O)$_p$NR$^6$R$^7$, —C$_{0-6}$ alkylNR$^8$C$_{0-6}$alkylS(O)$_p$C$_{1-6}$ alkyl, —C$_{0-6}$ alkylC(O)OH, —C$_{0-6}$ alkylC(O)OC$_{1-6}$ alkyl, —NC$_{0-6}$ alkylC(O)NR$^6$R$^7$, —NR$^8$C$_{0-6}$ alkylC(O)C$_{1-6}$ alkyl, —C$_{0-6}$ alkylC(O)NR$^6$R$^7$ and —C$_{0-6}$ alkylC(O)C$_{1-6}$ alkyl;

R$^{2b}$ is hydrogen, C$_{1-3}$ alkyl, halo, cyano, C$_{1-3}$ haloalkyl, C$_{1-3}$ alkoxy, C$_{0-6}$ alkylS(O)$_q$C$_{1-3}$ alkyl;

R$^{3a}$ is hydroxyl;

R$^{3b}$ is hydrogen, hydroxyl, halo, cyano, C$_{1-3}$ haloalkyl, C$_{1-3}$ hydroxyalkyl, C$_{1-3}$ alkoxy, S(O)$_q$C$_{1-3}$ alkyl;

R$^4$ is hydrogen or —C$_{1-3}$ alkyl;
R$^5$ is hydrogen or —C$_{1-3}$ alkyl;
R$^6$ is hydrogen or —C$_{1-6}$ alkyl;
R$^7$ is hydrogen or —C$_{1-6}$ alkyl;
R$^8$ is hydrogen or —C$_{1-6}$ alkyl;
p is 0 or an integer 1 or 2;
q is 0 or an integer 1 or 2
or a pharmaceutically acceptable salt thereof, including all stereoisomers, tautomers and isotopic derivatives thereof.

According to the invention, there is provided a compound of formula (IB'):

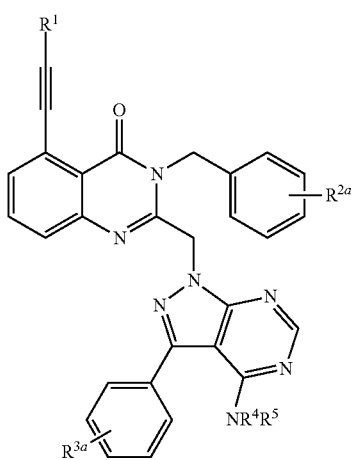

IB' wherein
R$^1$ is H, a saturated or unsaturated, branched or unbranched C$_{1-15}$ alkyl chain, wherein optionally one or more carbons (for example 1, 2 or 3 carbons, suitably 1 or 2, in particular 1) is/are replaced by a heteroatom selected from O, N, S(O)$_p$, (for example a CH$_2$, group is replaced with O, or with NH, or with S, or with SO$_2$ or a —CH$_3$ group at the terminus of the chain or on a branch is replaced with OH or with NH$_2$) wherein said chain is optionally substituted by one or more groups (for example 1 to 3, such as 2 groups) independently selected from oxo, halogen, an aryl group, a heteroaryl group, a carbocyclyl group or a heterocyclyl group, each aryl, heteroaryl, carbocyclyl or heterocyclyl group bearing:
0 to 3 substituents selected from halogen, -hydroxyl, —C$_{1-6}$ alkyl, —C$_{1-6}$ alkoxy, —C$_{2-3}$ alkoxy-OC$_{1-3}$ alkyl, —C$_{2-3}$ alkylOC$_{1-3}$ alkyl, —C$_{1-3}$ hydroxyalkyl, —C$_{1-6}$ haloalkyl, amino, —C$_{1-4}$ mono or —C$_{2-8}$ di-alkyl amino, —C$_{1-4}$ mono or —C$_{2-8}$ di-acyl amino, —C$_{0-6}$ alkylS(O)$_p$C$_{1-6}$ alkyl, —C$_{0-6}$ alkylS(O)$_p$NR$^6$R$^7$, —C$_{0-6}$ alkylNR$^8$C$_{0-6}$alkylS(O)$_p$C$_{1-6}$ alkyl, —C$_{0-6}$ alkylC(O)OC$_{0-6}$ alkyl, —NR$^8$C$_{0-6}$ alkylC(O)NR$^6$R$^7$—NR$^8$C$_{0-6}$ alkylC(O)C$_{0-6}$ alkyl, —C$_{0-6}$ alkylC(O)NR$^6$R$^7$, and —C$_{0-6}$ alkylC(O)C$_{1-6}$ alkyl; and/or one aryl, heterocyclyl or carbocyclyl;

R$^{2a}$ is hydrogen, —C$_{1-3}$ alkyl, halo, hydroxyl, cyano, —C$_{1-3}$ haloalkyl, —C$_{1-3}$ alkoxy, —C$_{2-3}$ alkoxy-OC$_{1-3}$ alkyl, —C$_{1-3}$ hydroxyalkyl, —C$_{0-6}$ alkylS(O)$_p$C$_{1-3}$ alkyl, —C$_{0-6}$ alkylS(O)$_p$NR$^6$R$^7$, —C$_{0-6}$ alkylNR$^8$C$_{0-6}$alkylS(O)$_p$C$_{1-6}$ alkyl, —C$_{0-6}$ alkylC(O)OH, —C$_{0-6}$ alkylC(O)OC$_{1-6}$ alkyl, —NC$_{0-6}$ alkylC(O)NR$^6$R$^7$, —NR$^8$C$_{0-6}$ alkylC(O)C$_{1-6}$ alkyl, —C$_{0-6}$ alkylC(O)NR$^6$R$^7$ and —C$_{0-6}$ alkylC(O)C$_{1-6}$ alkyl;

R$^{3a}$ is hydroxyl;
R$^4$ is hydrogen or —C$_{1-3}$ alkyl;
R$^5$ is hydrogen or —C$_{1-3}$ alkyl;
R$^6$ is hydrogen or —C$_{1-6}$ alkyl;
R$^7$ is hydrogen or —C$_{1-6}$ alkyl;
R$^8$ is hydrogen or —C$_{1-6}$ alkyl;
p is 0 or an integer 1 or 2;
q is o or an integer 1 or 2
or a pharmaceutically acceptable salt thereof, including all stereoisomers, tautomers and isotopic derivatives thereof.

According to the invention, there is provided a compound of formula (IB):

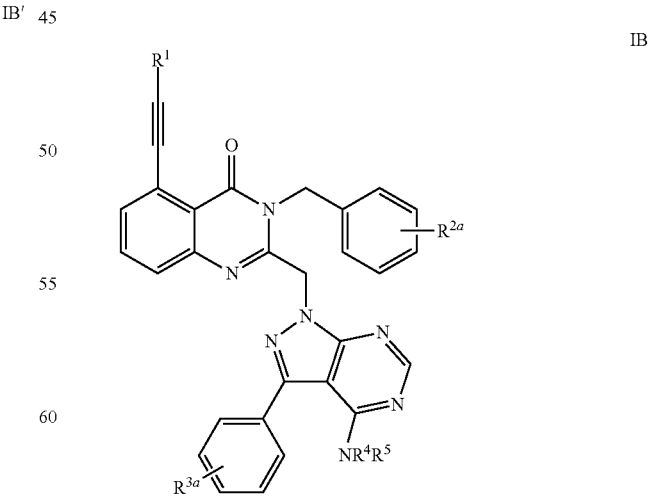

IB wherein
R$^1$ is H, a saturated or unsaturated, branched or unbranched C$_{1-15}$ alkyl chain (such as a C$_{1-12}$ alkyl chain or a C$_{1-10}$ alkyl chain), wherein optionally one or more carbons (for example 1, 2 or 3 carbons, suitably 1 or 2, in particular 1) is/are replaced by a heteroatom selected from O, N, S(O)$_p$, (for example a CH$_2$, group is replaced with O, or with NH, or with S, or with SO$_2$ or a —CH$_3$ group at the terminus of the chain or on a branch is replaced with OH or with NH$_2$) wherein said chain is optionally substituted by one or more groups independently selected from oxo, halogen, an aryl group, a heteroaryl group, a carbocyclyl group or a heterocyclyl group each aryl, heteroaryl, carbocyclyl or heterocyclyl group bearing:
0 to 3 substituents selected from halogen, —C$_{1-6}$ alkyl, —C$_{1-6}$ alkoxy, —C$_{2-3}$ alkoxy-OC$_{1-3}$ alkyl, —C$_{1-6}$ haloalkyl, amino, —C$_{1-4}$ mono or —C$_{2-8}$ di-alkyl amino, —C$_{1-4}$ mono or —C$_{2-8}$ di-acyl amino, —C$_{0-6}$ alkylS(O)$_p$C$_{1-s}$ alkyl, —C$_{0-6}$ alkylS(O)$_p$NR$^6$R$^7$, —C$_{0-6}$ alkylNR$^8$C$_{0-6}$alkylS(O)$_p$C$_{1-6}$ alkyl, —C$_{0-6}$ alkylC(O)OC$_{0-6}$ alkyl, —NC$_{0-6}$ alkylC(O)NR$^6$R$^7$— NC$_{0-6}$ alkylC(O)C$_{0-6}$ alkyl, —C$_{0-6}$ alkylC(O)NR$^6$R$^7$, and —C$_{0-6}$ alkylC(O)C$_{1-6}$ alkyl; and/or one aryl, heterocyclyl or carbocyclyl;

R$^{2a}$ is hydrogen, —C$_{1-3}$ alkyl, halo, hydroxyl, cyano, —C$_{1-3}$ haloalkyl, —C$_{1-3}$ alkoxy, —C$_{2-3}$ alkoxy-OC$_{1-3}$ alkyl, —C$_{1-3}$ hydroxyalkyl, —C$_{0-6}$ alkylS(O)$_q$C$_{1-3}$ alkyl, —C$_{0-6}$ alkylS(O)$_p$NR$^6$R$^7$, —C$_{0-6}$ alkylNR$^8$C$_{0-6}$alkylS(O)$_p$C$_{1-6}$ alkyl, —C$_{0-6}$ alkylC(O)OH, —C$_{0-6}$ alkylC(O)OC$_{1-6}$ alkyl, —NC$_{0-6}$ alkylC(O)NR$^6$R$^7$, —NR$^8$C$_{0-6}$ alkylC(O)C$_{1-6}$ alkyl, —C$_{0-6}$ alkylC(O)NR$^6$R$^7$ and —C$_{0-6}$ alkylC(O)C$_{1-6}$ alkyl;

R$^{3a}$ is hydroxyl;
R$^4$ is hydrogen or —C$_{1-3}$ alkyl;
R$^5$ is hydrogen or —C$_{1-3}$ alkyl;
R$^6$ is hydrogen or —C$_{1-6}$ alkyl;
R$^7$ is hydrogen or —C$_{1-6}$ alkyl;
R$^8$ is hydrogen or —C$_{16}$ alkyl;
p is 0 or an integer 1 or 2;
q is 0 or an integer 1 or 2
or a pharmaceutically acceptable salt thereof, including all stereoisomers, tautomers and isotopic derivatives thereof.

In one embodiment there is provided a compound of formula (IC):

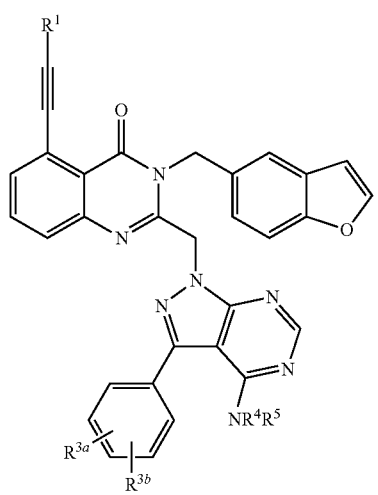

(IC)

wherein R$^1$, R$^{3a}$, R$^{3b}$, R$^4$ and R$^5$ are as defined above for compounds of formula (I).

In one embodiment there is provided a compound of formula (ID):

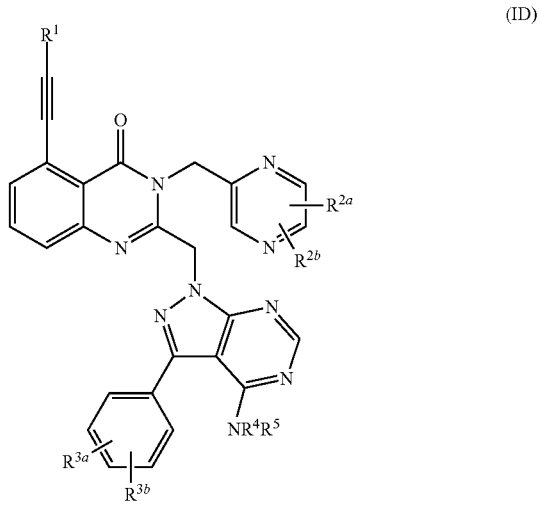

(ID)

wherein R$^1$, R$^{2a}$, R$^{2b}$, R$^{3a}$, R$^{3b}$, R$^4$ and R$^5$ are as defined above for compounds of formula (I).

In one embodiment there is provided a compound of formula (IE):

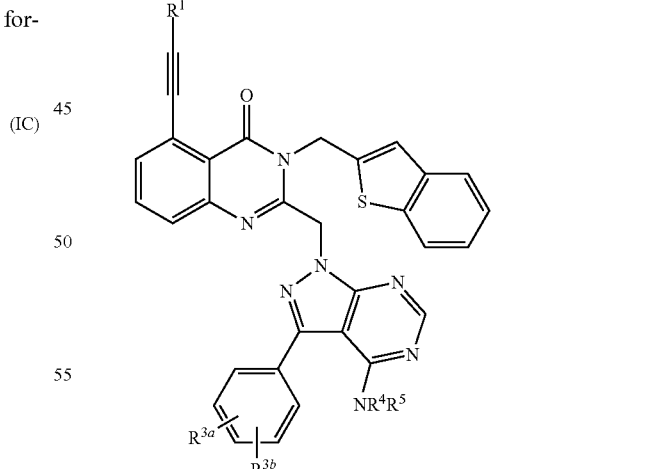

(IE)

wherein R$^1$, R$^{3a}$, R$^{3b}$, R$^4$ and R$^5$ are as defined above for compounds of formula (I).

In one embodiment there is provided a compound of formula (IF):

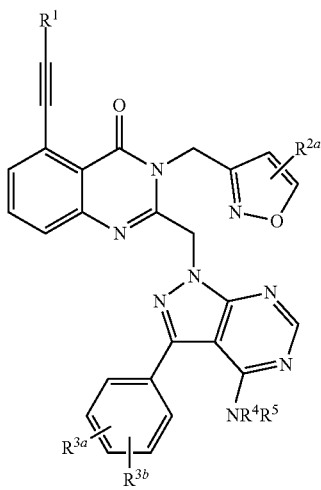

wherein $R^1$, $R^{2a}$, $R^{3a}$, $R^{3b}$, $R^4$ and $R^5$ are as defined above for compounds of formula (I).

In one embodiment there is provided a compound of formula (IG):

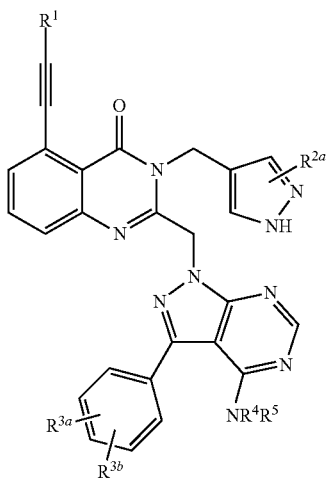

wherein $R^1$, $R^{2a}$, $R^{3a}$, $R^{3b}$, $R^4$ and $R^5$ are as defined above for compounds of formula (I).

The compounds of the present disclosure are at least PI3K delta inhibitors. Certain compound of the disclosure may be PI3K alpha and delta inhibitors. Certain compounds of the disclosure may be PI3K delta and gamma inhibitors. Some compounds may be alpha and gamma isozyme inhibitors. Other compounds may be alpha, delta and gamma subtype inhibitors. It is proposed that different biological profiles may be associated with these different inhibition profiles which may be advantageous in targeting pathways for different diseases.

Inhibitor as employed here is intended to refer to a compound that reduces (for example by at least 50%) or eliminates the biological activity of the target, for example PI3K delta, in an in vitro enzyme assay.

The compounds of the present disclosure are active in cell based screening systems and thereby demonstrate that they possess suitable properties for penetrating cells.

General references to compounds of formula (I) herein are intended to include references to compounds of formula (IA)-(IG) unless the context suggests otherwise.

Alkyl as used herein refers to straight chain or branched chain alkyl, such as, without limitation, methyl, ethyl, propyl, iso-propyl, butyl, and tert-butyl. In one embodiment alkyl refers to straight chain alkyl.

Alkoxy as used herein refers to straight or branched chain alkoxy, for example methoxy, ethoxy, propoxy, butoxy. Alkoxy as employed herein also extends to embodiments in which the oxygen atom is located within the alkyl chain, for example $-(CH_2)_nOCH_3$. In one embodiment the alkoxy is linked through oxygen to the remainder of the molecule. In one embodiment the alkoxy is linked through carbon to the remainder of the molecule. In one embodiment the disclosure relates to straight chain alkoxy.

—$C_{2-3}$ alkoxy-$OC_{1-3}$ alkyl as employed herein is intended to refer an —$C_{2-3}$ alkoxy linked to the remainder of the molecule through oxygen to provide oxygen-alkylene-oxygen-alkyl.

Carbocyclyl as employed herein is intended to refer to $C_{3-10}$ saturated or partially saturated carbocyclic ring systems, for example cyclopropyl, cyclobutyl, cyclopentyl and cyclohexyl.

Heteroaryl is a $C_{5-9}$ membered aromatic carbocylic ring or bicyclic ring system comprising one or more, (for example 1, 2, 3 or 4) heteroatoms independently selected from O, N and S. Examples of heteroaryls include: pyrrole, oxazole, thiazole, isothiazole, imidazole, pyrazole, isoxazole, pyridazine, pyrimidine, pyrazine, benzothiophene, benzofuran, or 1, 2, 3 and 1, 2, 4 triazole. In a bicyclic ring system the definition of heteroaryl will be satisfied if at least one ring contains a heteroatom and at least one ring is aromatic. The heteroaryl may be linked to the remainder of the molecule through a carbocyclic ring or a ring comprising a heteroatom.

In a bicyclic system the definition of aromatic will be satisfied by the aromatic nature of at least one ring in the system.

Heterocyclic groups as employed herein is intended to refer to a 5 to 10 membered ring system which is saturated or partially unsaturated and which is non-aromatic comprising one or more (for example 1, 2 or 3 in particular 1 or 2,) heteroatoms independently selected from O, N and S, for example 5 or 6 or 7 membered rings including pyrrolidine, tetrahydrofuran, tetrahydrothiophene, piperidine, piperazine, morpholine, 1,4-dioxane, pyrrolidine and oxoimidazolidine such as pyrrolidine, tetrahydrofuran, tetrahydrothiophene, piperidine, piperazine, morpholine, and 1,4-dioxane, and in particular piperidine, piperazine, and morpholine. An example of a saturated 7 membered heterocyclic ring is a 1,4-diazepane ring and an example of a partially unsaturated 7 membered ring is a 2,3,4,5-tetrahydro-1,4-oxazepine.

A heterocyclic group may be linked to, for example, an alkyl chain, through carbon or a suitable heteroatom such as N.

Oxo as employed herein refers to the group =O and can be attached to a carbon atom to give C=O or to a heteroatom to give, for example, S=O or $SO_2$.

Haloalkyl as employed herein is intended to refer to a group having from 1 to 6 halo atoms, for example 1 to 5 halo atoms. In one embodiment the haloalkyl is per haloalkyl, for example per fluoroalkyl, such as $CF_2CF_3$ and $CF_3$.

Halo represents bromo, chloro or fluoro.

$C_{1-4}$ mono or $C_{2-8}$ di acyl is intended to refer to —$C(O)C_{1-4}$ alkyl and —$(COC_{1-4}$ alkyl$)_2$ respectively.

Aryl as used herein refers to, for example $C_{6-14}$ mono or polycyclic groups (such as $C_{6-10}$ mono or bicyclic groups)

having from 1 to 3 rings wherein at least one ring is aromatic including phenyl, napthyl, anthracenyl, 5,6,7,8-tetrahydronapthyl and the like, such as phenyl and napthyl.

In one embodiment X is phenyl.

In one embodiment X is a $C_{5-9}$ membered heteroaryl.

In one embodiment X is pyrazinyl, such as pyrazin-2-yl, in particular methylpyrazin-2-yl, more specifically 5-methylpyrazin-2-yl.

In one embodiment X is benzothiophenyl, for example benzothiophen-2-yl.

In one embodiment X is benzofuranyl, for example benzofura-5-yl.

In one embodiment X is thiazolyl, for example thiazol-4-yl.

In one embodiment X is isoxazolyl, for example isoxazol-3-yl, such as 5-methylisoxazol-3-yl.

In $R^1$ a suitable heteroatom may replace any carbon including a linking carbon, branched carbon or a terminal carbon and hydrogen(s) may fill the remaining valencies, as appropriate.

In one embodiment $R^1$ is H.

In another embodiment $R^1$ is branched or unbranched $C_{1-10}$ alkyl chain, wherein at least one carbon (for example 1, 2 or 3 carbons) is replaced by an oxygen, for example $C_9$ alkyl comprising 1, 2 or 3 oxygen atoms, such as —$CH_2OCH_2CH_2OCH_2CH_2OCH_3$.

In one embodiment $R^1$ is —$CH_2OCH_3$.

In one embodiment $R^1$ is —$CH_2CH_2CH_2OH$.

In one embodiment $R^1$ is —$CH_2OCH_2CH_2OCH_2CH_2OH$.

In one embodiment $R^1$ bears at least one oxo substituent.

In one embodiment $R^1$ is —$CH_2NHCONH_2$.

In one embodiment $R^1$ bears at least one carbocyclic group as a substitutent.

In one embodiment $R^1$ bears at least one oxo substituent and a carbocyclic group substituent, for example cyclopentyl or cyclohexyl linked to a carbon bearing an oxo substituent, such as the fragment:

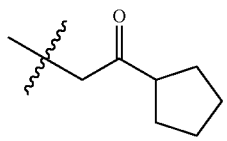 [SMILES: *CC(=O)C1CCCC1]

In one embodiment $R^1$ comprises:

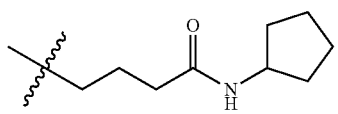 [SMILES: *CCCC(=O)NC1CCCC1]

In one embodiment $R^1$ comprises:

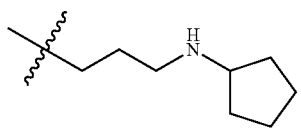 [SMILES: *CCCNC1CCCC1]

In one embodiment $R^1$ comprises:

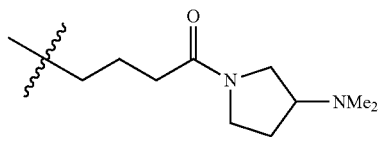 [SMILES: *CCCC(=O)N1CCC(N(C)C)C1]

In one embodiment $R^1$ comprises:

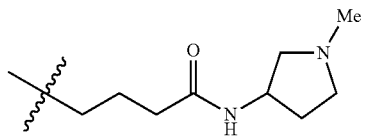 [SMILES: *CCCC(=O)NC1CCN(C)C1]

In one embodiment $R^1$ bears at least one heterocyclic group substituent.

In one embodiment $R^1$ bears one oxo substituent and one heterocyclic group substituent, for example the heterocyclic group is linked to a carbon bearing an oxo substituent, such as $R^1$ comprising —C(O)morpholinyl wherein the morpholinyl may be linked through N, in particular the fragment:

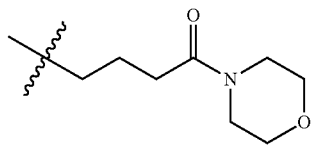 [SMILES: *CCCC(=O)N1CCOCC1]

or
—C(O)piperidinyl such as the fragment:

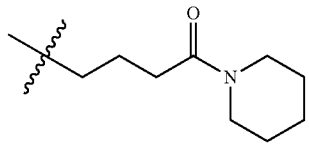 [SMILES: *CCCC(=O)N1CCCCC1]

In one embodiment $R^1$ bears one oxo substituent and one heterocyclic group substituent, for example the heterocyclic group is linked to a carbon bearing an oxo substituent, wherein said heterocyclic group itself bears a $C_{1-6}$ alkyl or a —C(O)$C_{1-6}$ alkyl substitutent, such as $R^1$ comprising —C(O)piperidinyl$C_{1-6}$ alkyl or —C(O)piperidinylC(O)$C_{1-6}$ alkyl wherein the piperidinyl may be linked through N, in particular the fragments:

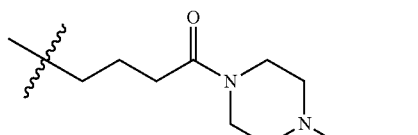

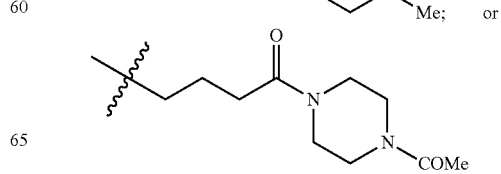

In one embodiment R¹ represents:

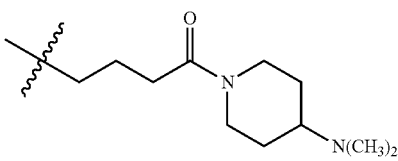 [SMILES: *CCCC(=O)N1CCC(N(C)C)CC1]

In one embodiment R¹ represents:

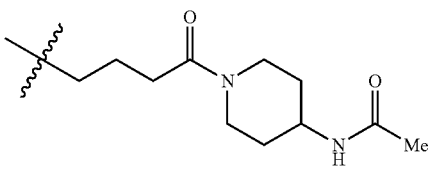 [SMILES: *CCCC(=O)N1CCC(NC(C)=O)CC1]

In one embodiment R1 represents:

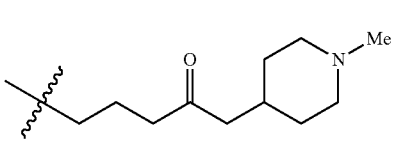 [SMILES: *CCCC(=O)CC1CCN(C)CC1]

In one embodiment R¹ bears one oxo substituent and one heterocyclic group substituent, for example the heterocyclic group is linked to a carbon bearing an oxo substituent, wherein said heterocyclic group itself bears a heterocyclic group as a substituent thereon, such as R¹ comprising —C(O) piperidinylmorpholinyl wherein the morpholinyl may be linked through N, in particular the fragment:

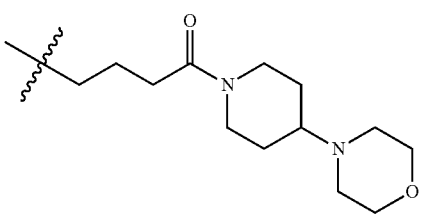 [SMILES: *CCCC(=O)N1CCC(N2CCOCC2)CC1]

In one embodiment R¹ comprises:

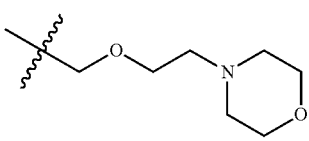 [SMILES: *COCCN1CCOCC1]

In one embodiment R¹ comprises:

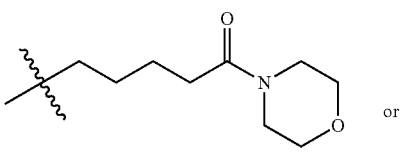 or

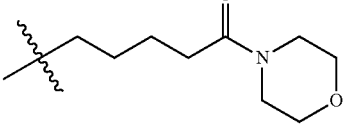

In one embodiment R¹ comprises:

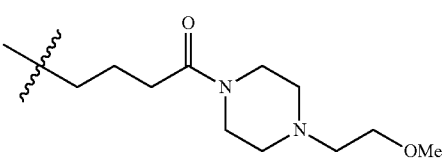 [SMILES: *CCCC(=O)N1CCN(CCOC)CC1]

In one embodiment R¹ represents:

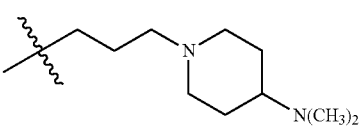 [SMILES: *CCCN1CCC(N(C)C)CC1]

In one embodiment R¹ represents:

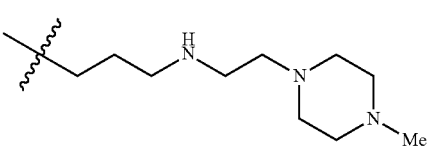 [SMILES: *CCCNCCN1CCN(C)CC1]

In one embodiment R¹ represents:

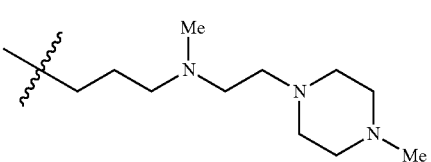 [SMILES: *CCCN(C)CCN1CCN(C)CC1]

In one embodiment R¹ represents:

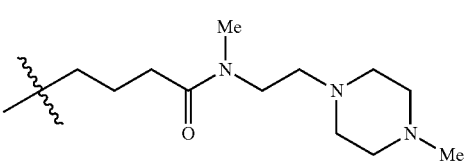 [SMILES: *CCCC(=O)N(C)CCN1CCN(C)CC1]

In one embodiment R¹ represents:

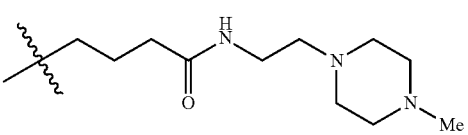 [SMILES: *CCCC(=O)NCCN1CCN(C)CC1]

In one embodiment R¹ represents:

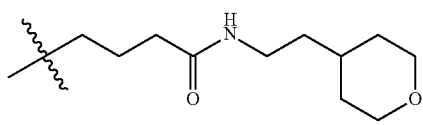 [SMILES: *CCCC(=O)NCCC1CCOCC1]

In one embodiment R¹ represents:

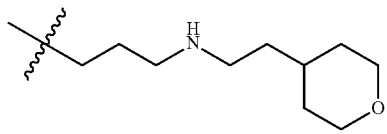 [SMILES: *CCCNCCC1CCOCC1]

In one embodiment R¹ represents:

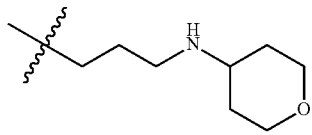 [SMILES: *CCCNC1CCOCC1]

In one embodiment R¹ represents:

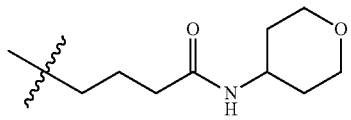 [SMILES: *CCCC(=O)NC1CCOCC1]

In one embodiment R¹ represents:

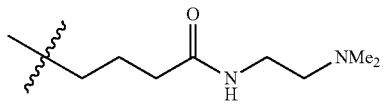 [SMILES: *CCCC(=O)NCCN(C)C]

In one embodiment R¹ represents:

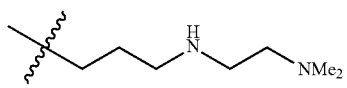 [SMILES: *CCCNCCN(C)C]

In one embodiment R¹ represents:

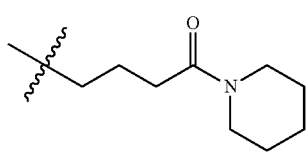 [SMILES: *CCCC(=O)N1CCCCC1]

In one embodiment R¹ represents:

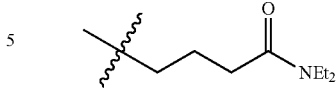

In one embodiment R¹ comprises a carboxylic acid, for example $C_{1-3}$ alkyleneCO$_2$H such as the fragment —CH$_2$CH$_2$CH$_2$CO$_2$H or alternatively —CH$_2$CH$_2$CH$_2$CH$_2$CO$_2$H.

In one embodiment R¹ represents —CH$_2$CH$_2$CH$_2$C(O)NHCH(CH$_3$)$_2$.

In one embodiment R¹ represents —CH$_2$CH$_2$CH$_2$C(O)(CH$_3$)$_2$.

In one embodiment R¹ represents —CH$_2$CH$_2$CH$_2$NHCH$_2$CH$_2$OCH$_3$.

In one embodiment R¹ represents —CH$_2$CH$_2$CH$_2$N(CH$_2$CH$_2$OCH$_3$)$_2$.

In one embodiment R¹ represents —CH$_2$CH$_2$CH$_2$C(O)N(CH$_2$CH$_2$OCH$_3$)$_2$.

In one embodiment R¹ represents —CH$_2$NHC(O)CH$_2$NHC(O)CH$_3$.

In one embodiment R¹ represents —CH$_2$CH$_2$CH$_2$C(O)NHCH$_2$CH$_2$OCH$_3$.

In one embodiment R¹ comprises:

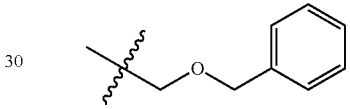

In one embodiment R¹ comprises:

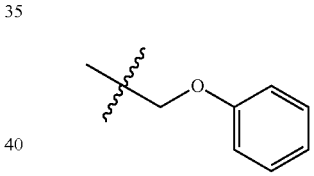

In one embodiment R¹ represents:

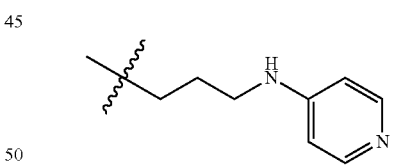

In one embodiment R¹ represents:

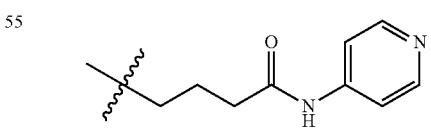

In one embodiment $R^{2a}$ is located in the ortho position.
In one embodiment $R^{2a}$ is located in the meta position.
In one embodiment $R^{2a}$ is located in the para position.
In one embodiment $R^{2a}$ is $C_{1-3}$alkyl, halo, cyano, $C_{1-3}$ haloalkyl, $C_{1-3}$ alkoxy, $S(O)_qC_{1-3}$ alkyl, —C(O)OC$_{1-6}$ alkyl, —NC(O)NC$_{1-6}$ alkyl, —NC(O)C$_{1-6}$ alkyl, —C(O)NC$_{1-6}$ alkyl, and —C(O)C$_{1-6}$ alkyl.

In one embodiment $R^{2a}$ is selected from the group comprising methyl, chloro, fluoro, cyano, methoxy, trifluoromethyl and $SO_2CH_3$.

In one embodiment $R^{2a}$ is chloro.
In one embodiment $R^{2a}$ is fluoro.
In one embodiment $R^{2a}$ is cyano.
In one embodiment $R^{2a}$ is methoxy.
In one embodiment $R^{2a}$ is methyl.
In one embodiment $R^{2a}$ is $SO_2CH_3$.
In one embodiment $R^{2a}$ is —C(O)OCH$_3$.
In one embodiment $R^{2a}$ is $CF_3$.
In one embodiment $R^{2b}$ is hydrogen.
In one embodiment $R^{2b}$ is chloro.
In one embodiment $R^{2b}$ is —OCH$_3$.
In one embodiment $R^{2a}$ are $R^{2b}$ are in the 2, 3 or 2, 4 or 3, 4, or 3, 5 positions respectively.
In one embodiment $R^{2a}$ is $CF_3$ and $R^{2b}$ is methoxy.
$R^{3a}$ is suitably in the ortho, meta or para position, such as the ortho or para position.
In one embodiment $R^{3b}$ is hydrogen.
In one embodiment $R^{3b}$ is fluoro or chloro, for example in the 4-position.
In one embodiment $R^{3a}$ and $R^{3b}$ are in the 3, 4 position respectively.
In one embodiment $R^4$ is H.
In one embodiment $R^5$ is H.
In one embodiment p is 2.
In one embodiment q is 2.
In one embodiment there is a provided a pharmaceutically acceptable acid addition salt of a compound of formula (I).

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Examples of salts of compound (I) include all pharmaceutically acceptable salts, such as, without limitation, acid addition salts of mineral acids such as HCl and HBr salts and addition salts of organic acids such as a methansulfonic acid salt.

The disclosure also extends to solvates of the compounds herein. Examples of solvates include hydrates.

The compounds of the disclosure include those where the atom specified is a naturally occurring or non-naturally occurring isotope. In one embodiment the isotope is a stable isotope. Thus the compounds of the disclosure include, for example those containing one or more deuterium atoms in place of hydrogen atoms and the like.

The compounds described herein may include one or more chiral centres, and the disclosure extends to include racemates, both enantiomers (for example each substantially free of the other enantiomer) and all stereoisomers resulting therefrom. In one embodiment one enantiomeric form is present in a purified form that is substantially free of the corresponding entaniomeric form.

The disclosure also extends to all polymorphic forms of the compounds herein defined.

In one aspect a compound of formula (I) is:
2-((4-Amino-3-(3-hydroxyphenyl)-1H-pyrazolo[3,4-d]pyrimidin-1-yl)methyl)-3-(2-chloro benzyl)-5-ethynylquinazolin-4(3H)-one;
2-((4-Amino-3-(3-hydroxyphenyl)-1H-pyrazolo[3,4-d]pyrimidin-1-yl)methyl)-3-(2-chloro benzyl)-5-(3-(2-(2-methoxyethoxy)ethoxy)prop-1-yn-1-yl)quinazolin-4(3H)-one;
2-((4-Amino-3-(3-hydroxyphenyl)-1H-pyrazolo[3,4-d]pyrimidin-1-yl)methyl)-3-(2-chloro benzyl)-5-(6-morpholino-6-oxohex-1-yn-1-yl)quinazolin-4(3H)-one;
6-(2-((4-Amino-3-(4-hydroxyphenyl)-1H-pyrazolo[3,4-d]pyrimidin-1-yl)methyl)-3-(2-chloro benzyl)-4-oxo-3,4-dihydroquinazolin-5-yl)hex-5-ynoic acid;
2-((4-Amino-3-(4-hydroxyphenyl)-1H-pyrazolo[3,4-d]pyrimidin-1-ylmethyl)-3-(2-chloro benzyl)-5-(6-morpholino-6-oxohex-1-yn-1-yl)quinazolin-4(3H)-one;
3-((2-((4-Amino-3-(3-hydroxyphenyl)-1H-pyrazolo[3,4-d]pyrimidin-1-yl)methyl)-5-(3-(2-(2-hydroxyethoxy)ethoxy)prop-1-yn-1-yl)-4-oxoquinazolin-3(4H)-ylmethyl)benzonitrile;
2-((4-amino-3-(3-hydroxyphenyl)-1H-pyrazolo[3,4-d]pyrimidin-1-yl)methyl)-3-(2-chlorobenzyl)-5-(3-(2-morpholinoethoxy)prop-1-ynyl)quinazolin-4(3H)-one;
2-((4-Amino-3-(4-hydroxyphenyl)-1H-pyrazolo[3,4-d]pyrimidin-1-ylmethyl)-3-(2-chloro benzyl)-5-ethynylquinazolin-4(3H)-one;
2-((4-Amino-3-(3-hydroxyphenyl)-1H-pyrazolo[3,4-d]pyrimidin-1-ylmethyl)-3-(3-chloro benzyl)-5-ethynylquinazolin-4(3H)-one;
2-((4-Amino-3-(4-hydroxyphenyl)-1H-pyrazolo[3,4-d]pyrimidin-1-ylmethyl)-3-(3-chloro benzyl)-5-ethynylquinazolin-4(3H)-one;
2-((4-Amino-3-(3-hydroxyphenyl)-1H-pyrazolo[3,4-d]pyrimidin-1-ylmethyl)-5-ethynyl-3-(2-fluorobenzyl)quinazolin-4(3H)-one;
2-((4-Amino-3-(4-hydroxyphenyl)-1H-pyrazolo[3,4-d]pyrimidin-1-ylmethyl)-5-ethynyl-3-(2-fluorobenzyl)quinazolin-4(3H)-one;
2-((4-Amino-3-(4-hydroxyphenyl)-1H-pyrazolo[3,4-d]pyrimidin-1-ylmethyl)-5-ethynyl-3-(3-methoxybenzyl)quinazolin-4(3H)-one;
2-((4-Amino-3-(3-hydroxyphenyl)-1H-pyrazolo[3,4-d]pyrimidin-1-ylmethyl)-5-ethynyl-3-(3-methoxybenzyl)quinazolin-4(3H)-one;
2-((4-Amino-3-(4-hydroxyphenyl)-1H-pyrazolo[3,4-d]pyrimidin-1-ylmethyl)-5-ethynyl-3-(3-(trifluoromethyl)benzyl)quinazolin-4(3H)-one;
2-((4-Amino-3-(3-hydroxyphenyl)-1H-pyrazolo[3,4-d]pyrimidin-1-ylmethyl)-5-ethynyl-3-(3-(trifluoromethyl)benzyl)quinazolin-4(3H)-one;
2-((4-Amino-3-(4-hydroxyphenyl)-1H-pyrazolo[3,4-d]pyrimidin-1-ylmethyl)-3-(4-chloro benzyl)-5-ethynyl quinazolin-4(3H)-one;
2-((4-Amino-3-(3-hydroxyphenyl)-1H-pyrazolo[3,4-d]pyrimidin-1-ylmethyl)-5-ethynyl-3-(4-(methylsulfonyl)benzyl)quinazolin-4(3H)-one;
2-((4-Amino-3-(4-hydroxyphenyl)-1H-pyrazolo[3,4-d]pyrimidin-1-ylmethyl)-5-ethynyl-3-(4-(methylsulfonyl)benzyl)quinazolin-4(3H)-one;
2-((4-Amino-3-(3-hydroxyphenyl)-1H-pyrazolo[3,4-d]pyrimidin-1-ylmethyl)-5-ethynyl-3-(4-(trifluoromethyl)benzyl)quinazolin-4(3H)-one;
3-((2-((4-Amino-3-(4-hydroxyphenyl)-1H-pyrazolo[3,4-d]pyrimidin-1-ylmethyl)-5-ethynyl-4-oxoquinazolin-3(4H)-ylmethyl)benzonitrile;

2-((4-Amino-3-(3-hydroxyphenyl)-1H-pyrazolo[3,4-d]pyrimidin-1-ylmethyl)-5-ethynyl-3-(3-(methylsulfonyl)benzyl)quinazolin-4(3H)-one;

3-((2-((4-Amino-3-(3-hydroxyphenyl)-1H-pyrazolo[3,4-d]pyrimidin-1-ylmethyl)-5-ethynyl-4-oxoquinazolin-3(4H)-yl)methyl)benzonitrile;

2-((4-Amino-3-(3-hydroxyphenyl)-1H-pyrazolo[3,4-d]pyrimidin-1-ylmethyl)-3-(4-chloro benzyl)-5-ethynylquinazolin-4(3H)-one;

2-((4-Amino-3-(3-hydroxyphenyl)-1H-pyrazolo[3,4-d]pyrimidin-1-ylmethyl)-3-(4-chloro benzyl)-5-(3-methoxyprop-1-ynyl)quinazolin-4(3H)-one;

2-((4-Amino-3-(4-hydroxyphenyl)-1H-pyrazolo[3,4-d]pyrimidin-1-yl)methyl)-3-(3-methoxy benzyl)-5-(3-methoxyprop-1-ynyl)quinazolin-4(3H)-one;

2-((4-Amino-3-(4-hydroxyphenyl)-1H-pyrazolo[3,4-d]pyrimidin-1-ylmethyl)-3-(2-chloro benzyl)-5-(3-methoxyprop-1-ynyl)quinazolin-4(3H)-one;

2-((4-Amino-3-(4-hydroxyphenyl)-1H-pyrazolo[3,4-d]pyrimidin-1-ylmethyl)-5-ethynyl-3-(4-(trifluoromethyl)benzyl)quinazolin-4(3H)-one;

2-((4-Amino-3-(3-hydroxyphenyl)-1H-pyrazolo[3,4-d]pyrimidin-1-ylmethyl)-3-(2-chloro benzyl)-5-(3-(2-methoxyethoxy)prop-1-ynyl)quinazolin-4(3H)-one;

2-((4-Amino-3-(3-hydroxyphenyl)-1H-pyrazolo[3,4-d]pyrimidin-1-ylmethyl)-5-ethynyl-3-((5-methylisoxazol-3-yl)methyl)quinazolin-4(3H)-one;

2-((4-Amino-3-(4-hydroxyphenyl)-1H-pyrazolo[3,4-d]pyrimidin-1-ylmethyl)-5-ethynyl-3-((5-methylisoxazol-3-yl-methyl)quinazolin-4(3H)-one;

2-((4-Amino-3-(4-hydroxyphenyl)-1H-pyrazolo[3,4-d]pyrimidin-1-yl)methyl)-3-(3-chloro-2-fluorobenzyl)-5-ethynylquinazolin-4(3H)-one;

2-((4-Amino-3-(4-hydroxyphenyl)-1H-pyrazolo[3,4-d]pyrimidin-1-ylmethyl)-3-(2,6-difluoro benzyl)-5-ethynylquinazolin-4(3H)-one;

2-((4-Amino-3-(4-hydroxyphenyl)-1H-pyrazolo[3,4-d]pyrimidin-1-ylmethyl)-3-(4-chloro-2-fluorobenzyl)-5-ethynylquinazolin-4(3H)-one;

2-((4-Amino-3-(3-fluoro-4-hydroxyphenyl)-1H-pyrazolo[3,4-d]pyrimidin-1-ylmethyl)-3-(2-chlorobenzyl)-5-ethynylquinazolin-4(3H)-one;

2-((4-Amino-3-(3-hydroxyphenyl)-1H-pyrazolo[3,4-d]pyrimidin-1-yl)methyl)-5-(3-methoxy prop-1-ynyl)-3-(3-(trifluoromethyl)benzyl)quinazolin-4(3H)-one;

2-((4-Amino-3-(4-hydroxyphenyl)-1H-pyrazolo[3,4-d]pyrimidin-1-ylmethyl)-5-ethynyl-3-(4-fluorobenzyl) quinazolin-4(3H)-one;

2-((4-Amino-3-(4-hydroxyphenyl)-1H-pyrazolo[3,4-d]pyrimidin-1-ylmethyl)-3-(2-chloro benzyl)-5-(3-cyclopentylprop-1-ynyl)quinazolin-4(3H)-one;

2-((4-Amino-3-(4-hydroxyphenyl)-1H-pyrazolo[3,4-d]pyrimidin-1-ylmethyl)-5-(3-(benzyloxy) prop-1-ynyl)-3-(2-chlorobenzyl)quinazolin-4(3H)-one;

2-((4-Amino-3-(4-hydroxyphenyl)-1H-pyrazolo[3,4-d]pyrimidin-1-ylmethyl)-3-(2-chloro benzyl)-5-(5-hydroxypent-1-ynyl)quinazolin-4(3H)-one;

2-((4-Amino-3-(4-hydroxyphenyl)-1H-pyrazolo[3,4-d]pyrimidin-1-ylmethyl)-5-ethynyl-3-(2-fluoro-5-methoxybenzyl)quinazolin-4(3H)-one;

2-((4-Amino-3-(4-hydroxyphenyl)-1H-pyrazolo[3,4-d]pyrimidin-1-yl)methyl)-3-(3,4-dichloro benzyl)-5-ethynylquinazolin-4(3H)-one;

2-((4-Amino-3-(4-hydroxyphenyl)-1H-pyrazolo[3,4-d]pyrimidin-1-ylmethyl)-3-benzyl-5-ethynylquinazolin-4(3H)-one;

2-((4-Amino-3-(4-hydroxyphenyl)-1H-pyrazolo[3,4-d]pyrimidin-1-ylmethyl)-5-ethynyl-3-(2-trifluoromethylbenzyl)quinazolin-4(3H)-one;

2-((4-Amino-3-(4-hydroxyphenyl)-1H-pyrazolo[3,4-d]pyrimidin-1-ylmethyl)-5-ethynyl-3-(4-methoxybenzyl)quinazolin-4(3H)-one;

4-((2-((4-Amino-3-(4-hydroxyphenyl)-1H-pyrazolo[3,4-d]pyrimidin-1-ylmethyl)-5-ethynyl-4-oxoquinazolin-3(4H)-ylmethyl)benzonitrile;

2-((4-Amino-3-(4-hydroxyphenyl)-1H-pyrazolo[3,4-d]pyrimidin-1-ylmethyl)-5-ethynyl-3-(2-fluoro-4-methoxybenzyl)quinazolin-4(3H)-one;

1-(3-(2-((4-Amino-3-(4-hydroxyphenyl)-1H-pyrazolo[3,4-d]pyrimidin-1-ylmethyl)-3-(2-chloro benzyl)-4-oxo-3,4-dihydroquinazolin-5-yl)prop-2-ynyl)urea;

2-((4-Amino-3-(3-hydroxyphenyl)-1H-pyrazolo[3,4-d]pyrimidin-1-ylmethyl)-3-(2-fluorobenzyl)-5-(3-(2-(2-methoxyethoxy)ethoxy)prop-1-ynyl)quinazolin-4(3H)-one;

2-((4-Amino-3-(4-fluoro-3-hydroxyphenyl)-1H-pyrazolo[3,4-d]pyrimidin-1-ylmethyl)-3-(2-chlorobenzyl)-5-ethynylquinazolin-4(3H)-one;

2-((4-Amino-3-(4-hydroxyphenyl)-1H-pyrazolo[3,4-d]pyrimidin-1-ylmethyl)-3-(2-chloro benzyl)-5-(3-phenoxyprop-1-ynyl)quinazolin-4(3H)-one;

2-((4-Amino-3-(4-hydroxyphenyl)-1H-pyrazolo[3,4-d]pyrimidin-1-ylmethyl)-3-(2-fluorobenzyl)-5-(6-morpholino-6-oxohex-1-yn-1-yl)quinazolin-4(3H)-one;

6-(2-((4-Amino-3-(3-hydroxyphenyl)-1H-pyrazolo[3,4-d]pyrimidin-1-yl)methyl)-3-(2-chloro benzyl)-4-oxo-3,4-dihydroquinazolin-5-yl)-N-(2-methoxyethyl)hex-5-ynamide;

2-((4-Amino-3-(3-hydroxyphenyl)-1H-pyrazolo[3,4-d]pyrimidin-1-yl)methyl)-3-(2-chloro benzyl)-5-(7-morpholino-7-oxohept-1-yn-1-yl)quinazolin-4(3H)-one;

2-((4-Amino-3-(3-hydroxyphenyl)-1H-pyrazolo[3,4-d]pyrimidin-1-yl)methyl)-3-(2-chloro benzyl)-5-(5-morpholino-5-oxopent-1-yn-1-yl)quinazolin-4(3H)-one;

2-((4-Amino-3-(3-hydroxyphenyl)-1H-pyrazolo[3,4-d]pyrimidin-1-yl)methyl)-3-((5-methyl pyrazin-2-yl)methyl)-5-(6-morpholino-6-oxohex-1-yn-1-yl)quinazolin-4(3H)-one;

2-((4-Amino-3-(4-hydroxyphenyl)-1H-pyrazolo[3,4-d]pyrimidin-1-yl)methyl)-3-(2-chloro benzyl)-5-(6-oxo-6-(piperidin-1-yl)hex-1-yn-1-yl)quinazolin-4(3H)-one;

6-(2-((4-Amino-3-(4-hydroxyphenyl)-1H-pyrazolo[3,4-d]pyrimidin-1-yl)methyl)-3-(2-chloro benzyl)-4-oxo-3,4-dihydroquinazolin-5-yl)-N,N-diethylhex-5-ynamide;

7-(2-((4-Amino-3-(3-hydroxyphenyl)-1H-pyrazolo[3,4-d]pyrimidin-1-yl)methyl)-3-(2-chloro benzyl)-4-oxo-3,4-dihydroquinazolin-5-yl)hept-6-ynoic acid;

2-Acetamido-N-(3-(2-((4-amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)prop-2-yn-1-yl)acetamide;

2-((4-Amino-3-(4-hydroxyphenyl)-1H-pyrazolo[3,4-d]pyrimidin-1-yl)methyl)-3-(3-methoxy-5-(trifluoromethyl)benzyl)-5-(6-morpholino-6-oxohex-1-yn-1-yl)quinazolin-4(3H)-one;

2-((4-Amino-3-(4-hydroxyphenyl)-1H-pyrazolo[3,4-d]pyrimidin-1-yl)methyl)-3-(2-methoxy phenethyl)-5-(6-morpholino-6-oxohex-1-yn-1-yl)quinazolin-4(3H)-one;

2-((4-Amino-3-(4-hydroxyphenyl)-1H-pyrazolo[3,4-d]pyrimidin-1-yl)methyl)-3-(benzo[b]thiophen-2-ylmethyl)-5-(6-morpholino-6-oxohex-1-yn-1-yl)quinazolin-4(3H)-one;

2-((4-Amino-3-(4-hydroxyphenyl)-1H-pyrazolo[3,4-d]pyrimidin-1-yl)methyl)-3-(2-fluoro-3-methoxybenzyl)-5-(6-morpholino-6-oxohex-1-yn-1-yl)quinazolin-4(3H)-one;

Methyl 3-((2-((4-amino-3-(3-hydroxyphenyl)-1H-pyrazolo[3,4-d]pyrimidin-1-yl)methyl)-5-(6-morpholino-6-oxohex-1-yn-1-yl)-4-oxoquinazolin-3(4H)-yl)methyl)benzoate;

2-((4-Amino-3-(3-hydroxyphenyl)-1H-pyrazolo[3,4-d]pyrimidin-1-yl)methyl)-3-((1-methyl-1H-pyrazol-4-yl)methyl)-5-(6-morpholino-6-oxohex-1-yn-1-yl)quinazolin-4(3H)-one;

2-((4-Amino-3-(3-hydroxyphenyl)-1H-pyrazolo[3,4-d]pyrimidin-1-yl)methyl)-3-(benzofuran-5-ylmethyl)-5-(6-morpholino-6-oxohex-1-yn-1-yl)quinazolin-4(3H)-one;

2-((4-Amino-3-(3-hydroxyphenyl)-1H-pyrazolo[3,4-d]pyrimidin-1-yl)methyl)-3-((2-methyl thiazol-4-yl)methyl)-5-(6-morpholino-6-oxohex-1-yn-1-yl)quinazolin-4(3H)-one;

2-((4-Amino-3-(3-hydroxyphenyl)-1H-pyrazolo[3,4-d]pyrimidin-1-yl)methyl)-3-(2-chloro benzyl)-5-(6-(4-methylpiperazin-1-yl)-6-oxohex-1-yn-1-yl)quinazolin-4(3H)-one;

2-((4-Amino-3-(3-hydroxyphenyl)-1H-pyrazolo[3,4-d]pyrimidin-1-yl)methyl)-3-(2-chloro benzyl)-5-(6-(4-morpholinopiperidin-1-yl)-6-oxohex-1-yn-1-yl)quinazolin-4(3H)-one;

5-(6-(4-Acetylpiperazin-1-yl)-6-oxohex-1-yn-1-yl)-2-((4-amino-3-(4-hydroxyphenyl)-1H-pyrazolo[3,4-d]pyrimidin-1-yl)methyl)-3-(2-chlorobenzyl)quinazolin-4(3H)-one;

N-(4-(2-((4-Amino-3-(3-hydroxyphenyl)-1H-pyrazolo[3,4-d]pyrimidin-1-yl)methyl)-3-(2-chloro benzyl)-4-oxo-3,4-dihydroquinazolin-5-yl)but-3-yn-1-yl)morpholine-4-carboxamide;

5-(6-(4-Acetylpiperazin-1-yl)-6-oxohex-1-yn-1-yl)-2-((4-amino-3-(4-hydroxyphenyl)-1H-pyrazolo[3,4-d]pyrimidin-1-yl)methyl)-3-(2-chlorobenzyl)quinazolin-4(3H)-one;

N-(4-(2-((4-Amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)but-3-yn-1-yl)morpholine-4-carboxamide;

2-((4-Amino-3-(4-hydroxyphenyl)-1H-pyrazolo[3,4-d]pyrimidin-1-yl)methyl)-5-(5-(bis(2-methoxyethyl)amino)pent-1-ynyl)-3-(2-chlorobenzyl)quinazolin-4(3H)-one;

6-(2-((4-Amino-3-(4-hydroxyphenyl)-1H-pyrazolo[3,4-d]pyrimidin-1-yl)methyl)-3-(2-chloro benzyl)-4-oxo-3,4-dihydroquinazolin-5-yl)-N-cyclopentylhex-5-ynamide;

6-(2-((4-Amino-3-(4-hydroxyphenyl)-1H-pyrazolo[3,4-d]pyrimidin-1-ylmethyl)-3-(2-chloro benzyl)-4-oxo-3,4-dihydroquinazolin-5-yl)-N-(tetrahydro-2H-pyran-4-yl)hex-5-ynamide;

6-(2-((4-Amino-3-(4-hydroxyphenyl)-1H-pyrazolo[3,4-d]pyrimidin-1-ylmethyl)-3-(2-chloro benzyl)-4-oxo-3,4-dihydroquinazolin-5-yl)-N-(2-morpholinoethyl)hex-5-ynamide;

2-((4-Amino-3-(4-hydroxyphenyl)-1H-pyrazolo[3,4-d]pyrimidin-1-ylmethyl)-3-(2-chloro benzyl)-5-(6-(4-(2-methoxyethyl)piperazin-1-yl)-6-oxohex-1-ynyl)quinazolin-4(3H)-one;

6-(2-((4-Amino-3-(4-hydroxyphenyl)-1H-pyrazolo[3,4-d]pyrimidin-1-ylmethyl)-3-(2-chloro benzyl)-4-oxo-3,4-dihydroquinazolin-5-yl)-N-(2-(dimethylamino)ethyl)hex-5-ynamide;

6-(2-((4-Amino-3-(4-hydroxyphenyl)-1H-pyrazolo[3,4-d]pyrimidin-1-ylmethyl)-3-(2-chloro benzyl)-4-oxo-3,4-dihydroquinazolin-5-yl)-N-(pyridin-4-yl)hex-5-ynamide;

6-(2-((4-Amino-3-(3-hydroxyphenyl)-1H-pyrazolo[3,4-d]pyrimidin-1-ylmethyl)-3-(2-chloro benzyl)-4-oxo-3,4-dihydroquinazolin-5-yl)-N-(pyridin-4-yl)hex-5-ynamide;

2-((4-Amino-3-(4-hydroxyphenyl)-1H-pyrazolo[3,4-d]pyrimidin-1-ylmethyl)-3-(2-chloro benzyl)-5-(6-(4-(dimethylamino)piperidin-1-yl)-6-oxohex-1-ynyl)quinazolin-4(3H)-one;

6-(2-((4-Amino-3-(4-hydroxyphenyl)-1H-pyrazolo[3,4-d]pyrimidin-1-ylmethyl)-3-(2-chloro benzyl)-4-oxo-3,4-dihydroquinazolin-5-yl)-N,N-bis(2-methoxyethyl)hex-5-ynamide;

6-(2-((4-Amino-3-(3-hydroxyphenyl)-1H-pyrazolo[3,4-d]pyrimidin-1-ylmethyl)-3-(2-chloro benzyl)-4-oxo-3,4-dihydroquinazolin-5-yl)-N,N-bis(2-methoxyethyl)hex-5-ynamide;

6-(2-((4-Amino-3-(4-hydroxyphenyl)-1H-pyrazolo[3,4-d]pyrimidin-1-ylmethyl)-3-(2-chloro benzyl)-4-oxo-3,4-dihydroquinazolin-5-yl)-N-(2-(4-methylpiperazin-1-yl)ethyl)hex-5-ynamide;

6-(2-((4-Amino-3-(4-hydroxyphenyl)-1H-pyrazolo[3,4-d]pyrimidin-1-ylmethyl)-3-(2-chloro benzyl)-4-oxo-3,4-dihydroquinazolin-5-yl)-N-methyl-N-(2-(4-methylpiperazin-1-yl)ethyl)hex-5-ynamide;

6-(2-((4-Amino-3-(4-hydroxyphenyl)-1H-pyrazolo[3,4-d]pyrimidin-1-ylmethyl)-3-(2-chloro benzyl)-4-oxo-3,4-dihydroquinazolin-5-yl)-N-isopropylhex-5-ynamide;

6-(2-((4-Amino-3-(3-hydroxyphenyl)-1H-pyrazolo[3,4-d]pyrimidin-1-ylmethyl)-3-(2-chloro benzyl)-4-oxo-3,4-dihydroquinazolin-5-yl)-N-isopropylhex-5-ynamide;

6-(2-((4-Amino-3-(4-hydroxyphenyl)-1H-pyrazolo[3,4-d]pyrimidin-1-ylmethyl)-3-(2-chloro benzyl)-4-oxo-3,4-dihydroquinazolin-5-yl)-N,N-dimethylhex-5-ynamide;

2-((4-Amino-3-(4-hydroxyphenyl)-1H-pyrazolo[3,4-d]pyrimidin-1-yl)methyl)-3-(2-chloro benzyl)-5-(6-oxo-6-(pyrrolidin-1-yl)hex-1-yn-1-yl)quinazolin-4(3H)-one;

6-(2-((4-Amino-3-(4-hydroxyphenyl)-1H-pyrazolo[3,4-d]pyrimidin-1-ylmethyl)-3-(2-chloro benzyl)-4-oxo-3,4-dihydroquinazolin-5-yl)-N-(pyrrolidin-3-yl)hex-5-ynamide;

2-((4-Amino-3-(4-hydroxyphenyl)-1H-pyrazolo[3,4-d]pyrimidin-1-yl)methyl)-3-(2-chloro benzyl)-5-(6-(3-(dimethylamino)pyrrolidin-1-yl)-6-oxohex-1-ynyl)quinazolin-4(3H)-one;

2-((4-Amino-3-(3-hydroxyphenyl)-1H-pyrazolo[3,4-d]pyrimidin-1-yl)methyl)-3-(2-chloro benzyl)-5-(6-(3-(dimethylamino)pyrrolidin-1-yl)-6-oxohex-1-ynyl)quinazolin-4(3H)-one;

2-((4-Amino-3-(4-hydroxyphenyl)-1H-pyrazolo[3,4-d]pyrimidin-1-yl)methyl)-3-(2-chloro benzyl)-5-(6-(4-methyl-1,4-diazepan-1-yl)-6-oxohex-1-ynyl)quinazolin-4(3H)-one, 2-((4-Amino-3-(3-hydroxyphenyl)-1H-pyrazolo[3,4-d]pyrimidin-1-yl)methyl)-3-(2-chloro benzyl)-5-(6-(4-methyl-1,4-diazepan-1-yl)-6-oxohex-1-ynyl)quinazolin-4(3H)-one, 2-((4-Amino-3-(4-hydroxy-3-methoxyphenyl)-1H-pyrazolo[3,4-d]pyrimidin-1-yl)methyl)-3-(2-chlorobenzyl)-5-(6-morpholino-6-oxohex-1-ynyl)quinazolin-4(3H)-one or a pharmaceutically acceptable salt thereof, including all stereoisomers, tautomers and isotopic derivatives thereof.

Compounds of formula (I) can be prepared by a process comprising reacting compounds of formula (II):

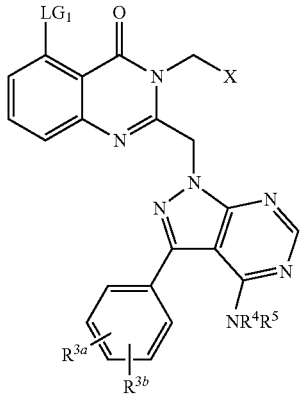

(II)

or a protected derivate thereof wherein X, $R^{3a}$, $R^{3b}$, $R^4$ and $R^5$ are as defined above for compounds of formula (I) and $LG_1$ represents a leaving group such as halo, in particular bromo, with a compound of formula (III):

=$R^1$ (III)

or a protected derivative thereof, wherein $R^1$ is as defined above for compounds of formula (I), in the presence of a suitable catalyst, an organic base and a polar aprotic solvent, under an inert atmosphere; and optionally deprotecting to reveal a compound of formula (I); and optionally converting one compound of formula (I) into another compound of formula (I) by standard functional group transformations.

Suitable catalysts include palladium catalysts such as bis (triphenylphosphine)palladium (II) dichloride, in the presence of copper iodide.

A suitable polar aprotic solvent is DMF.

A suitable inert atmosphere is nitrogen.

The reaction may be performed employing irradiation, for example using microwave irradiation at 120° C. and a power setting of 200 W.

The deprotection, to reveal a compound of formula (I) where, for example $R^1$ is H, and the protective group is a silyl group can be effected by treatment with a reagent such as tetrabutylammonium chloride in the presence of a polar aprotic solvent such as DMF. The reaction may be performed at a reduced temperature, such as about 0° C.

Compounds of formula (I) wherein $R^1$ comprises a carboxylic acid moiety can be converted to other compounds of formula (I) by routine techniques, for example amide couplings.

Further examples of converting a compound of formula (I) into other compounds of formula (I) are provided by those compounds of formula (I) wherein $R^1$ comprises a primary alcohol. Such compounds may be transformed into compounds of formula (I) wherein $R^1$ comprises a primary alkyl halide, and then, by subsequent reaction with a primary or secondary amine, into a compound of formula (I) wherein $R^1$ comprises an alkyl amine.

Compounds of formula (II) can be prepared by reacting a compound of formula (IV):

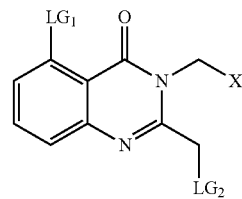

(IV)

or a protected derivative thereof, wherein $LG_1$ and X are as defined above for compounds of formula (II) and $LG_2$ is a leaving group, for example halo, such as chloro, with a compound of formula (V):

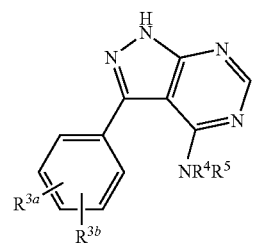

(V)

or a protected derivative thereof, wherein $R^{3a}$, $R^{3b}$, $R^4$ and $R^5$ are as defined above for compounds of formula (I), in the presence of a base, in a polar aprotic solvent.

Suitable protecting groups for compounds of formula (V) in which $R^{3a}$ is hydroxyl include a tertbutyldimethylsilylether.

Suitable bases include potassium carbonate.

A suitable polar aprotic solvent is DMF.

Alternatively compounds of formula (II) can be prepared by reacting a compound of formula (VI):

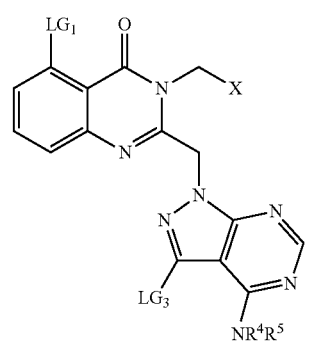

(VI)

or a protected derivative thereof, wherein $LG_1$, X, $R^4$ and $R^5$ are as defined above for compounds of formula (II) and $LG_3$ represents a leaving group such as halo, in particular iodo, with a compound of formula (VII):

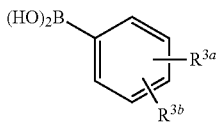
(VII)

or a protected derivate thereof, wherein $R^{3a}$ and $R^{3b}$ are as defined above for compounds of formula (I), in the presence of a suitable noble metal catalyst, an inorganic base and a polar protic solvent, under an inert atmosphere; followed, where appropriate, by deprotection of the groups $R^{3a}$ and/or $R^{3b}$, and/or X.

A suitable catalyst is tetrakis(triphenylphosphine)palladium(0).

A suitable inorganic base is sodium carbonate.

A suitable polar protic solvent is ethanol.

The reaction may be performed at an elevated temperature, for example at 85° C. for several days for example 3 days before cooling to RT.

Compounds of formula (VI) can be prepared by reacting a compound of formula (IV) or a protected derivative thereof, wherein $LG_1$ $LG_2$ and X are as defined above with a compound of formula (VIII):

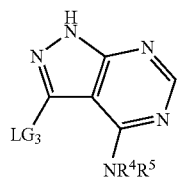
(VIII)

or a protected derivative thereof, wherein $R^4$ and $R^5$ are as defined above for compounds of formula (I) and $LG_3$ is a leaving group, for example a halogen atom, in particular an iodo substituent. The reaction is conveniently conducted in a polar aprotic solvent and in the presence of an inorganic base at ambient temperature, such as RT and in the dark.

A suitable inorganic base is sodium carbonate.

A suitable polar aprotic solvent is DMF.

Compounds of formula (V) wherein $R^{3a}$, $R^{3b}$, $R^4$ and $R^5$ are as defined above, may be prepared by reacting a compound of formula (VIII) wherein $LG_3$, $R^4$ and $R^5$ are as defined above with a compound of formula (VII) or a protected derivate thereof, wherein $R^{3a}$ and $R^{3b}$ are as defined above for compounds of formula (I):

Compounds of formula (IV) may be prepared by reacting a compound of formula (IX):

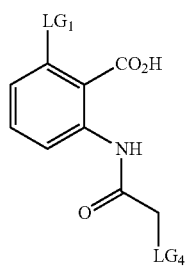
(IX)

or a protected derivative thereof wherein $LG_1$ is as defined above for compounds of formula (II) and $LG_4$ is a leaving group, for example halo, such as chloro, or hydroxy with a compound of formula (X):

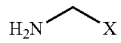
(X)

such as

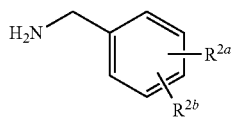
(Xa)

or a protected derivative thereof, wherein X, $R^{2a}$ and $R^{2b}$ are as defined above for compounds of formula (II), in the presence of a suitable reagent, such as a phosphorus trihalide, an organic base and a non-polar solvent.

A suitable phosphorus trihalide is phosphorus trichloride.

A suitable non-polar solvent is toluene.

A suitable organic base is triethylamine.

Protection of the hydroxyl may, for example, be effected using TBDMSCl in a suitable solvent, for example DMF in the presence of a suitable base such as imidazole.

Compounds of formula (IX) may be prepared by reacting a compound of formula (XI):

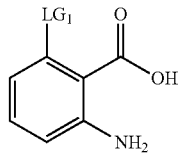
(XI)

or a protected derivative thereof, wherein $LG_1$ is as defined above for compounds of formula (II) with a compound of formula (XII):

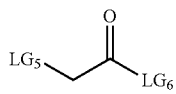
(XII)

wherein $LG_5$ and $LG_6$ are leaving groups, for example halo, such as chloro in presence of a suitable solvent and a suitable base.

A suitable solvent is toluene and a suitable base is pyridine.

Protecting groups may be required to protect chemically sensitive groups during one or more of the reactions described above, to ensure that the process is efficient. Thus if desired or necessary, intermediate compounds may be protected by the use of conventional protecting groups. Protecting groups and means for their removal are described in "Protective Groups in Organic Synthesis", by Theodora W. Greene and Peter G. M. Wuts, published by John Wiley & Sons Inc; 4th Rev Ed., 2006, ISBN-10: 0471697540.

Novel intermediates are claimed as an aspect of the invention.

The compounds of formulae (III), (VII), (VIII), (X) and (XI) and (XII) as defined above, are either commercially available or can be readily prepared from commercially available starting materials, using routine published techniques (see for example Table 1).

A selection of the compounds of formula (I), disclosed herein, have been screened by chiral stationary phase HPLC for the presence of non interconverting rotational isomers, otherwise known as atropisomers. Atropisomerism results from hindered rotation about a single bond where the torsional energy barrier to free rotation is sufficiently high to significantly slow the interconversion of non-superimposable conformers. The analytical and preparative methods disclosed below have been used to resolve the discrete atropisomers of a number of published PI3K inhibitors, revealing that they ordinarily occur as mixtures of stereoisomers possessing very long half-lives (months or years) under physiological conditions. (See experimental section for details). The occurrence of atropisomerism represents an added burden of complexity to the development of such compounds as therapeutic agents, since discrete stereoisomers are usually highly preferred over mixtures, such as racemates. Analysis of selected examples using the chromatographic methods disclosed herein have revealed no evidence that the compounds of formula (I) exhibit atropisomerism. In the absence of additional features that are well known to give rise to stereoisomers, for example a stereogenic centre, the current disclosure provides for compounds that advantageously exist as single discrete molecular entities. Thus the compounds of the present disclosure are particularly useful as therapeutically active agents in pharmaceutical compositions and in treatment.

In one aspect the compounds are useful in treatment, for example COPD and/or asthma.

The PI3K compounds developed to date have typically been intended for oral administration. Typically this strategy involves the optimisation of a compound's pharmacokinetic profile in order to achieve an adequate duration of action. In this way a sufficiently high drug concentration is established and maintained between doses to provide continuous clinical benefit. An inevitable and frequently undesired consequence of this approach is that non-targeted body tissues, especially the liver and the gut, are likely to be exposed to pharmacologically active concentrations of the drug.

An alternative strategy is to design treatment regimens in which the drug is dosed directly to the inflamed organ (for example topical therapy). Although this approach is not suitable for treating all chronic inflammatory conditions, it has been extensively exploited in treating lung diseases (asthma, COPD), skin lesions (atopic dermatitis and psoriasis), nasal diseases (allergic rhinitis) and gastrointestinal disorders (ulcerative colitis).

In topical therapy, the desired efficacy can sometimes be achieved by ensuring that the drug has a sustained duration of action and is retained predominantly in the target organ, thereby minimising the risks of systemic toxicity. Alternatively an appropriate formulation can be used which generates a "reservoir" of the active drug which is then available to sustain the desired effects. The first approach is exemplified in the use of the anticholinergic drug tiotropium bromide (Spiriva HandiHaler®), which is administered topically to the lung as a treatment for COPD. This compound has an exceptionally high affinity for its target receptor resulting in a very slow off rate (dissociation rate) and a consequent sustained duration of action.

There is provided according to one aspect of the present disclosure use of a compound of formulation as a PI3 kinase inhibitor, for example administered topically to the lung.

In one aspect of the disclosure the compounds herein are particularly suitable for topical delivery, such as topical delivery to the lungs, in particular for the treatment of COPD.

Thus in one aspect there is provided use of compounds of formula (I) for the treatment of COPD and/or asthma, in particular COPD or severe asthma, by inhalation i.e. topical administration to the lung. Advantageously, administration to the lung allows the beneficial effects of the compounds to be realised whilst minimising the side-effects, for patients.

In one embodiment the compounds are suitable for sensitizing patients to treatment with a corticosteroid.

The compounds herein may also be useful for the treatment of rheumatoid arthritis.

Further, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration, and may be different depending on the route of administration.

In one embodiment compositions may be prepared e.g. for parenteral, subcutaneous, intramuscular, intravenous, intraarticular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985).

Formulations for parenteral administration may contain as excipients sterile water or saline, alkylene glycols such as propylene glycol, polyalkylene glycols such as polyethylene glycol, oils of vegetable origin, hydrogenated naphthalenes and the like.

Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably the compound of formula (I) is administered topically to the lung. Hence in one embodiment there is provided a pharmaceutical composition comprising a compound of the disclosure optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean diameter (MMAD) of 1-10 μm. The formulation will typically contain a topically acceptable diluent such as lactose, usually of large particle size e.g. a mass mean diameter (MMAD) of 100 μm or more. Example dry powder delivery systems include SPINHALER, DISKHALER, TURBOHALER, DISKUS, SKYEHALER, ACCUHALER and CLICKHALER.

In one embodiment a compound of the present is provided as a micronized dry powder formulation, for example comprising lactose of a suitable grade, filled into a device such as DISKUS.

Compounds according to the disclosure are intended to have therapeutic activity. In a further aspect, the present invention provides a compound of the disclosure for use as a medicament.

Compounds according to the disclosure may also be useful in the treatment of respiratory disorders including COPD (including chronic bronchitis and emphysema), asthma, paediatric asthma, cystic fibrosis, sarcoidosis, idiopathic pulmonary fibrosis, allergic rhinitis, rhinitis, sinusitis, especially asthma, chronic bronchitis and COPD.

Compounds of the disclosure may also re-sensitise the patient's condition to treatment with a corticosteroid, when the patient's condition has become refractory to the same.

One or more compounds of the disclosure may exhibit anti-viral activity and prove useful in the treatment of viral exacerbations of asthma and/or COPD.

The compounds of the present disclosure may also be useful in the prophylaxis, treatment or amelioration of flu virus, rhinovirus and/or respiratory syncytical virus.

Compounds according to the disclosure are also expected to be useful in the treatment of certain conditions which may be treated by topical or local therapy including allergic conjunctivitis, conjunctivitis, allergic dermatitis, contact dermatitis, psoriasis, ulcerative colitis, inflamed joints secondary to rheumatoid arthritis or osteoarthritis.

In one embodiment the compounds of formula (I) are thought to be useful in the, treatment of Hepatitis C and/or HIV, when administered by an appropriate route. Appropriate routes of administration may include oral, intravenous injection or infusion.

In one embodiment a compound of formula (I) for the treatment of Hepatitis C is delivered to the blood pre-entry to the liver.

Compounds of the disclosure are also expected to be useful in the treatment of certain other conditions including rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

Thus, in a further aspect, the present invention provides a compound as described herein for use in the treatment of one or more of the above mentioned conditions.

In a further aspect, the present invention provides use of a compound as described herein for the manufacture of a medicament for the treatment of one or more of the above mentioned conditions.

In a further aspect, the present invention provides a method of treatment of the above mentioned conditions which comprises administering to a subject an effective amount of a compound of the disclosure or a pharmaceutical composition thereof.

Compounds described herein may also be used in the manufacture of a medicament for the treatment of one or more of the above-identified diseases.

The word "treatment" is intended to embrace prophylaxis as well as therapeutic treatment.

A compound of the disclosure may also be administered in combination with one or more other active ingredients e.g. active ingredients suitable for treating the above mentioned conditions. For example possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol, indacaterol) and/or xanthines (e.g. theophylline), musacarinic antagonists, (e.g. ipratropium) and/or a p38 MAP kinase inhibitor.

In one embodiment a compound of the disclosure is administered in combination with an antiviral agent, for example acyclovir, tamiflu, relenza or interferon.

In one embodiment the combination of active ingredients are co-formulated.

In one embodiment the combination of active ingredients is simply co-administered.

EXPERIMENTAL SECTION

Abbreviations

Abbreviations used herein have the meanings defined in the table below. Any abbreviations appearing in the text which have not been defined are intended to covey their generally accepted meaning.

AcOH glacial acetic acid
Aq aqueous
Ac Acetyl
ATP adenosine-5'-triphosphate
BALF bronchoalveolae lavage fluid
Boc tert-butoxycarbonyl
Br Broad
BSA bovine serum albumin
CDI 1,1-carbonyl-diimidazole
COPD chronic obstructive pulmonary disease
D Doublet
DCM dichloromethane
DIAD diisopropylazadicarboxylate
DIBAL-H diisobutylaluminium hydride
DIPEA N,N-diisopropylethylamine
DMF N,N-dimethylformamide
DMSO dimethyl sulfoxide
dppf 1,1'-bis(diphenylphosphino)ferrocene
EDC 1-ethyl-3-(3-dimethylaminopropyl)carbodiimide
(ES$^+$) electrospray ionization, positive mode
Et Ethyl
Et$_2$O diethyl ether
Et$_3$N triethylamine
EtOH Ethanol
EtOAc ethyl acetate
FACS fluorescence-activated cell sorting
FCS foetal calf serum
G gram(s)
HOBt 1-hydroxybenzotriazole
HPLC high performance liquid chromatography
HPLC-MS high performance liquid chromatography mass spectrometry
Hr hour(s)
HRP horseradish peroxidase
i-n intra-nasal
i-t intra-tracheal
KHMDS potassium hexamethyldisilazane
μL microliter(s)
LPS lipopolysaccharide
μM micromolar
Mm micro meter
M Molar
(M+H)$^+$ protonated molecular ion
Me Methyl
MeOH methanol
MeOD deuterated methanol
Mg milligram(s)
MHz megahertz
Min minute(s)
mL milliliter(s)
mM millimolar
Mm millimeter
mmol millimole(s)
MTT 3-(4,5-dimethylthiazol-2-yl)-2,5-diphenyltetrazolium bromide
m/z mass-to-charge ratio
Ng nanogram
Nm nanomolar
Nm nanometer
NMP 1-methylpyrrolidin-2-one (N-methyl-2-pyrrolidone)
NMR nuclear magnetic resonance (spectroscopy)
PBS phosphate buffered saline
Pd$_2$(dba)$_3$ tris(dibenzylideneacetone)dipalladium(0)
Ph Phenyl
PIP2 phosphatidylinositol 4,5-biphosphate
PIP3 phosphatidylinositol 3,4,5-triphosphate
PMA phorbol myristate acetate
Po by oral administration
PPh$_3$ triphenylphosphine
PyBOP® (benzotriazol-1-yloxy)tripyrrolidinophosphonium hexafluorophosphate
Q Quartet
Quin Quintet
R$^t$ retention time
RT room temperature
RP HPLC reverse phase high performance liquid chromatography
S Singlet
SCX solid supported cation exchange (resin)
SDS sodium dodecyl sulfate
T Triplet
TBAF tetrabutylammonium fluoride
TBDMSCl tert-butyldimethylsilyl chloride
TFA trifluoroacetic acid
THF tetrahydrofuran
TLC thin-layer chromatography
TMB 3,3",5,5"-tetramethylbenzidine
TNFα tumour necrosis factor alpha
TR-FRET time-resolved fluorescence resonance energy transfer
Vol Volume
VT Variable temperature
W Watts General Procedures Those intermediates and bespoke chemical building blocks not available from commercial sources were prepared according to the procedures disclosed herein or using the cited literature methods. All other starting materials and solvents (HPLC grade) were obtained from commercial sources and were used without further purification Where indicated reactions were degassed by passing a stream of nitrogen through them for at least 10 min. Microwave reactions were carried out using a CEM Discover or Explorer focussed microwaves apparatus. Organic solutions were dried using magnesium sulphate or sodium sulphate. Flash column chromatography was performed using a minimum of 20 mass equivalents of silica with SiliCycle SiliaFlash® P60 (230-400 mesh) or a Biotage Isolute SPE Column prepacked with Flash Si II.

Analytical Methods

Thin-layer chromatography (TLC) analysis was performed with Kieselgel 60 with fluorescence indicator UV$_{254}$ plates and visualized using UV light or stained with standard TLC dips or iodine.

Reverse Phase Analytical High Performance Liquid Chromatography-Mass Spectrometry:

All samples were routinely analysed by HPLC-MS using the instrumentation and conditions described below. Unless stated otherwise final compound were subject to analysis using Method B and intermediates were analysed utilising Method A.

Method A was performed on Agilent HP1100 and Shimadzu 2010, systems using reverse phase Atlantis dC18 columns (5 μm, 2.1×50 mm), gradient 5-100% B (A=water/0.1% formic acid, B=acetonitrile/0.1% formic acid) over 3 min, injection volume 3 μL, flow=1.0 mL/min. UV spectra were recorded at 215 nm using a Waters 2487 dual wavelength UV detector or the Shimadzu 2010 system. Mass spectra were obtained over the range m/z 150 to 850 at a sampling rate of 2 scans per second using Waters ZMD or over m/z 100 to 1000 at a sampling rate of 2 Hz using electrospray ionisation, by a Shimadzu 2010 LC-MS system.

Method B was performed on Agilent HP1100 and Shimadzu 2010, systems using reverse phase Water Atlantis dC18 columns (3 μm, 2.1×100 mm), gradient 5-100% B (A=water/0.1% formic acid, B=acetonitrile/0.1% formic acid) over 7 min, injection volume 3 μL, flow=0.6 mL/min. UV spectra were recorded at 215 nm using a Waters 2996 photo diode array or on the Shimadzu 2010 system. Mass spectra were obtained over the range m/z 150 to 850 at a sampling rate of 2 scans per second using Waters ZQ or over m/z 100 to 1000 at a sampling rate of 2 Hz using electrospray ionisation, by a Shimadzu 2010 LC-MS system.

Method C was performed on Agilent HP1100, systems using reverse phase Phenomenex Gemini dC18 columns (3 μm, 2.0×50 mm), gradient 1-100% B (A=2 mM ammonium bicarbonate pH10, B=acetonitrile) over 3.5 min, injection volume 3 μL, flow=1.0 mL/min. UV spectra were recorded at 215 nm using a Waters 2487 dual wavelength UV detector or a Waters 2996 photo diode array. Mass spectra were obtained over the range m/z 150 to 850 at a sampling rate of 2 scans per second using Waters ZMD or a Waters ZQ.

Method D: was performed on Agilent HP1200, systems using Agilent Extend C18 columns, (1.8 μm, 4.6×30 mm) at 40° C. and a flow rate of 2.5-4.5 mL min$^{-1}$, eluting with a H$_2$O-MeCN gradient containing 0.1% v/v formic acid over 4 min. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL·min$^{-1}$; 3.01-3.50 min, held at 5% H$_2$O-95% MeCN; 3.50-3.60 min, returned to 95% H$_2$O-5% MeCN; flow rate reduced to 3.50 mL min$^{-1}$; 3.60-3.90 min, held at 95% H$_2$O-5% MeCN; 3.90-4.00 min, held at 95% H$_2$O-5% MeCN, flow rate reduced to 2.5 mL·min$^{-1}$. UV detection was performed at 254 nm using an Agilent G1314B variable wavelength detector. Mass spectra were obtained over the range m/z 60 to 2000 at a sampling rate of 1.6 sec/cycle using an Agilent G1956B.

Chiral Stationary Phase Analytical HPLC was performed using Daicel columns (5 μm×5 cm×4.6 mm) containing one of the following stationary phases: Chiralpak AD-H, Chiralcel OD-H, Chiralcel OJ-H, and Chiralpak AS-H. A flow rate of 1 mL/min, was used eluting under isocratic conditions over 6 to 20 min, with one of the following mobile phases: 70:30 heptane:IPA (v/v), 85:15 heptane:EtOH (v/v), 50:50 MeOH:EtOH (v/v), and acetonitrile; employing UV detection at 254 nm. Each of these mobile phase are compatible with the column packings referred to above, providing sixteen different solvent and stationary phase permutations. Modifiers such as triethylamine (0.1%), formic acid (0.1%) may be added to improve the resolution Semi-preparative Chiral Stationary Phase LC-UV was performed on a Gilson preparative modular system using a Daicel Chiralpak AD semi-prep column (10 mm, 20×250 mm) and a flow rate of 18 mL/min eluting with an isocratic method over 20 min using 70:20 heptane:IPA and 0.1% triethylamine employing an injection volume of 1.0 mL. UV spectra were recorded and fractions analysed for collection at 215 nm with a Gilson 119 UV detector.

Data were integrated and reported using OpenLynx and OpenLynx Browser software or via Shimadzu PsiPort software.

$^1$H NMR Spectroscopy: spectra were acquired on a either a Bruker DPX 250 MHz, a Bruker Avance III 400 MHz or a Bruker DRX 500 MHz spectrometer using residual protonated resonances of the deuterated solvent as the internal reference Preparation of Non Commercial Intermediates 3-(3-(tert-Butyldimethylsilyloxy)phenyl)-1H-pyrazolo[3,4-d]pyrimidin-4-amine (3)

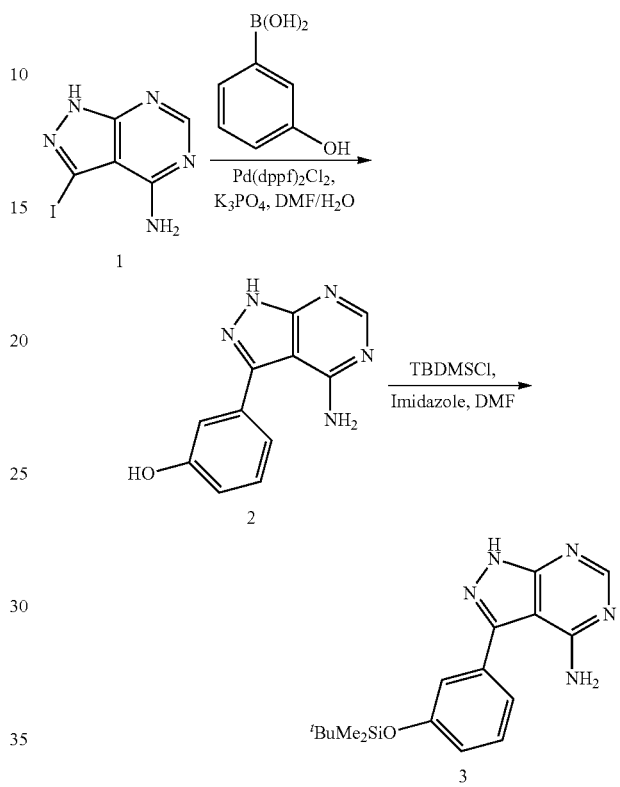

To a stirred suspension of 3-iodo-1H-pyrazolo[3,4-d]pyrimidin-4-amine (1) (8.22 g, 31.5 mmol), 3-phenol boronic acid (13.0 g, 94.5 mmol) and potassium phosphate (10.0 g, 47.3 mmol) in degassed DMF/water (3:2, 140 mL) was added [dppf] palladium (II) dichloride (13.0 g, 15.7 mmol). The reaction mixture was flushed with nitrogen, heated at 120° C. for 2 hr and then allowed to cool to RT. The reaction mixture was diluted with EtOAc (500 mL) and aqueous hydrochloric acid (2 M, 500 mL) and the resulting suspension was filtered. The filtrate was extracted with aqueous hydrochloric acid (2 M, 2×500 mL). The combined aqueous extracts were basified with a saturated aq solution of sodium carbonate to pH 10. The precipitate formed was filtered and the filtrate was extracted with EtOAc (3×1 L). The combined organic extracts were dried, filtered and the solvent removed in vacuo to afford a grey solid. All solid materials generated during the workup procedure were combined and triturated with DCM to afford 3-(4-amino-1H-pyrazolo[3,4-d]pyrimidin-3-yl)phenol (2) (6.04 g, 84%) as a grey solid: m/z 228 (M+H)$^+$ (ES$^+$).

To a stirred solution of compound (2) (4.69 g, 20.66 mmol) and imidazole (2.10 g, 30.99 mmol) in dry DMF (100 mL) was added TBDMSCl (4.70 g, 30.99 mmol). After 16 hr, further aliquots of imidazole (2.10 g, 30.99 mmol) and TBDMSCl (4.70 g, 30.99 mmol) were added and the mixture was stirred for 48 hr. The reaction mixture was diluted with water (120 mL) and extracted with DCM (2×200 mL). The combined organic extracts were washed with water (2×200 mL), dried, filtered and the volume reduced to approximately 100 mL by evaporation in vacuo. The resulting slurry was filtered and the solid washed with heptane (50 mL) to afford the title compound (3) (6.05 g, 85%) as an off-white solid: m/z 343 (M+H)$^+$ (ES$^+$).

3-(4-(tert-Butyldimethylsilyloxy)phenyl)-1H-pyrazolo[3,4-d]pyrimidin-4-amine (5)

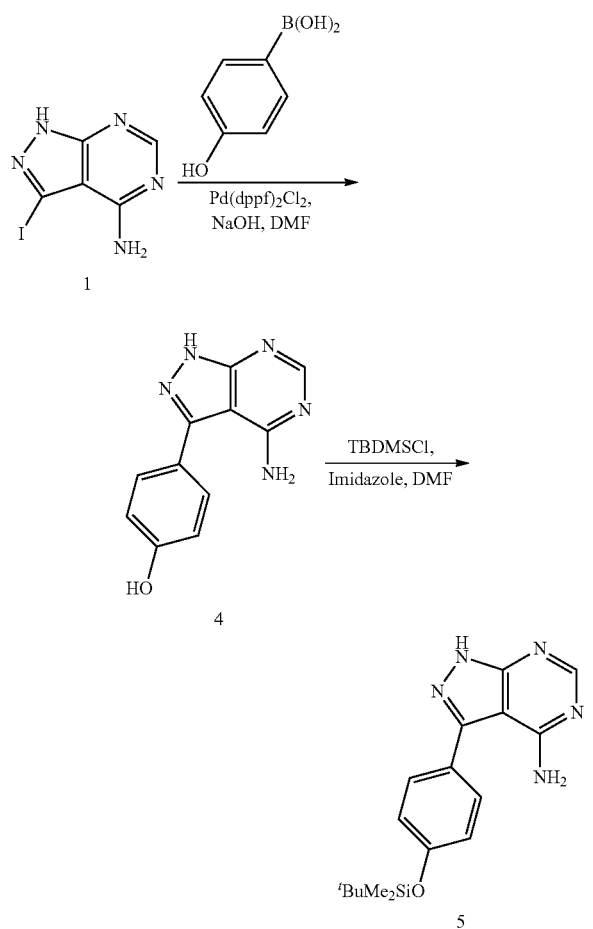

To a stirred suspension of 3-iodo-1H-pyrazolo[3,4-d]pyrimidin-4-amine (1) (10.0 g, 38.4 mmol), [dppf] palladium (II) dichloride (1.37 g, 1.92 mmol) and 4-phenol boronic acid (15.8 g, 115.2 mmol) in DMF (90 mL) was added aq sodium hydroxide (1 M, 76.0 mL, 76.8 mmol). The reaction was flushed with nitrogen and heated at 120° C. for 18 hr. The reaction mixture was allowed to cool to RT and diluted with water (200 mL). The resulting precipitate was collected by filtration and washed with water (200 mL) and then DCM, until the filtrate ran colourless, to afford 4-(4-amino-1H-pyrazolo[3,4-d]pyrimidin-3-yl)phenol (4) (5.25 g, 60%) as a brown solid: m/z 228 (M+H)$^+$ (ES$^+$).

To a stirred solution of compound (4) (5.25 g, 23.1 mmol) and imidazole (3.85 g, 57.8 mmol) in dry DMF (70 mL) was added TBDMSCl (4.19 g, 27.7 mmol). After 16 hr, further aliquots of imidazole (1.93 g, 28.9 mmol) and TBDMSCl (2.10 g, 13.9 mmol) were added and the mixture stirred for 4 hr. The reaction mixture was diluted with water (200 mL) and the resulting precipitate was collected by filtration, washed with water (200 mL) and heptane (300 mL) to afford the title compound (5) (7.31 g, 93%) as a brown solid: m/z 344 (M+H)$^+$ (ES$^+$).

5-bromo-3-(2-chlorobenzyl)-2-(chloromethyl)quinazolin-4(3H)-one (8)

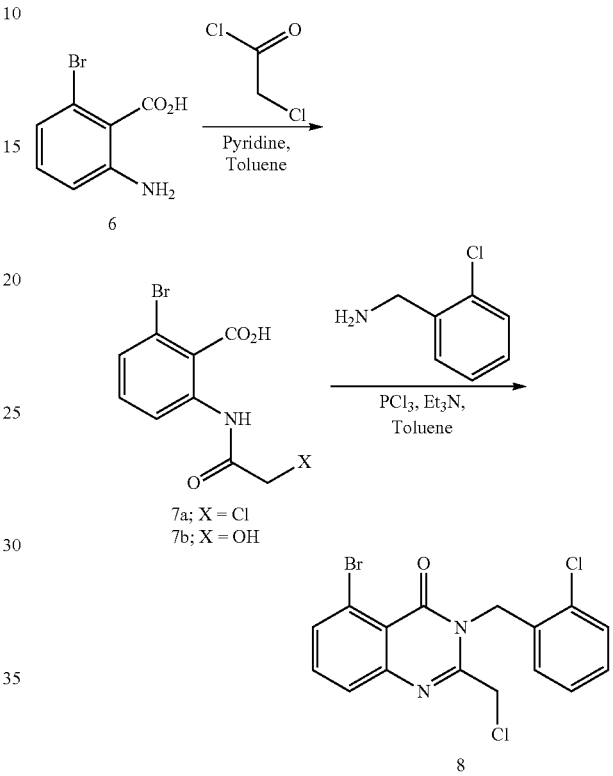

To a stirred solution of 2-amino-6-bromo-benzoic acid (6) (3.06 g, 14.2 mmol) in toluene (75 mL) cooled to 0° C. in an ice-bath was added pyridine (0.60 mL, 7.10 mmol) followed by a solution of chloroacetyl chloride (2.26 mL, 28.4 mmol) in toluene (75 mL) drop-wise over 1 hr. The reaction mixture was allowed to warm to RT, and was heated at 115° C. for 3 hr and then allowed to cool to RT. The solvent volume was reduced by half by evaporation in vacuo. Upon standing overnight, the product precipitated and was collected by filtration to afford 2-bromo-6-(2-chloroacetamido)benzoic acid (7a) (1.44 g) as a white solid: m/z 290/292 (M+H)$^+$ (ES$^+$). The filtrate was concentrated in vacuo and the residue triturated with ethanol/heptane to afford 2-bromo-6-(2-hydroxyacetamido)benzoic acid (7b) (1.02 g, combined yield, 59%): m/z 274/276 (M+H)$^+$ (ES$^+$). Both 7a and 7b can be used without further purification in the next step.

To a stirred mixture of compound (7a) (7.50 g, 27.4 mmol), 2-chlorobenzylamine (5.00 mL, 41.05 mmol) and triethylamine (5.70 mL, 41.1 mmol) in toluene (250 mL) was added a solution of phosphorus trichloride (2.60 mL, 30.1 mmol) in toluene (250 mL) dropwise over 1 hr. The reaction mixture was heated to 110° C. for 24 hr, whereupon the hot solution was decanted and concentrated in vacuo. The residue was triturated with propan-2-ol (50 mL) to afford the title compound (8) (6.41 g, 59%) as a yellow solid: m/z 397/399 (M+H)$^+$ (ES$^+$).

3-(2-(2-Methoxyethoxy)ethoxy)prop-1-yne (9)

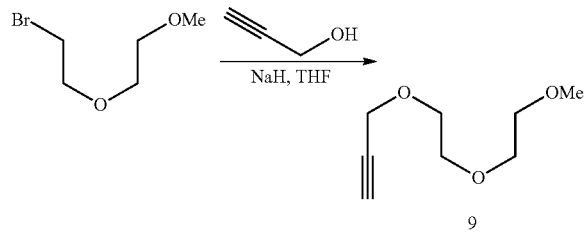

To a stirred suspension of sodium hydride (3.12 g, 78.0 mmol) in THF (100 mL) cooled to 5° C. in an ice-bath was added a solution of propargyl alcohol (4.60 g, 78.0 mmol) in THF (20 mL) drop-wise. The mixture was stirred at 5° C. for 30 min and was then allowed to warm to RT and treated dropwise with 1-bromo-2-(2-methoxyethoxy)ethane (7.00 mL, 52.0 mmol). The reaction mixture was stirred at RT for 16 hr and was then, diluted with water (100 mL) and extracted with diethyl ether (2×100 mL). The combined organic extracts were dried, filtered and evaporated in vacuo. The residue was purified by flash column chromatography, eluting with 30% EtOAc in heptane, to afford the title compound (9) (250 mg, 9%) as a colourless oil: $^1$H NMR (500 MHz, MeOD) δ: 4.18 (2H, d), 3.66-3.69 (2H, m), 3.60-3.66 (4H, m), 3.52-3.56 (2H, m), 3.36 (3H, s), 2.84 (1H, t).

2-(2-(Prop-2-ynyloxy)ethoxy)ethanol (10)

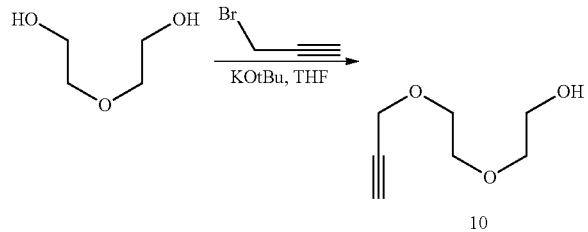

To a stirred suspension of potassium tert-butoxide (1.06 g, 9.42 mmol) in THF (300 mL) cooled to 0° C. in an ice-bath was added a solution of 2,2'-oxydiethanol (4.60 g, 78.0 mmol) in THF (10 mL). The mixture was stirred at 0° C. for 30 min and was then allowed to warm to RT and was treated dropwise with propargyl bromide (1.68 mL of an 80% solution in toluene, 11.30 mmol). The reaction mixture was stirred at RT for 16 hr and diluted with brine and water (5:1, 50 mL) and was extracted with EtOAc (3×500 mL). The combined organic extracts were dried, filtered and evaporated in vacuo. The residue was purified by flash column chromatography, eluting with 25 to 60% EtOAc in heptane, to afford the title compound (10) (410 mg, 30%) as a yellow oil: $^1$H NMR (250 MHz, CDCl$_3$) δ: 2.22 (1H, s), 2.45 (1H, t), 3.58-3.66 (2H, m), 3.67-3.79 (6H, m), 4.22 (2H, d).

1-Morpholinohex-5-yn-1-one (11)

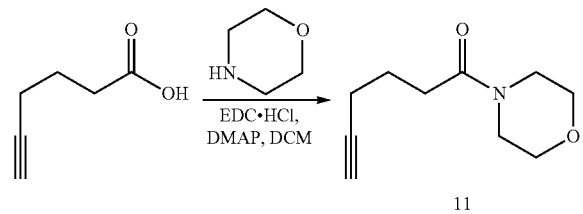

To a solution of hex-5-ynoic acid (500 mg, 4.46 mmol), DMAP (27 mg, 0.23 mmol) and EDC hydrochloride (940 mg, 4.90 mmol) in DCM (10 mL) was added morpholine (391 μL, 4.46 mmol). The reaction was stirred at RT overnight and then diluted with DCM (50 mL). The resulting solution was washed with water (3×10 mL), brine (10 mL) and aq hydrochloric acid (2 M, 2×20 mL) and was then dried, filtered and evaporated in vacuo to afford the title compound (11) (808 mg, 100%) as a yellow oil: $^1$H NMR (500 MHz, CDCl$_3$) δ: 3.65-3.71 (4H, m), 3.63 (2H, d), 3.45-3.54 (2H, m), 2.46 (2H, t), 2.26-2.33 (2H, m), 1.98 (1H, t), 1.88 (2H, quin).

2-Acetamido-N-(prop-2-ynyl)acetamide (12)

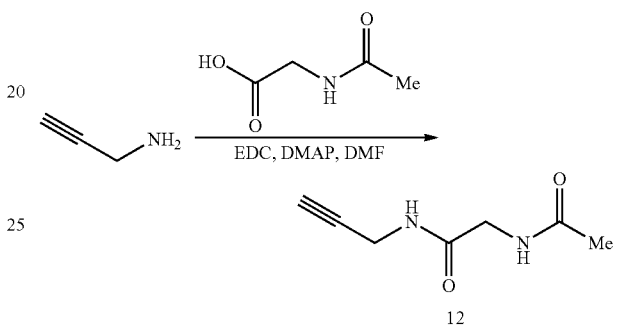

To a solution of N-acetylglycine (200 mg, 1.71 mmol), DMAP (11 mg, 0.09 mmol) and EDC hydrochloride (360 mg, 1.88 mmol) in DCM (10 mL) was added propargylamine (109 μL, 1.71 mmol). The reaction mixture was stirred at RT overnight and then evaporated in vacuo. The residue was purified by flash column chromatography, eluting with 0 to 5% methanol in DCM, to afford the title compound (12) (218 mg, 83%) as a white solid: $^1$H NMR (500 MHz, CDCl$_3$) δ: 2.07 (3H, s), 2.25 (1H, t), 3.95 (2H, d), 4.07 (2H, dd), 6.34 (1H, br s), 6.49 (1H, b s).

N-(But-3-ynyl)morpholine-4-carboxamide (13)

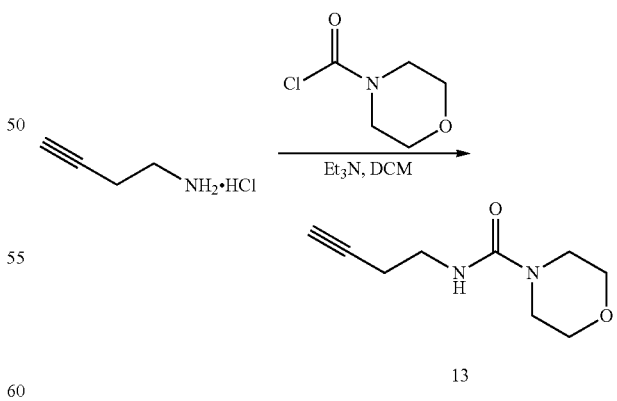

To a suspension of but-3-yn-1-amine hydrochloride (200 mg, 1.89 mmol) and triethylamine (425 μL, 3.78 mmol) in DCM (60 mL) was added morpholine-4-carbonyl chloride (218 μL, 1.89 mmol). The reaction was stirred at RT overnight and then washed with aq hydrochloric acid (2 M, 2×20 mL), saturated aq sodium bicarbonate (2×20 mL), dried, filtered and evaporated in vacuo. The residue was purified by flash column chromatography, eluting with 0-100% ethyl acetate in heptane, to afford the title compound (13) (164 mg, 48%) as a white solid. $^1$H NMR (500 MHz, DMSO-d$_6$) δ: 2.28 (2H, td), 2.82 (1H, t), 3.09-3.18 (2H, m), 3.20-3.27 (4H, m), 3.48-3.57 (4H, m), 6.74 (1H, t).

(2-Fluoro-3-methoxyphenyl)methanamine (15)

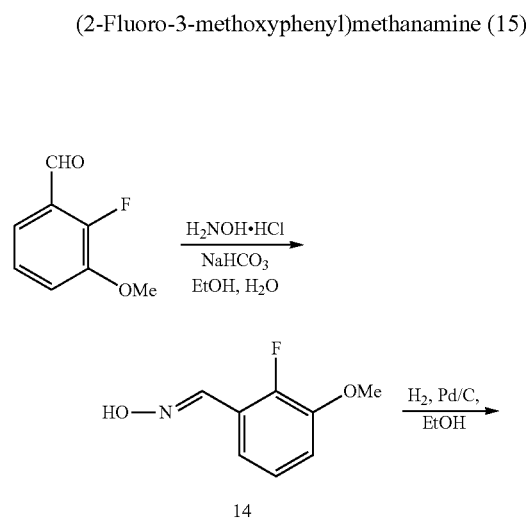

To a stirred solution of sodium hydrogen carbonate (2.73 g, 32.5 mmol) in water (50 mL) was added hydroxylamine hydrochloride (2.30 g, 33.2 mmol) in portions over 30 min. The resultant solution was added to a vigorously stirred suspension of 2-fluoro-3-methoxybenzaldehyde (5.00 g, 32.5 mmol) in ethanol (45 mL) and the reaction mixture stirred at RT for 16 hr. The resultant precipitate was removed by filtration and washed with water (3×100 mL) and then allowed to dry in air to afford 2-fluoro-3-methoxybenzaldehyde oxime (14) (4.69 g, 85%) as a white crystalline solid: m/z 170 (M+H)$^+$ (ES$^+$).

To a stirred solution of the oxime (14) (1.50 g, 8.86 mmol) in ethanol (70 mL) under nitrogen was added 10% palladium on carbon (100 mg). The reaction mixture was placed under an atmosphere of hydrogen and stirred at RT for 2 hr. The reaction mixture was filtered through Celite™, and was then evaporated in vacuo to remove the ethanol. The resultant crude residue was partitioned between ethyl acetate (50 mL) and aq hydrochloric acid (2 M, 50 mL). The aq layer was separated and was neutralised with saturated sodium hydrogen carbonate solution and then re-extracted with ethyl acetate (70 mL) followed by a mixture of 2-propanol and chloroform (1:1, 2×70 mL). The propanol/chloroform extracts were dried, filtered and evaporated in vacuo separately to afford the title compound (15) in two batches (batch 1: 346 mg, 25%; batch 2: 370 mg, 27%) as white solids: m/z 156 (M+H)$^+$ (ES$^+$) (method C).

2-((4-amino-3-iodo-1H-pyrazolo[3,4-d]pyrimidin-1-yl)methyl)-5-bromo-3-(2-chloro benzyl)quinazolin-4 (3H)-one: Intermediate A

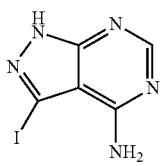

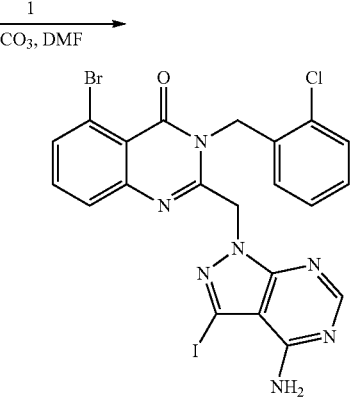

To a stirred mixture of 5-bromo-3-(2-chlorobenzyl)-2-(chloromethyl)quinazolin-4(3H)-one, (8), (13.6 g, 30.7 mmol) and 3-iodo-1H-pyrazolo[3,4-d]pyrimidin-4-amine (1) (8.09 g, 30.7 mmol) in DMF (300 mL was added potassium carbonate (6.36 g, 46.0 mmol) and the reaction maintained at RT in the dark for 24 hr. The mixture was poured onto water (4.0 L) and the resulting suspension was stirred at RT for 1 hr. The precipitate was isolated by filtration and dried in vacuo to afford the title compound, Intermediate A, as a colourless solid (18.0 g, 94%); m/z 622/624 [M+H]$^+$ (ES$^+$).

2-((4-Amino-3-(3-hydroxyphenyl)-1H-pyrazolo[3,4-d]pyrimidin-1-yl)methyl)-5-bromo-3-(2-chlorobenzyl)quinazolin-4(3H)-one: Intermediate B

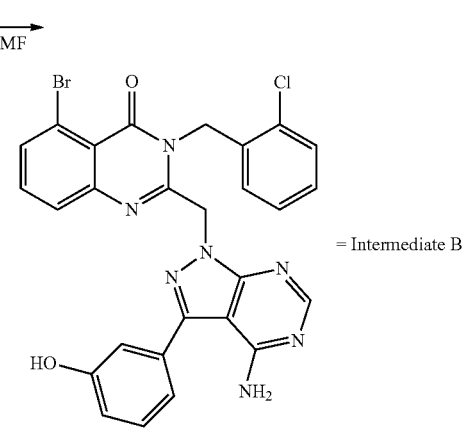

To a stirred mixture of compound (8) (100 mg, 0.25 mmol) and potassium carbonate (42 mg, 0.30 mmol) in DMF (2.5 mL) was added a solution of compound (3) (94 mg, 0.28 mmol) in DMF (2.5 mL) and the reaction mixture was stirred at RT for 18 hr. Potassium carbonate (3×35 mg, 0.75 mmol) was added in three portions over 30 hr. The solvent was removed in vacuo and the crude material was purified by flash column chromatography, eluting with 4.5% methanol in DCM, to afford the title compound (Intermediate B) (94 mg, 64%) as a off-white solid: m/z 588/590 (M+H)$^+$ (ES$^+$) (Method B).

2-((4-Amino-3-(4-hydroxyphenyl)-1H-pyrazolo[3,4-d]pyrimidin-1-yl)methyl)-5-bromo-3-(2-chlorobenzyl)quinazolin-4(3H)-one: Intermediate C

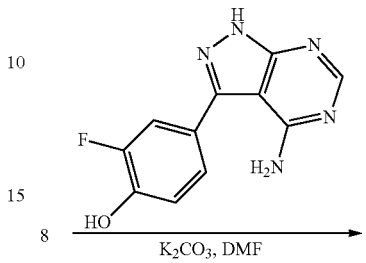

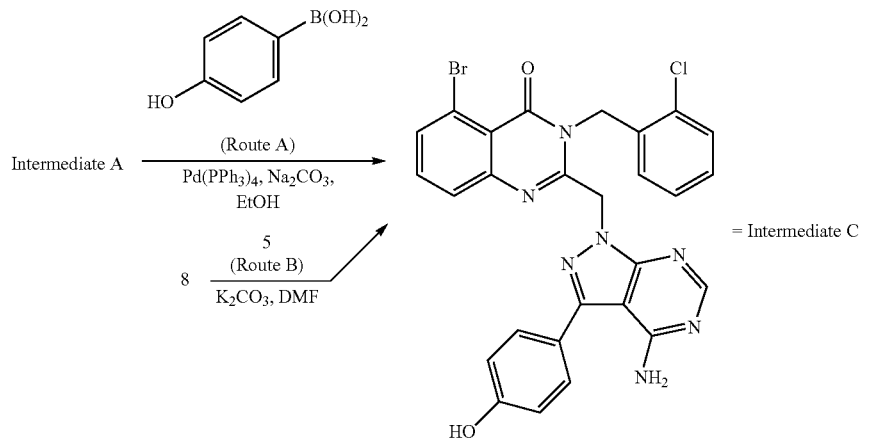 [SMILES: OB(O)c1ccc(O)cc1 ; Nc1ncnc2c1c(-c1ccc(O)cc1)nn2Cc1nc2cccc(Br)c2c(=O)n1Cc1ccccc1Cl]

Route A:

A thoroughly ground mixture of Intermediate A (10.0 g, 15.3 mmol), Na$_2$CO$_3$.10H$_2$O (9.60 g, 33.6 mmol), 4-hydroxyphenylboronic acid (4.21 g, 30.5 mmol), and Pd(Ph$_3$)$_4$ (1.32 g, 1.14 mmol) in EtOH (300 mL) was purged with nitrogen and was then stirred at 85° C. for 3 days. The mixture was cooled to RT and the precipitate was isolated by filtration and was washed with EtOH (100 mL). The solid was resuspended in water (100 mL) and was stirred for a further 30 min was then isolated by filtration, washed with EtOH (50 mL) and dried in vacuo to afford the title compound, Intermediate C as an off white solid (4.86 g, 51%); m/z 588/590 (M+H)$^+$ (ES$^+$).

Route B:

To a stirred mixture of compound (8) (100 mg, 0.25 mmol) and potassium carbonate (42 mg, 0.30 mmol) in DMF (2.5 mL) was added a solution of compound (5) (94 mg, 0.28 mmol) in DMF (2.5 mL) and the reaction mixture stirred at RT for 18 hr. The solvent was removed in vacuo and the crude material was purified by flash column chromatography, eluting with 4.5% methanol in DCM, to afford the title compound, Intermediate C (82 mg, 55%) as a cream solid: m/z 588/590 (M+H)$^+$ (ES$^+$) (Method B).

2-((4-Amino-3-(3-fluoro-4-hydroxyphenyl)-1H-pyrazolo[3,4-d]pyrimidin-1-yl)methyl)-5-bromo-3-(2-chlorobenzyl)quinazolin-4(3H)-one : Intermediate D

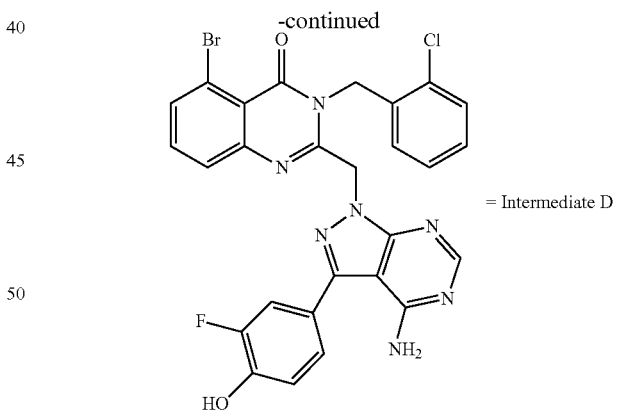

To a stirred mixture of compound (8) (200 mg, 0.502 mmol) and potassium carbonate (83 mg, 0.60 mmol) in DMF (2.0 mL) was added a solution of 4-(4-amino-1H-pyrazolo[3,4-d]pyrimidin-3-yl)-2-fluorophenol (see Table 1, below) (148 mg, 0.602 mmol) in DMF (2.0 mL) and the reaction mixture stirred at RT for 18 hr. The solvent was removed in vacuo and the crude material was purified by flash column chromatography, eluting with 5% methanol in DCM, to afford the title compound, Intermediate D (81 mg, 27%) as a off-white solid: m/z 606/608 (M+H)$^+$ (ES$^+$) (Method B).

2-((4-Amino-3-(4-hydroxy-3-methoxyphenyl)-1H-pyrazolo[3,4-d]pyrimidin-1-yl)methyl)-5-bromo-3-(2-chlorobenzyl)quinazolin-4(3H)-one: Intermediate E

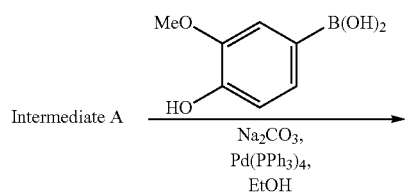

A mixture of Intermediate A (400 mg, 0.630 mmol), 2-methoxy-4-(4,4,5,5-tetramethyl-1,3,2-dioxaborolan-2-yl)phenol (189 mg, 0.755 mmol), Na$_2$CO$_3$·10H$_2$O (396 mg, 1.39 mmol) and Pd(Ph$_3$)$_4$ (55 mg, 0.047 mmol) in EtOH (12 mL) was purged with nitrogen and was then stirred at 85° C. for 24 hr. The mixture was cooled and was evaporated in vacuo and the residue was purified by flash column chromatography (SiO$_2$, 80 g, MeOH in CH$_2$Cl$_2$, 0-10%, gradient elution) to afford the title compound, Intermediate E, as a pale brown solid (225 mg, 56%); m/z 618/620 (M+H)$^+$ (ES$^+$).

2-((4-Amino-3-(4-hydroxyphenyl)-1H-pyrazolo[3,4-d]pyrimidin-1-yl)methyl)-3-(2-chlorobenzyl)-5-(5-iodopent-1-ynyl)quinazolin-4(3H)-one: Intermediate F

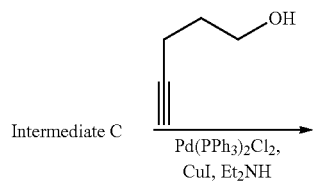

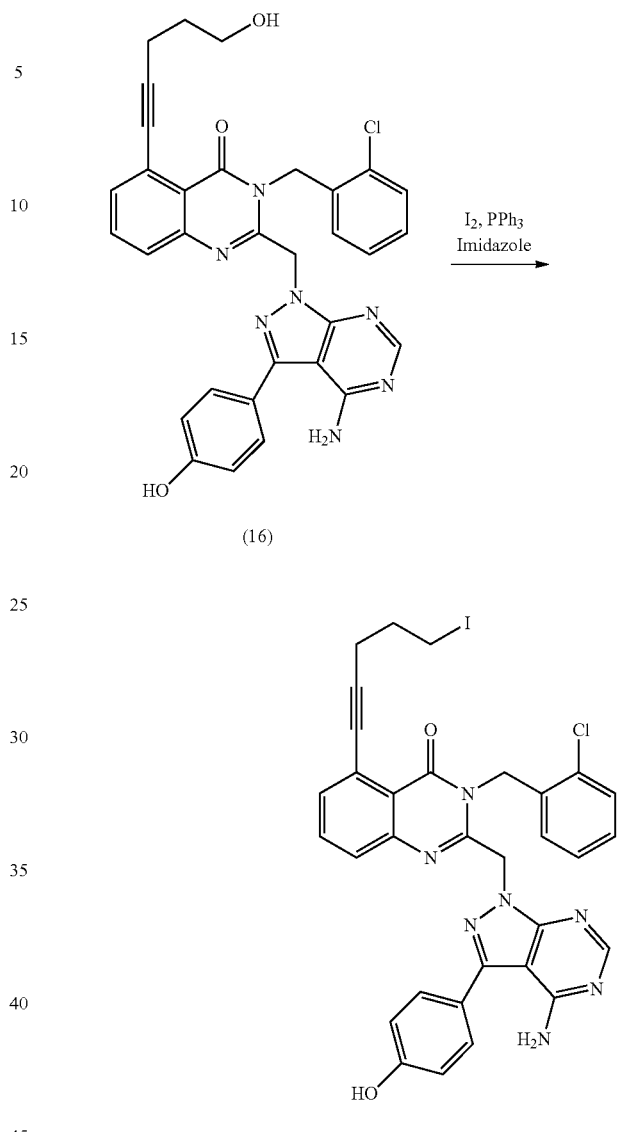

To a mixture of Intermediate C (503 mg, 0.854 mmol), copper(I) iodide (17 mg, 0.089 mmol) and bis(triphenylphosphine)palladium(II) dichloride (64 mg, 0.089 mmol) in diethylamine (3.2 mL, 31 mmol) was added pent-4-yn-1-ol (157 µL, 1.70 mmol). The reaction mixture was de-gassed with N$_2$ and was heated at 60° C. for 2.5 hr and then cooled to RT. The resulting mixture was evaporated in vacuo and the residue was triturated with EtOAc (5.0 mL) and dried in vacuo to afford 2-((4-amino-3-(4-hydroxyphenyl)-1H-pyrazolo[3,4-d]pyrimidin-1-yl)methyl)-3-(2-chlorobenzyl)-5-(5-hydroxypent-1-ynyl)quinazolin-4(3H)-one (16) as a brown solid (488 mg, 92% pure, 89%); m/z 590/592 (M+H)$^+$ (ES$^+$) (Method D).

To a stirred suspension of the alcohol (16) (162 mg, 92% pure, 0.252 mmol) in DCM (8.0 mL) was added iodine (121 mg, 0.477 mmol), triphenylphosphine (115 mg, 0.438 mmol) and imidazole (35 mg, 0.51 mmol) and the mixture maintained at RT for 2 hr. The reaction mixture was evaporated in vacuo and the residue was purified by flash column chromatography (SiO$_2$, 40 g, MeOH in DCM, 0-10%, gradient elution) to afford Intermediate F (109 mg, 73% pure, 45.0%) as a yellow solid m/z 702/704 (M+H)$^+$ (ES$^+$) (Method D), which was used without further purification in subsequent transformations.

Additional intermediates and non-commercial building blocks, that appear in the reaction schemes which follow, were prepared using the procedures described above for analogous derivatives or by the methods described in the cited literature references (Table 1).

TABLE 1

Non Commercial Compounds

| Structure | Compound Name | Literature Citation or Analogous Procedure |
|---|---|---|
| 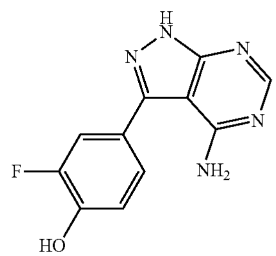 [SMILES: Nc1ncnc2[nH]nc(-c3ccc(O)c(F)c3)c12] | 4-(4-amino-1H-pyrazolo[3,4-d]pyrimidin-3-yl)-2-fluorophenyl | Prepared using procedures for (1)→(4) starting from 3-fluoro-4-phenol boronic acid |
| 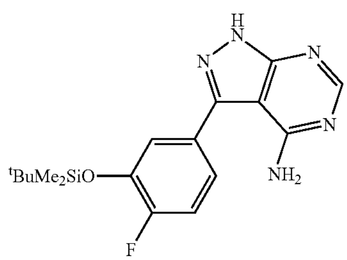 | 3-(3-(tert-butyldimethylsilyloxy)-4-fluorophenyl)-1H-pyrazolo[3,4-d]pyrimidin-4-amine | Prepared using the methodology for (1)→(2)→(3) starting from 4-fluoro-3-phenol boronic acid |
| 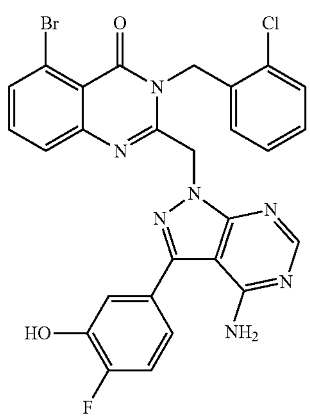 [SMILES: Nc1ncnc2c1c(-c1ccc(F)c(O)c1)nn2Cc1nc2cccc(Br)c2c(=O)n1Cc1ccccc1Cl] | 2-((4-amino-3-(4-fluoro-3-hydroxyphenyl)-1H-pyrazolo[3,4-d]pyrimidin-1-yl)methyl)-5-bromo-3-(2-chlorobenzyl)quinazolin-4(3H)-one | Prepared using the methodology for (Intermediate D) starting from 3-(3-tert-butyl dimethylsilyloxy)-4-fluoro phenyl)-1H-pyrazolo[3,4-d]pyrimidin-4-amine |
| 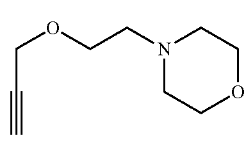 | 4-(2-(prop-2-yn-1-yloxy)ethyl)morpholine | Gautier et al., *Annales Pharmaceutiques Francaises*, 1971, 29, 39-50 |
| 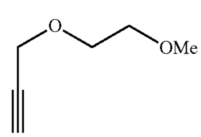 | 3-(2-methoxyethoxy)prop-1-yne | Prepared using the procedure for compound (9) starting from 2-bromoethyl methyl ether |
| 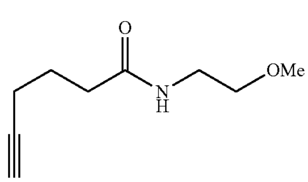 | N-(2-methoxyethyl)hex-5-ynamide | Prepared using the procedure for compound (11) substituting 2-methoxyethanamine |

TABLE 1-continued

Non Commercial Compounds

| Structure | Compound Name | Literature Citation or Analogous Procedure |
|---|---|---|
| 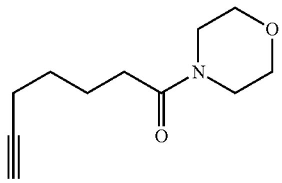 | 1-morpholinohept-6-yn-1-one | Prepared using the procedure for compound (11) from hept-6-ynoic acid |
| 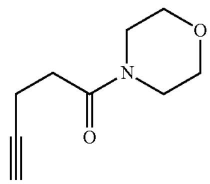 | 1-morpholinopent-4-yn-1-one | Prepared using the procedure for compound (11) from pent-4-ynoic acid |
| 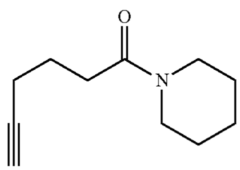 | 1-(piperidin-1-yl)hex-5-yn-1-one | Prepared using the procedure for compound (11) substituting piperidine |
| 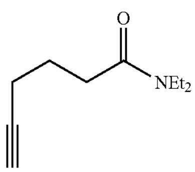 | N,N-diethylhex-5-ynamide | Prepared using the procedure for compound (11) substituting diethylamine |
| 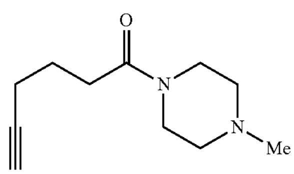 | 1-(4-methylpiperazin-1-yl)hex-5-en-1-one | Prepared using the procedure for compound (11) substituting 4-methyl piperazine |
| 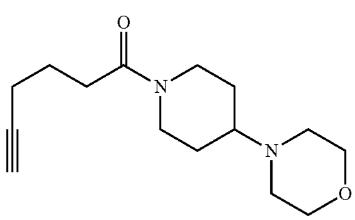 [SMILES: C#CCCCC(=O)N1CCC(N2CCOCC2)CC1] | 1-(4-morpholinopiperidin-1-yl)hex-5-yn-1-one | Prepared using the procedure for compound (11) substituting 4-morpholinopiperidine |
| 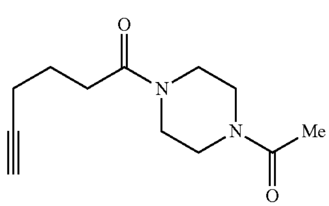 [SMILES: C#CCCCC(=O)N1CCN(C(C)=O)CC1] | 1-(4-acetylpiperazin-1-yl)hex-5-yn-1-one | Prepared using the procedure for compound (11) substituting 4-acetyl piperazine |
| 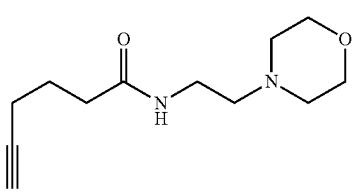 [SMILES: C#CCCCC(=O)NCCN1CCOCC1] | N-(2-morpholinoethyl)hex-5-ynamide | Prepared using the procedure for compound (11) substituting 2-morpholinoethanamine |

TABLE 1-continued

Non Commercial Compounds

| Structure | Compound Name | Literature Citation or Analogous Procedure |
|---|---|---|
| 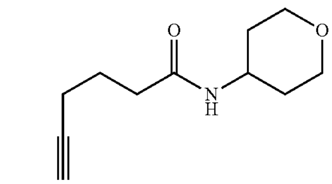 | N-(tetrahydro-2H-pyran-4-yl)hex-5-ynamide | Prepared using the procedure for compound (11) substituting tetrahydro-2H-pyran-4-amine |
| 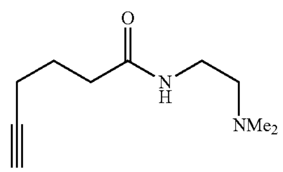 | N-(2-(dimethylamino)ethyl)hex-5-ynamide | Prepared using the procedure for compound (11) substituting N',N'-dimethylethane-1,2-diamine |
| 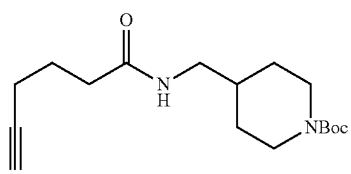 [SMILES: C#CCCCC(=O)NCC1CCN(C(=O)OC(C)(C)C)CC1] | tert-butyl 4-(hex-5-ynamidomethyl)piperidine-1-carboxylate | Prepared using the procedure for compound (11) substituting tert-butyl 4-(aminomethyl)piperidine-1-carboxylate |
| 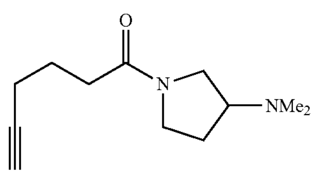 | (R)-1-(3-(dimethylamino)pyrrolidin-1-yl)hex-5-yn-1-one | Prepared using the procedure for compound (11) substituting (R)-N,N-dimethylpyrrolidin-3-amine |
| 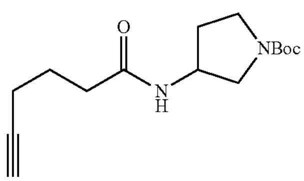 [SMILES: C#CCCCC(=O)NC1CCN(C(=O)OC(C)(C)C)C1] | tert-butyl 3-(hex-5-ynamido)pyrrolidine-1-carboxylate | Prepared using the procedure for compound (11) substituting tert-butyl 3-aminopyrrolidine-1-carboxylate |
| 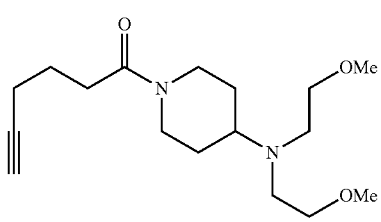 [SMILES: C#CCCCC(=O)N1CCC(N(CCOC)CCOC)CC1] | 1-(4-(bis(2-methoxyethyl)amino)piperidin-1-yl)hex-5-yn-1-one | Prepared using the procedure for compound (11) substituting bis(2-methoxyethyl)amine |
| 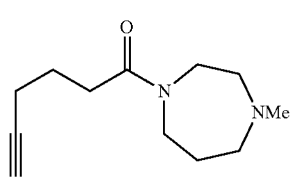 | 1-(4-methyl-1,4-diazepan-1-yl)hex-5-yn-1-one | Prepared using the procedure for compound (11) substituting 1-methyl-1,4-diazepane |
| 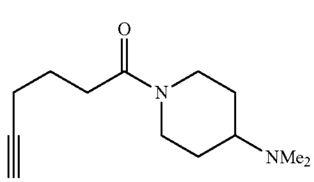 [SMILES: C#CCCCC(=O)N1CCC(N(C)C)CC1] | 1-(4-dimethylamino)piperidin-1-yl)hex-5-yn-1-one | Prepared using the procedure for compound (11) substituting 4-dimethylaminopiperidine |

TABLE 1-continued

Non Commercial Compounds

| Structure | Compound Name | Literature Citation or Analogous Procedure |
|---|---|---|
| 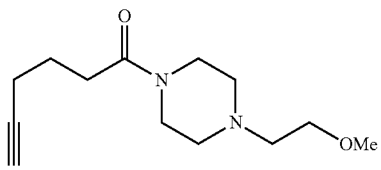 [SMILES: C#CCCCC(=O)N1CCN(CCOC)CC1] | 1-(4-(2-methoxyethyl)piperazin-1-yl)hex-5-yn-1-one | Prepared using the procedure for compound (11) substituting 1-(2-methoxyethyl)piperazine |
| 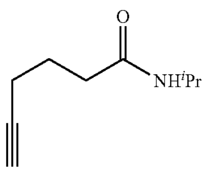 | N-isopropylhex-5-ynamide | Prepared using the procedure for compound (11) substituting propan-2-amine |
| 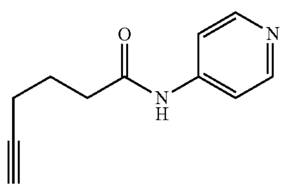 | N-(pyridin-4-yl)hex-5-ynamide | Prepared using the procedure for compound (11) substituting pyridin-4-amine |
| 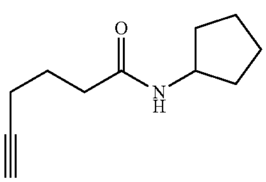 | N-cyclopentylhex-5-ynamide | Prepared using the procedure for compound (11) substituting cyclopentanamine |
| 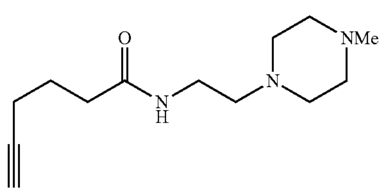 [SMILES: C#CCCCC(=O)NCCN1CCN(C)CC1] | N-(2-(4-methylpiperazin-1-yl)ethyl)hex-5-ynamide | Prepared using the procedure for compound (11) substituting 2-(4-methyl piperazin-1-yl)ethanamine |
| 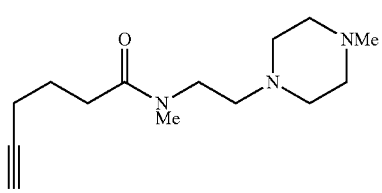 [SMILES: C#CCCCC(=O)N(C)CCN1CCN(C)CC1] | N-methyl-N-(2-(4-methylpiperazin-1-yl)ethyl)hex-5-ynamide | Prepared using the procedure for compound (11) substituting N-methyl-2-(4-methylpiperazin-1-yl)ethanamine |
| 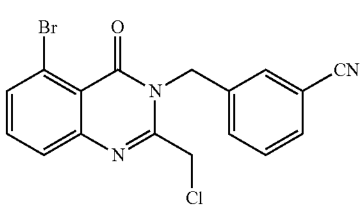 [SMILES: N#Cc1cccc(Cn2c(CCl)nc3cccc(Br)c3c2=O)c1] | 3-((5-bromo-2-(chloromethyl)-4-oxoquinazolin-3(4H)-yl)methyl)benzonitrile, Compound (17) | Prepared using the methodology employed to generate compound (8) substituting 3-cyano benzylamine hydrochloride in the second step |

TABLE 1-continued

Non Commercial Compounds

| Structure | Compound Name | Literature Citation or Analogous Procedure |
|---|---|---|
| 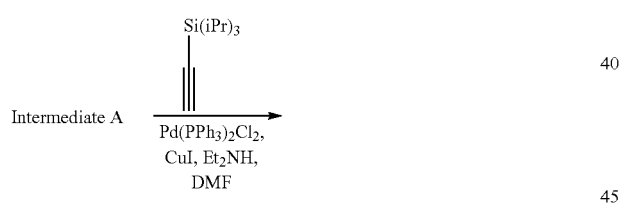 | 3-((2-((4-amino-3-(3-hydroxyphenyl)-1H-pyrazolo[3,4-d]pyrimidin-1-yl)methyl)-5-bromo-4-oxoquinazolin-3(4H)-yl)methyl)benzonitrile; Compound (18) | Prepared according to the methodology used to generate Intermediate B, substituting Compound (17) |

Compound Examples

Example 1

2-((4-Amino-3-(3-hydroxyphenyl)-1H-pyrazolo[3,4-d]pyrimidin-1-yl)methyl)-3-(2-chlorobenzyl)-5-ethynylquinazolin-4(3H)-one

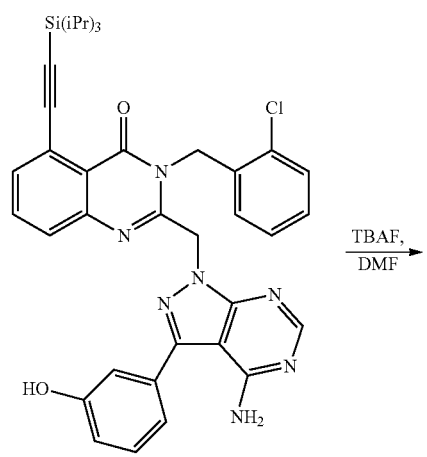

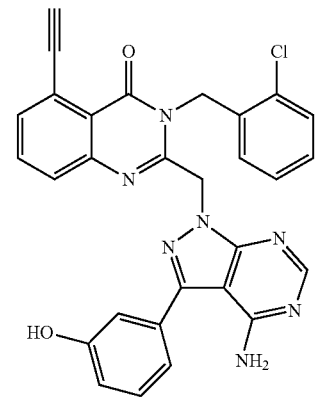

Example 1

To a mixture of Intermediate A (91 mg, 0.15 mmol), (triisopropylsilyl)acetylene (87 µL, 0.39 mmol), copper (I) iodide (1.8 mg, 0.01 mmol) and diethylamine (242 µL, 2.31 mmol) in degassed DMF (2.0 mL) was added bis(triphenylphosphine)palladium (II) dichloride (6.5 mg, 0.01 mmol). The reaction mixture was purged with nitrogen, sealed and then heated under microwave irradiation (120° C., 200 W, CEM: Discover microwave) for 20 min. The mixture was cooled to RT, diluted with EtOAc (3 mL) and washed with water (1 mL). The aq phase was back extracted with EtOAc (1.0 mL) and the combined organic extracts were washed with water (1.0 mL). The aq phase was back extracted with EtOAc (1.0 mL) and the combined organic extracts were washed with water (1.0 mL). The aq phase was back extracted with EtOAc (1.0 mL) and the combined organic extracts were washed with a saturated solution of aq ammonium chloride (2×2.0 mL) and then dried, filtered and evaporated in vacuo. The crude material was triturated with methanol (1.0 mL) and the resulting solid was purified by flash column chromatography, eluting with 0 to 50% methanol in DCM, to afford 2-((4-amino-3-(3-hydroxyphenyl)-1H-pyrazolo[3,4-d]pyrimidin-1-yl)methyl)-3-(2-chlorobenzyl)-5-((triisopropylsilyl)ethynyl)quinazolin-4(3H)-one (19) (107 mg, 100%) as a white solid: m/z 690/692 (M+H)$^+$ (ES$^+$).

To a stirred solution of compound (19) (107 mg, 0.15 mmol) in DMF (0.50 mL) was added tetrabutylammonium fluoride (190 μL of a 1.0 M solution in THF, 0.19 mmol). After 10 min, the reaction mixture was diluted with water (3.0 mL) and cooled to 0° C. for 30 min. The resulting solid was collected by filtration and purified by flash column chromatography, eluting with 4.5% methanol in DCM, to afford the title compound, Example 1, (70 mg, 85%) as a white solid: m/z 534/536 (M+H)$^+$ (ES$^+$); R$^t$ 3.73 min; $^1$H NMR (500 MHz, DMSO-d$_6$) δ: 4.42 (1H, s), 5.30 (2H, s), 5.77 (2H, s), 6.16 (1H, d), 6.79 (1H, t), 6.84 (1H, dd), 6.89-6.96 (2H, m), 7.04 (1H, t), 7.14 (1H, d), 7.30 (1H, t), 7.70 (1H, d), 7.75 (1H, d), 7.80-7.87 (1H, m), 8.18 (1H, s), 9.67 (1H, s).

Example 2

2-((4-Amino-3-(3-hydroxyphenyl)-1H-pyrazolo[3,4-d]pyrimidin-1-yl)methyl)-3-(2-chlorobenzyl)-5-(3-(2-(2-methoxyethoxy)ethoxy)prop-1-yn-1-yl)quinazolin-4(3H)-one

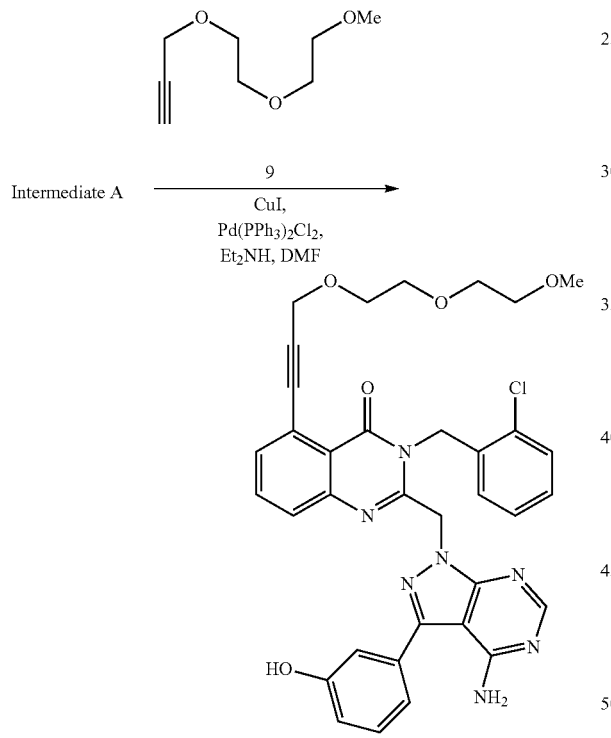

Example 2

To a mixture of Intermediate A (50 mg, 84.9 μmol), the acetylene (9) (20 mg, 0.13 mmol), copper iodide (1.0 mg, 5.09 μmol) and diethylamine (133 μL, 1.27 mmol) in degassed DMF (1.0 mL) was added bis(triphenylphosphine)palladium(II) dichloride (3.6 mg, 5.09 μmol). The reaction mixture was purged with nitrogen, sealed and then heated under microwave irradiation (120° C., 200 W, CEM: Discover microwave) for 20 min. The mixture was cooled to RT and was diluted with water (10 mL) and extracted with EtOAc (2×20 mL). The combined organic extracts were dried, filtered and evaporated in vacuo. The residue was purified by flash column chromatography, eluting with 0-8% MeOH in DCM, to afford the title compound, Example 2, (21 mg, 36%) as an orange solid: m/z 667 (M+H)$^+$ (ES$^+$); R$^t$ 3.68 min; $^1$H NMR (500 MHz, DMSO-d$_6$) δ: 3.19 (3H, s), 3.37 (2H, dd), 3.46 (2H, dd), 3.48-3.52 (2H, m), 3.59-3.64 (2H, m), 4.38 (2H, s), 5.30 (2H, s), 5.76 (2H, s), 6.16 (1H, d), 6.76-6.81 (1H, m), 6.84 (1H, dd), 6.89-6.95 (2H, m), 7.01-7.07 (1H, m), 7.13 (1H, d), 7.30 (1H, t), 7.67 (1H, d), 7.73 (1H, d), 7.84 (1H, t), 8.17 (1H, s), 9.66 (1H, s).

Example 3

2-((4-Amino-3-(3-hydroxyphenyl)-1H-pyrazolo[3,4-d]pyrimidin-1-yl)methyl)-3-(2-chlorobenzyl)-5-(6-morpholino-6-oxohex-1-yn-1-yl)quinazolin-4(3H)-one

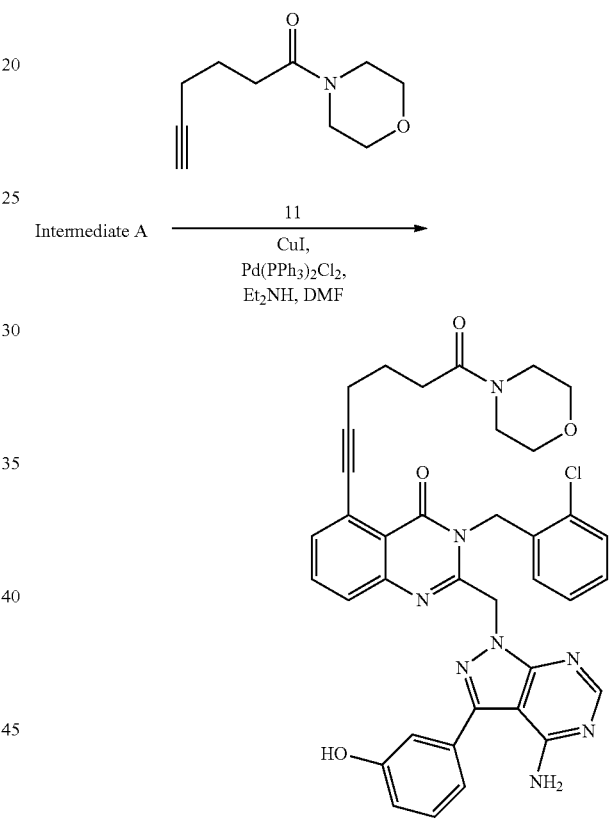

Example 3

To a mixture of Intermediate A (50 mg, 85 μmol), compound (11) (38 mg, 212 μmol), copper iodide (1.0 mg, 5.1 μmol) and diethylamine (133 μL, 1.27 mmol) in degassed DMF (2.0 mL) was added bis(triphenylphosphine)palladium (II) dichloride (4.0 mg, 5.1 μmol). The reaction mixture was purged with nitrogen, sealed and then heated under microwave irradiation (120° C., 200 W, CEM: Discover microwave) for 20 min. The reaction mixture was concentrated and the residue was purified by flash column chromatography, eluting with 0-50% methanol in DCM, to afford the title compound, Example 3, (31 mg, 53%) as a white solid: m/z 689/691 (M+H)$^+$ (ES$^+$), R$^t$ 3.63 min; $^1$H NMR (500 MHz, DMSO-d$_6$) δ: 1.66-1.76 (2H, m), 2.45-2.55 (4H, m), 3.19-3.26 (2H, m), 3.28-3.36 (4H, m), 3.41-3.47 (2H, m), 5.29 (2H, s), 5.75 (2H, s), 6.14 (1H, d), 6.78 (1H, t), 6.84 (1H, d)

6.89-6.94 (2H, m) 7.03 (1H, t) 7.11 (1H, d) 7.26-7.33 (1H, m) 7.60 (1H, d) 7.68 (1H, d), 7.77-7.83 (1H, m), 8.18 (1H, s), 9.68 (1H, s).

Example 4

6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)hex-5-ynoic acid

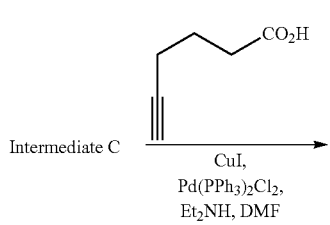

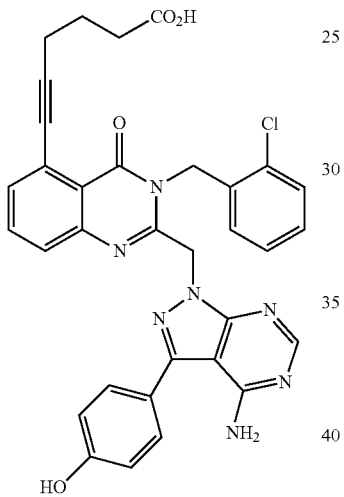

Example 4

To a mixture of Intermediate C (150 mg, 0.25 mmol), hex-5-ynoic acid (69 µL, 0.63 mmol), copper iodide (3.0 mg, 0.02 mmol) and diethylamine (400 µL, 3.75 mmol) in degassed DMF (1.5 mL) was added bis(triphenylphosphine)palladium(II) dichloride (11.0 mg, 0.02 mmol). The reaction mixture was purged with nitrogen, sealed and then heated under microwave irradiation (120° C., 200 W, CEM: Discover microwave) for 20 min. The mixture was cooled to RT, diluted with water (2.0 mL) and EtOAc (2.0 mL) and neutralised with 1 M aq hydrochloric acid to pH 7. The suspension was concentrated and purified by flash column chromatography, eluting with 0-50% methanol in DCM to afford the title compound, Example 4, (22 mg, 14%) as a yellow solid: m/z 620/622 (M+H)$^+$ (ES$^+$); R$^r$ 3.47 min; $^1$H NMR (500 MHz, DMSO-d$_6$) δ: 1.68-1.78 (2H, m), 2.29-2.41 (2H, m), 2.42-2.47 (2H, m), 5.29 (2H, s), 5.72 (2H, s), 6.19 (1H, d), 6.79 (1H, t), 6.88 (2H, d), 7.03 (1H, t), 7.12 (1H, d), 7.32 (2H, d), 7.60 (1H, d), 7.66 (1H, d), 7.78 (1H, t), 8.16 (1H, s), 9.73 (1H, s), 12.04 (1H, s).

Example 5

2-((4-Amino-3-(4-hydroxyphenyl)-1H-pyrazolo[3,4-d]pyrimidin-1-yl)methyl)-3-(2-chlorobenzyl)-5-(6-morpholino-6-oxohex-1-yn-1-yl)quinazolin-4(3H)-one

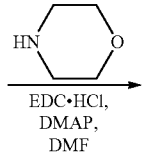

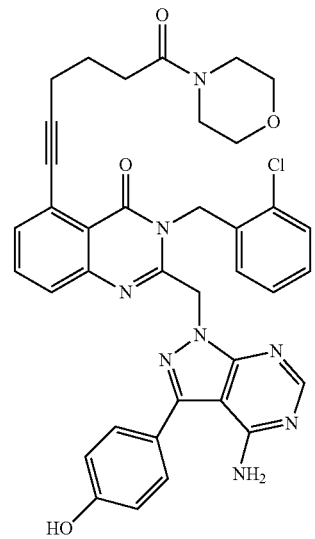

Example 5

To a solution of Example 4 (16.0 mg, 26 µmol), 4-dimethylaminopyridine (0.6 mg, 5.2 µmol), and EDC hydrochloride (5.3 mg, 28 µmol) in DMF (0.5 mL) was added morpholine (2.3 µL, 26 µmol). The reaction mixture was stirred at RT overnight and then diluted with water (5.0 mL). The resulting solid was collected by filtration and purified by flash column chromatography, eluting with 0-7% methanol in DCM to afford the title compound, Example 5, (7.0 mg, 57%) as a yellow solid: m/z 689/691 (M+H)$^+$ (ES$^+$); R$^r$ 3.54 min; $^1$H NMR (500 MHz, DMSO-d$_6$) δ: 1.71 (2H, quin), 2.43-2.49 (2H, m), 2.52-2.55 (2H, m), 3.20-3.26 (2H, m), 3.28-3.33 (4H, m), 3.44 (2H, t), 5.28 (2H, s), 5.72 (2H, s), 6.17 (1H, d), 6.78 (1H, t), 6.87 (2H, d), 7.02 (1H, t), 7.10 (1H, d), 7.32 (2H, d), 7.60 (1H, d), 7.67 (1H, d), 7.79 (1H, t), 8.16 (1H, s), 9.75 (1H, s).

Example 6

3-((2-((4-Amino-3-(3-hydroxyphenyl)-1H-pyrazolo[3,4-d]pyrimidin-1-yl)methyl)-5-(3-(2-(2-hydroxyethoxy)ethoxy)prop-1-yn-1-yl)-4-oxoquinazolin-3(4H)-yl)methyl)benzonitrile

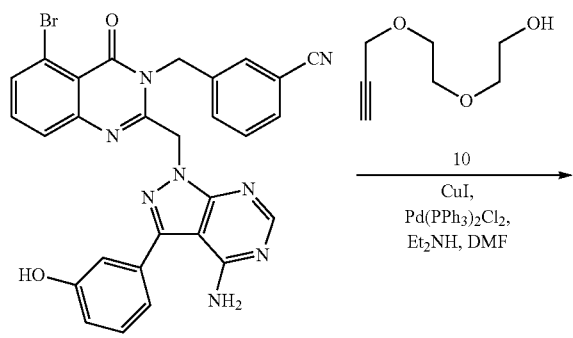

Example 6

To a mixture of the aryl bromide (18), (see Table 1, above) (50 mg, 86 μmol), the acetylene (10) (31 mg, 216 μmol), copper iodide (1.0 mg, 5.1 μmol) and diethylamine (135 μL, 1.29 mmol) in degassed DMF (1.0 mL) was added bis(triphenylphosphine)palladium(II) dichloride (3.6 mg, 5.2 μmol). The reaction mixture was purged with nitrogen, sealed and then heated in the microwave (120° C., 200 W, CEM: Discover microwave) for 20 min. The reaction mixture was concentrated and the residue was purified by flash column chromatography, eluting with 5.5% methanol in DCM, to afford the title compound, Example 6, (21 mg, 38%) as a white solid: m/z 643 (M+H)$^+$ (ES$^+$), Rt (min) 3.22; $^1$H NMR (500 MHz, DMSO-d$_6$) δ: 3.37-3.40 (2H, m), 3.41-3.47 (2H, m), 3.49-3.55 (2H, m), 3.62-3.67 (2H, m), 4.40 (2H, s), 4.59 (1H, t), 5.37 (2H, s), 5.74 (2H, s), 6.81-6.86 (1H, m), 6.89-6.97 (3H, m), 7.18 (1H, t), 7.22 (1H, s), 7.29 (1H, t), 7.51 (1H, d), 7.63-7.68 (2H, m), 7.77-7.83 (1H, m), 8.27 (1H, br s), 9.68 (1H, s).

Example 7

2-((4-Amino-3-(4-hydroxyphenyl)-1H-pyrazolo[3,4-d]pyrimidin-1-yl)methyl)-3-(2-chlorobenzyl)-5-(5-(cyclopentylamino)pent-1-ynyl)quinazolin-4(3H)-one

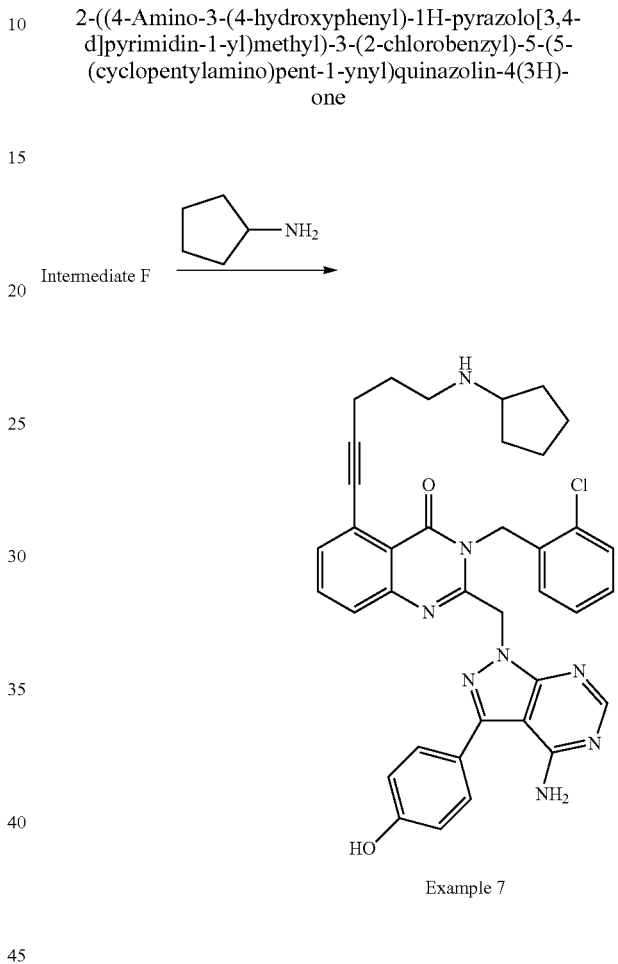

Example 7

To a suspension of Intermediate F (100 mg, 73% pure, 0.142 mmol) in DCM (10 mL) at RT was added cyclopentanamine (0.100 mL, 1.01 mmol). The suspension rapidly dissolved and the resulting solution was stirred at RT for 3 days then evaporated in vacuo. The residue was purified by flash column chromatography (SiO$_2$, 12 g, MeOH in EtOAc, 0-100%, gradient elution) and the crude product so obtained was triturated with MeCN to afford Example 7 as a yellow solid (16 mg, 17%); R$^t$ 1.39 min; m/z 659/661 (M+H)$^+$ (ES$^+$) (Method D); $^1$H NMR (400 MHz, DMSO-d$_6$) δ: 1.22 (2H, m), 1.38 (2H, m), 1.50-1.64 (6H, overlapping m), 2.46 (2H, t), 2.60 (2H, t), 2.89 (1H, quin), 5.29 (2H, s), 5.73 (2H, s), 6.15 (1H, d), 6.77 (1H, td), 6.87 (2H, d), 7.02 (1H, m), 7.11 (1H, dd), 7.32 (2H, d), 7.58 (1H, dd), 7.67 (1H, dd), 7.78 (1H, m), 8.16 (1H, s), 9.77 (1H, br s).

Additional examples, set out below (Table 2), were prepared utilising the same synthetic methodologies as those disclosed above.

TABLE 2

| Example No. | Structure | Name and Analytical Data |
| --- | --- | --- |
| 8 | 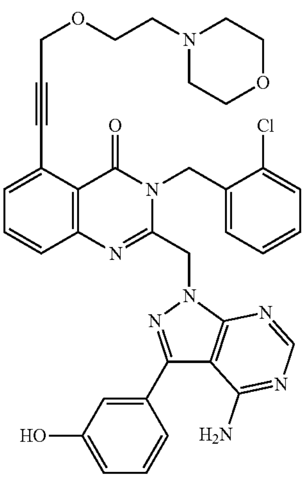 [SMILES: Nc1ncnc2c1c(-c1cccc(O)c1)nn2Cc1nc2cccc(C#CCOCCN3CCOCC3)c2c(=O)n1Cc1ccccc1Cl] | 2-((4-Amino-3-(3-hydroxyphenyl)-1H-pyrazolo[3,4-d]pyrimidin-1-yl)methyl)-3-(2-chlorobenzyl)-5-(3-(2-morpholinoethoxy)prop-1-ynyl)quinazolin-4(3H)-one. R$^t$ 2.89 min; m/z 677 (M + H)$^+$ (ES$^+$); $^1$H NMR (500 MHz, DMSO-d$_6$) δ: 2.31 (4H, br s), 2.43 (2H, br s), 3.45 (4H, t), 3.63 (2H, t), 4.37 (2H, s), 5.29 (2H, s), 5.76 (2H, s), 6.15 (1H, d), 6.78 (1H, t), 6.81-6.87 (1H, m), 6.89-6.95 (2H, m), 7.03 (1H, t), 7.12 (1H, d), 7.30 (1H, t), 7.65 (1H, d), 7.70-7.77 (1H, m), 7.80-7.89 (1H, m), 8.18 (1H, s), 9.67 (1H, s). |
| 9 | 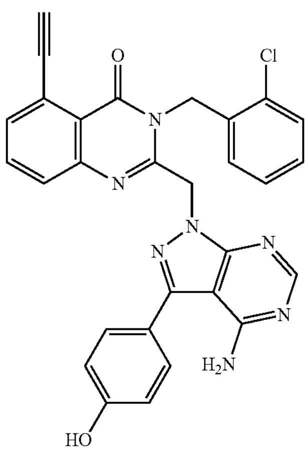 [SMILES: C#Cc1cccc2nc(Cn3nc(-c4ccc(O)cc4)c4c(N)ncnc43)n(Cc3ccccc3Cl)c(=O)c12] | 2-((4-Amino-3-(4-hydroxyphenyl)-1H-pyrazolo[3,4-d]pyrimidin-1-yl)methyl)-3-(2-chlorobenzyl)-5-ethynyl quinazolin-4(3H)-one. R$^t$ 3.64 min; m/z 534/536 (M + H)$^+$ (ES$^+$); $^1$H NMR (500 MHz, DMSO-d$_6$) δ: 4.41 (1H, s), 5.28 (2H, s), 5.74 (2H, s), 6.16 (1H, d), 6.77 (1H, t), 6.87 (2H, d), 6.99-7.06 (1H, m), 7.12 (1H, d), 7.32 (2H, d), 7.70 (1H, d), 7.75 (1H, dd), 7.80-7.87 (1H, m), 8.15 (1H, s), 9.76 (1H, s). |
| 10 | 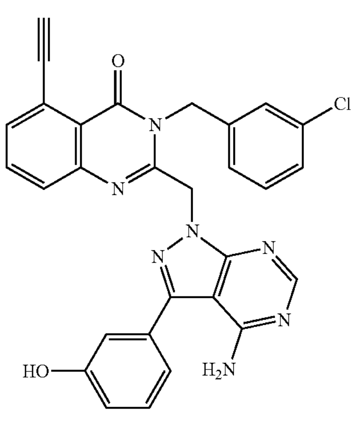 [SMILES: C#Cc1cccc2nc(Cn3nc(-c4cccc(O)c4)c4c(N)ncnc43)n(Cc3cccc(Cl)c3)c(=O)c12] | 2-((4-Amino-3-(3-hydroxyphenyl)-1H-pyrazolo[3,4-d]pyrimidin-1-yl)methyl)-3-(3-chlorobenzyl)-5-ethynyl quinazolin-4(3H)-one. R$^t$ 3.73 min; m/z 534/536 (M + H)$^+$ (ES$^+$); $^1$H NMR (500 MHz, DMSO-d$_6$) δ: 4.45 (1H, s), 5.36 (2H, s), 5.75 (2H, s), 6.70 (1H, d), 6.81-6.87 (2H, m), 6.92-6.98 (2H, m), 7.07 (1H, t), 7.11-7.19 (1H, m), 7.30 (1H, t), 7.61 (1H, d), 7.66-7.70 (1H, m), 7.75-7.81 (1H, m), 8.23 (1H, s), 9.66 (1H, s). |

TABLE 2-continued

| Example No. | Structure | Name and Analytical Data |
|---|---|---|
| 11 | 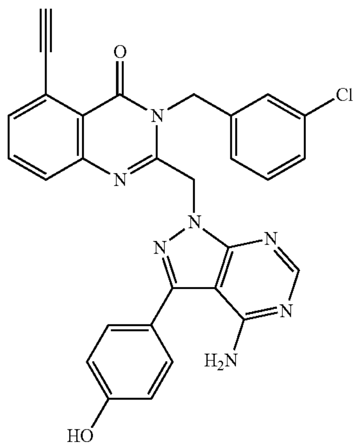 [SMILES: C#Cc1cccc2nc(Cn3nc(-c4ccc(O)cc4)c4c(N)ncnc43)n(Cc3cccc(Cl)c3)c(=O)c12] | 2-((4-Amino-3-(4-hydroxyphenyl)-1H-pyrazolo[3,4-d]pyrimidin-1-yl)methyl)-3-(3-chlorobenzyl)-5-ethynyl quinazolin-4(3H)-one.<br>$R^t$ 3.65 min; m/z 534/536 (M + H)$^+$ (ES$^+$);<br>$^1$H NMR (500 MHz, DMSO-d$_6$) δ: 4.44 (1H, s), 5.35 (2H, s), 5.71 (2H, s), 6.69 (1H, d), 6.82 (1H, s), 6.87 (2H, d), 7.06 (1H, t), 7.11-7.17 (1H, m), 7.33 (2H, d), 7.58-7.64 (1H, m), 7.68 (1H, d), 7.75-7.82 (1H, m), 8.21 (1H, s), 9.80 (1H, br s). |
| 12 | 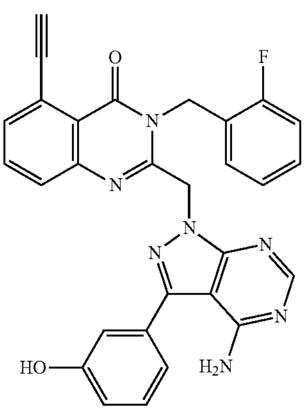 [SMILES: C#Cc1cccc2nc(Cn3nc(-c4cccc(O)c4)c4c(N)ncnc43)n(Cc3ccccc3F)c(=O)c12] | 2-((4-Amino-3-(3-hydroxyphenyl)-1H-pyrazolo[3,4-d]pyrimidin-1-yl)methyl)-5-ethynyl-3-(2-fluorobenzyl) quinazolin-4(3H)-one.<br>$R^t$ 3.63 min; m/z 518 (M + H)$^+$ (ES$^+$);<br>$^1$H NMR (500 MHz, DMSO-d$_6$) δ: 4.42 (1H, s), 5.35 (2H, s), 5.78 (2H, s), 6.35 (1H, t), 6.74 (1H, t), 6.81-6.87 (1H, m), 6.87-6.97 (3H, m), 7.10 (1H, q), 7.21-7.36 (1H, m), 7.62-7.73 (2H, m), 7.76-7.85 (1H, m), 8.19 (1H, s), 9.67 (1H, s). |
| 13 | 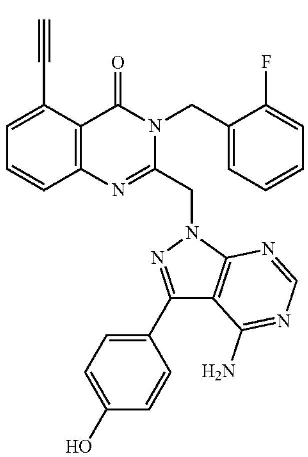 [SMILES: C#Cc1cccc2nc(Cn3nc(-c4ccc(O)cc4)c4c(N)ncnc43)n(Cc3ccccc3F)c(=O)c12] | 2-((4-Amino-3-(4-hydroxyphenyl)-1H-pyrazolo[3,4-d]pyrimidin-1-yl)methyl)-5-ethynyl-3-(2-fluorobenzyl) quinazolin-4(3H)-one.<br>$R^t$ 3.54 min; m/z 518 (M + H)$^+$ (ES$^+$);<br>$^1$H NMR (500 MHz, DMSO-d$_6$) δ: 4.42 (1H, s), 5.34 (2H, s), 5.76 (2H, s), 6.35 (1H, t), 6.72 (1H, t), 6.84-6.93 (3H, m), 7.09 (1H, q), 7.33 (2H, d), 7.64-7.74 (2H, m), 7.76-7.85 (1H, m), 8.17 (1H, s), 9.76 (1H, s). |

TABLE 2-continued

| Example No. | Structure | Name and Analytical Data |
|---|---|---|
| 14 | 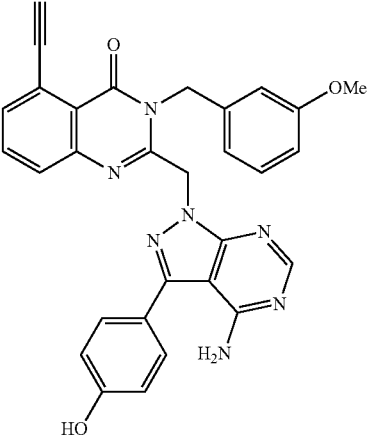 [SMILES: C#Cc1cccc2nc(Cn3nc(-c4ccc(O)cc4)c4c(N)ncnc43)n(Cc3cccc(OC)c3)c(=O)c12] | 2-((4-Amino-3-(4-hydroxyphenyl)-1H-pyrazolo[3,4-d]pyrimidin-1-yl)methyl)-5-ethynyl-3-(3-methoxybenzyl)quinazolin-4(3H)-one.<br>$R^t$ 3.37 min; m/z 530 (M + H)$^+$ (ES$^+$);<br>$^1$H NMR (500 MHz, DMSO-d$_6$) δ: 3.60 (3H, s), 4.44 (1H, s), 5.35 (2H, s), 5.70 (2H, s), 6.34 (1H, d), 6.40 (1H, s), 6.84-6.91 (1H, m), 6.88 (2H, m), 7.00 (1H, t), 7.31-7.38 (2H, m), 7.55 (1H, d), 7.66 (1H, d), 7.75 (1H, t), 8.20 (1H, s), 9.75 (1H, s). |
| 15 | 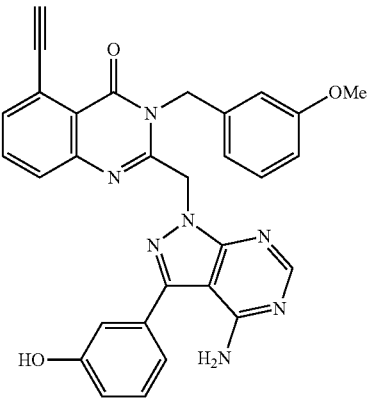 [SMILES: C#Cc1cccc2nc(Cn3nc(-c4cccc(O)c4)c4c(N)ncnc43)n(Cc3cccc(OC)c3)c(=O)c12] | 2-((4-Amino-3-(3-hydroxyphenyl)-1H-pyrazolo[3,4-d]pyrimidin-1-yl)methyl)-5-ethynyl-3-(3-methoxybenzyl)quinazolin-4(3H)-one.<br>$R^t$ 3.48 min; m/z 530 (M + H)$^+$ (ES$^+$);<br>$^1$H NMR (500 MHz, DMSO-d$_6$) δ: 3.61 (3H, s), 4.44 (1H, s), 5.36 (2H, s), 5.73 (2H, s), 6.34 (1H, d), 6.40 (1H, s), 6.68 (1H, dd), 6.82-6.86 (1H, m), 6.93-6.97 (2H, m), 7.00 (1H, t), 7.31 (1H, t), 7.55 (1H, d), 7.67 (1H, d), 7.76 (1H, t), 8.22 (1H, s), 9.67 (1H, s). |
| 16 | 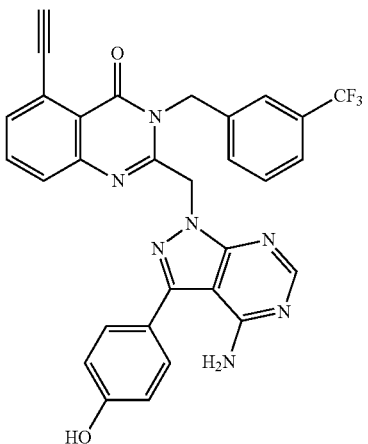 [SMILES: C#Cc1cccc2nc(Cn3nc(-c4ccc(O)cc4)c4c(N)ncnc43)n(Cc3cccc(C(F)(F)F)c3)c(=O)c12] | 2-((4-Amino-3-(4-hydroxyphenyl)-1H-pyrazolo[3,4-d]pyrimidin-1-yl)methyl)-5-ethynyl-3-(3-(trifluoromethyl)benzyl)quinazolin-4(3H)-one.<br>$R^t$ 3.67 min; m/z 568 (M + H)$^+$ (ES$^+$);<br>$^1$H NMR (500 MHz, DMSO-d$_6$) δ: 4.43 (1H, s), 5.44 (2H, s), 5.72 (2H, s), 6.82-6.94 (3H, m), 7.18-7.27 (2H, m), 7.30 (2H, d), 7.43 (1H, d), 7.64 (1H, d), 7.67-7.71 (1H, m), 7.75-7.84 (1H, m), 8.17 (1H, s), 9.75 (1H, s). |

TABLE 2-continued

| Example No. | Structure | Name and Analytical Data |
|---|---|---|
| 17 | 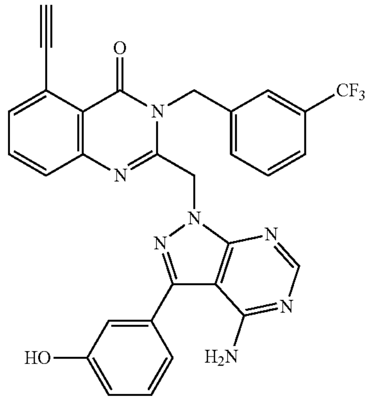 [SMILES: C#Cc1cccc2nc(Cn3nc(-c4cccc(O)c4)c4c(N)ncnc43)n(Cc3cccc(C(F)(F)F)c3)c(=O)c12] | 2-((4-Amino-3-(3-hydroxyphenyl)-1H-pyrazolo[3,4-d]pyrimidin-1-yl)methyl)-5-ethynyl-3-(3-(trifluoromethyl)benzyl)quinazolin-4(3H)-one.<br>R$^t$ 3.76 min; m/z 568 (M + H)$^+$ (ES$^+$);<br>$^1$H NMR (500 MHz, DMSO-d$_6$) δ: 4.44 (1H, s), 5.45 (2H, s), 5.75 (2H, s), 6.82-6.86 (1H, m), 6.89-6.94 (3H, m), 7.22-7.27 (2H, m), 7.30 (1H, t), 7.44 (1H, d), 7.63 (1H, d), 7.68 (1H, d), 7.79 (1H, t), 8.20 (1H, s), 9.67 (1H, s). |
| 18 | 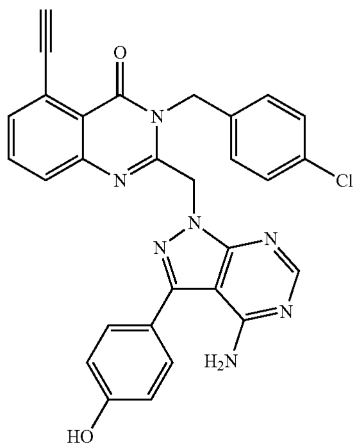 [SMILES: C#Cc1cccc2nc(Cn3nc(-c4ccc(O)cc4)c4c(N)ncnc43)n(Cc3ccc(Cl)cc3)c(=O)c12] | 2-((4-Amino-3-(4-hydroxyphenyl)-1H-pyrazolo[3,4-d]pyrimidin-1-yl)methyl)-3-(4-chlorobenzyl)-5-ethynyl quinazolin-4(3H)-one.<br>R$^t$ 3.56 min; m/z 534/536 (M + H)$^+$ (ES$^+$);<br>$^1$H NMR (500 MHz, DMSO-d$_6$) δ: 4.44 (1H, s), 5.32 (2H, s), 5.70 (2H, s), 6.73 (2H, d), 6.88 (2H, d), 7.05 (2H, d), 7.33 (2H, d), 7.62 (1H, d), 7.68 (1H, d), 7.75-7.84 (1H, m), 8.21 (1H, s), 9.78 (1H, br s). |
| 19 | 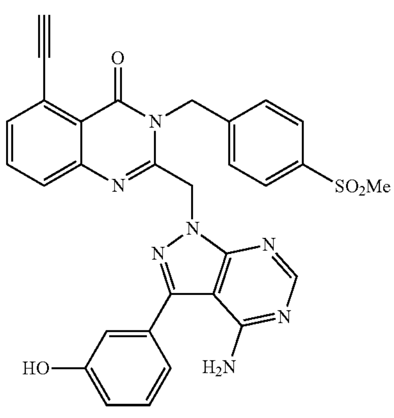 [SMILES: C#Cc1cccc2nc(Cn3nc(-c4cccc(O)c4)c4c(N)ncnc43)n(Cc3ccc(S(C)(=O)=O)cc3)c(=O)c12] | 2-((4-Amino-3-(3-hydroxyphenyl)-1H-pyrazolo[3,4-d]pyrimidin-1-yl)methyl)-5-ethynyl-3-(4-(methylsulfonyl)benzyl)quinazolin-4(3H)-one.<br>R$^t$ 3.27 min; m/z 578 (M + H)$^+$ (ES$^+$);<br>$^1$H NMR (500 MHz, DMSO-d$_6$) δ: 2.99 (3H, s), 4.43 (1H, s), 5.43 (2H, s), 5.76 (2H, s), 6.84 (1H, d), 6.89-6.99 (4H, m), 7.29 (1H, t), 7.56 (2H, d), 7.64-7.72 (2H, m), 7.77-7.85 (1H, m), 8.23 (1H, s), 9.66 (1H, s). |

TABLE 2-continued

| Example No. | Structure | Name and Analytical Data |
|---|---|---|
| 20 | 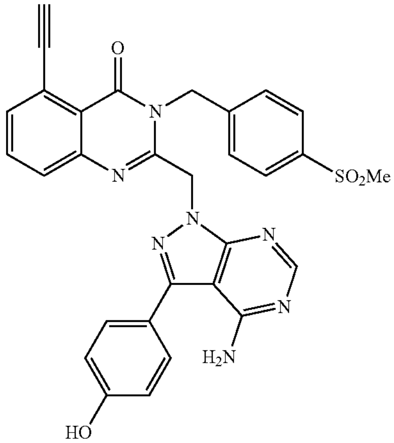 [SMILES: C#Cc1cccc2nc(Cn3nc(-c4ccc(O)cc4)c4c(N)ncnc43)n(Cc3ccc(S(C)(=O)=O)cc3)c(=O)c12] | 2-((4-Amino-3-(4-hydroxyphenyl)-1H-pyrazolo[3,4-d]pyrimidin-1-yl)methyl)-5-ethynyl-3-(4-(methylsulfonyl)benzyl)quinazolin-4(3H)-one.<br>R$^t$ 3.46 min; m/z 578 (M + H)$^+$ (ES$^+$);<br>$^1$H NMR (500 MHz, DMSO-d$_6$) δ: 2.99 (3H, s), 4.42 (1H, s), 5.41 (2H, s), 5.74 (2H, s), 6.81-6.92 (4H, m), 7.30 (2H, d), 7.52 (2H, d), 7.69 (2H, d), 7.78-7.85 (1H, m), 8.22 (1H, s), 9.77 (1H, br s). |
| 21 | 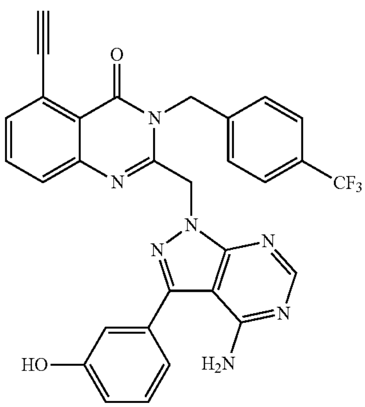 [SMILES: C#Cc1cccc2nc(Cn3nc(-c4cccc(O)c4)c4c(N)ncnc43)n(Cc3ccc(C(F)(F)F)cc3)c(=O)c12] | 2-((4-Amino-3-(3-hydroxyphenyl)-1H-pyrazolo[3,4-d]pyrimidin-1-yl)methyl)-5-ethynyl-3-(4-(trifluoromethyl)benzyl)quinazolin-4(3H)-one.<br>R$^t$ 3.67 min; m/z 568 (M + H)$^+$ (ES$^+$);<br>$^1$H NMR (500 MHz, DMSO-d$_6$) δ: 4.44 (1H, s), 5.42 (2H, s), 5.75 (2H, s), 6.81-6.86 (1H, m), 6.86-6.90 (3H, m), 6.91 (1H, s), 7.29 (1H, t), 7.32 (2H, d), 7.68 (2H, dd), 7.78-7.85 (1H, m), 8.23 (1H, s), 9.65 (1H, s). |
| 22 | 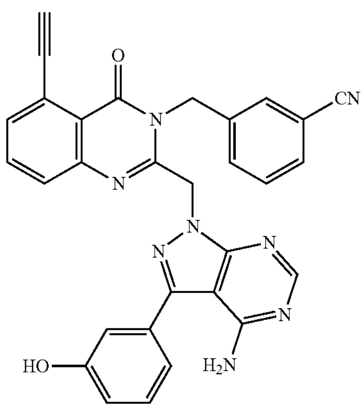 [SMILES: C#Cc1cccc2nc(Cn3nc(-c4cccc(O)c4)c4c(N)ncnc43)n(Cc3cccc(C#N)c3)c(=O)c12] | 3-((2-((4-Amino-3-(4-hydroxyphenyl)-1H-pyrazolo[3,4-d]pyrimidin-1-yl)methyl)-5-ethynyl-4-oxoquinazolin-3(4H)-yl)methyl)benzonitrile.<br>R$^t$ 3.30 min; m/z 525 (M + H)$^+$ (ES$^+$);<br>$^1$H NMR (500 MHz, DMSO-d$_6$) δ: 4.43 (1H, s), 5.35 (2H, s), 5.72 (2H, s), 6.87 (2H, d), 6.95 (1H, d), 7.16 (1H, t), 7.19 (1H, s), 7.32 (2H, d), 7.49 (1H, d), 7.64-7.72 (2H, m), 7.77-7.84 (1H, m), 8.22 (1H, s), 9.76 (1H, br s). |

TABLE 2-continued

| Example No. | Structure | Name and Analytical Data |
|---|---|---|
| 23 | 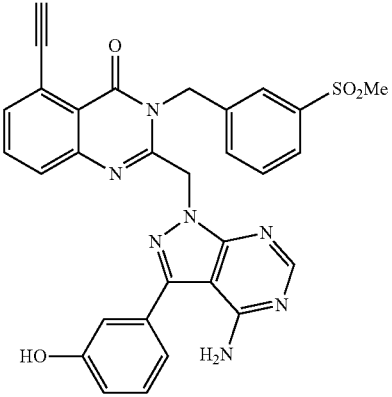 [SMILES: C#Cc1cccc2nc(Cn3nc(-c4cccc(O)c4)c4c(N)ncnc43)n(Cc3cccc(S(C)(=O)=O)c3)c(=O)c12] | 2-((4-Amino-3-(3-hydroxyphenyl)-1H-pyrazolo[3,4-d]pyrimidin-1-yl)methyl)-5-ethynyl-3-(3-(methylsulfonyl)benzyl)quinazolin-4(3H)-one.<br>R$^t$ 3.2 min; m/z 578 (M + H)$^+$ (ES$^+$);<br>$^1$H NMR (500 MHz, DMSO-d$_6$) δ: 3.16 (3H, s), 4.43 (1H, s), 5.47 (2H, s), 5.75 (2H, s), 6.81-6.88 (2H, m), 6.91-6.97 (2H, m), 7.25 (1H, t), 7.30 (1H, t), 7.51 (1H, s), 7.62-7.67 (2H, m), 7.69 (1H, d), 7.77-7.85 (1H, m), 8.21 (1H, s), 9.68 (1H, s). |
| 24 | 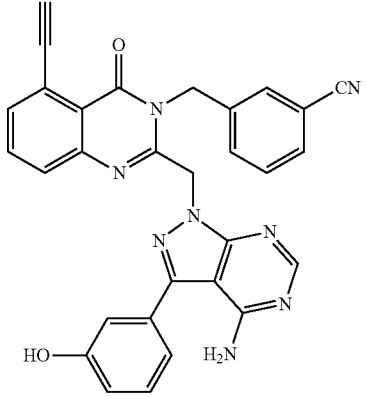 [SMILES: C#Cc1cccc2nc(Cn3nc(-c4cccc(O)c4)c4c(N)ncnc43)n(Cc3cccc(C#N)c3)c(=O)c12] | 3-((2-((4-Amino-3-(3-hydroxyphenyl)-1H-pyrazolo[3,4-d]pyrimidin-1-yl)methyl)-5-ethynyl-4-oxoquinazolin-3(4H)-yl)methyl)benzonitrile.<br>R$^t$ 3.57 min; m/z 525 (M + H)$^+$ (ES$^+$);<br>$^1$H NMR (500 MHz, DMSO-d$_6$) δ: 4.43 (1H, s), 5.37 (2H, s), 5.74 (2H, s), 6.84 (1H, dd), 6.89-6.94 (2H, m), 6.97 (1H, d), 7.19 (1H, t), 7.23 (1H, s), 7.29 (1H, t), 7.52 (1H, d), 7.66 (1H, d), 7.69 (1H, d), 7.77-7.83 (1H, m), 8.24 (1H, s), 9.67 (1H, br s). |
| 25 | 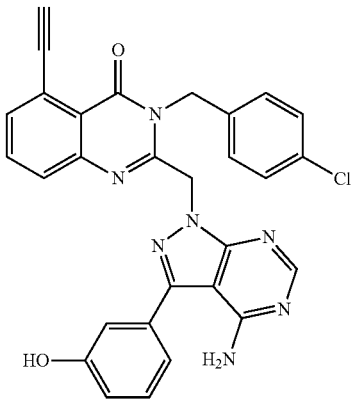 [SMILES: C#Cc1cccc2nc(Cn3nc(-c4cccc(O)c4)c4c(N)ncnc43)n(Cc3ccc(Cl)cc3)c(=O)c12] | 2-((4-Amino-3-(3-hydroxyphenyl)-1H-pyrazolo[3,4-d]pyrimidin-1-yl)methyl)-3-(4-chlorobenzyl)-5-ethynylquinazolin-4(3H)-one.<br>R$^t$ 3.81 min; m/z 534/536 (M + H)$^+$ (ES$^+$);<br>$^1$H NMR (500 MHz, DMSO-d$_6$) δ: 4.44 (1H, s), 5.34 (2H, s), 5.73 (2H, s), 6.78 (2H, d), 6.85 (1H, dd), 6.90-6.97 (2H, m), 7.08 (2H, d), 7.31 (1H, t), 7.60 (1H, d), 7.65-7.70 (1H, m), 7.75-7.80 (1H, m), 8.22 (1H, s), 9.65 (1H, br s). |

TABLE 2-continued

| Example No. | Structure | Name and Analytical Data |
|---|---|---|
| 26 | 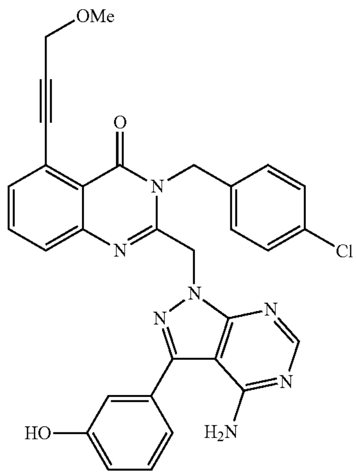 [SMILES: COCC#Cc1cccc2nc(Cn3nc(-c4cccc(O)c4)c4c(N)ncnc43)n(Cc3ccc(Cl)cc3)c(=O)c12] | 2-((4-Amino-3-(3-hydroxyphenyl)-1H-pyrazolo[3,4-d]pyrimidin-1-yl)methyl)-3-(4-chlorobenzyl)-5-(3-methoxyprop-1-ynyl)quinazolin-4(3H)-one.<br>R$^t$ 3.78 min; m/z 578/580 (M + H)$^+$ (ES$^+$);<br>$^1$H NMR (500 MHz, DMSO-d$_6$) δ: 3.34 (3H, s), 4.34 (2H, s), 5.35 (2H, s), 5.73 (2H, s), 6.76 (2H, d), 6.85 (1H, dd), 6.90-6.98 (2H, m), 7.07 (2H, d), 7.31 (1H, t), 7.59 (1H, d), 7.64 (1H, d), 7.73-7.82 (1H, m), 8.30 (1H, br s), 9.67 (1H, s). |
| 27 | 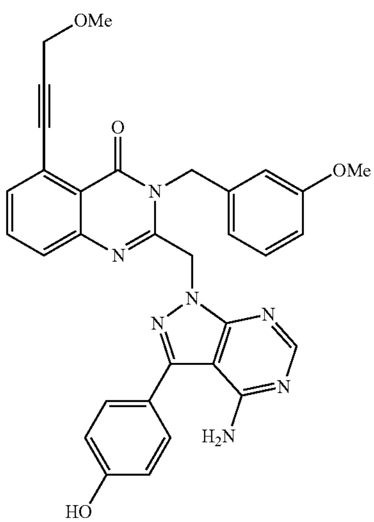 [SMILES: COCC#Cc1cccc2nc(Cn3nc(-c4ccc(O)cc4)c4c(N)ncnc43)n(Cc3cccc(OC)c3)c(=O)c12] | 2-((4-Amino-3-(4-hydroxyphenyl)-1H-pyrazolo[3,4-d]pyrimidin-1-yl)methyl)-3-(3-methoxybenzyl)-5-(3-methoxyprop-1-ynyl)quinazolin-4(3H)-one.<br>R$^t$ 3.50 min; m/z 574 (M + H)$^+$ (ES$^+$);<br>$^1$H NMR (500 MHz, DMSO-d$_6$) δ: 3.60 (3H, s), 4.34 (2H, s), 5.36 (2H, s), 5.70 (2H, s), 6.32 (1H, d), 6.39 (1H, s), 6.67 (1H, dd), 6.88 (2H, d), 6.99 (1H, t), 7.34 (2H, d), 7.54 (1H, d), 7.63 (1H, d), 7.76 (1H, t), 8.26 (1H, br s), 9.75 (1H, s). |
| 28 | 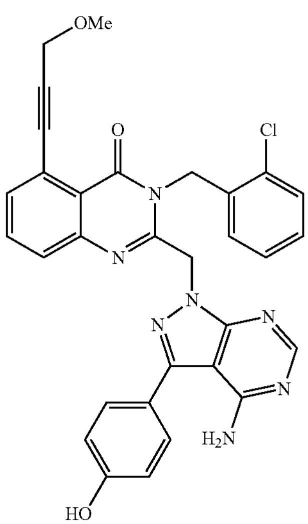 [SMILES: COCC#Cc1cccc2nc(Cn3nc(-c4ccc(O)cc4)c4c(N)ncnc43)n(Cc3ccccc3Cl)c(=O)c12] | 2-((4-Amino-3-(4-hydroxyphenyl)-1H-pyrazolo[3,4-d]pyrimidin-1-yl)methyl)-3-(2-chlorobenzyl)-5-(3-methoxyprop-1-ynyl)quinazolin-4(3H)-one.<br>R$^t$ 3.63 min; m/z 578/580 (M + H)$^+$ (ES$^+$);<br>$^1$H NMR (500 MHz, DMSO-d$_6$) δ: 3.30 (3H, s), 4.30 (2H, s), 5.29 (2H, s), 5.74 (2H, s), 6.17 (1H, d), 6.77 (1H, t), 6.87 (2H, d), 7.02 (1H, t), 7.11 (1H, d), 7.32 (2H, d), 7.67 (1H, d), 7.71-7.75 (1H, m), 7.80-7.86 (1H, m), 8.16 (1H, br s), 9.76 (1H, s). |

TABLE 2-continued

| Example No. | Structure | Name and Analytical Data |
|---|---|---|
| 29 | 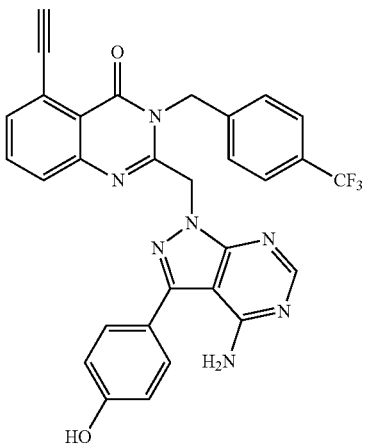 [SMILES: C#Cc1cccc2nc(Cn3nc(-c4ccc(O)cc4)c4c(N)ncnc43)n(Cc3ccc(C(F)(F)F)cc3)c(=O)c12] | 2-((4-Amino-3-(4-hydroxyphenyl)-1H-pyrazolo[3,4-d]pyrimidin-1-yl)methyl)-5-ethynyl-3-(4-(trifluoromethyl)benzyl)quinazolin-4(3H)-one. R$^t$ 3.70 min; m/z 568 (M + H)$^+$ (ES$^+$); $^1$H NMR (500 MHz, DMSO-d$_6$) δ: 4.42 (1H, s), 5.40 (2H, s), 5.73 (2H, s), 6.79-6.90 (4H, m), 7.29 (2H, d), 7.27 (2H, d), 7.67-7.72 (2H, m), 7.82 (1H, t), 8.22 (1H, s), 9.76 (1H, s). |
| 30 | 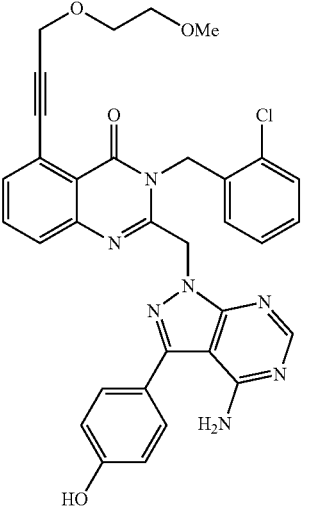 [SMILES: COCCOCC#Cc1cccc2nc(Cn3nc(-c4ccc(O)cc4)c4c(N)ncnc43)n(Cc3ccccc3Cl)c(=O)c12] | 2-((4-Amino-3-(3-hydroxyphenyl)-1H-pyrazolo[3,4-d]pyrimidin-1-yl)methyl)-3-(2-chlorobenzyl)-5-(3-(2-methoxyethoxy)prop-1-ynyl)quinazolin-4(3H)-one. R$^t$ 3.64 min; m/z 623/625 (M + H)$^+$ (ES$^+$); $^1$H NMR (500 MHz, DMSO-d$_6$) δ: 3.18 (3H, s), 3.42 (2H, dd), 3.62 (2H, dd), 4.37 (2H, s), 5.29 (2H, s), 5.74 (2H, s), 6.16 (1H, d), 6.74-6.80 (1H, m), 6.87 (2H, d), 7.02 (1H, t), 7.12 (1H, d), 7.32 (2H, d), 7.66 (1H, dd), 7.73 (1H, dd), 7.83 (1H, t), 8.16 (1H, br s), 9.75 (1H, s). |
| 31 | 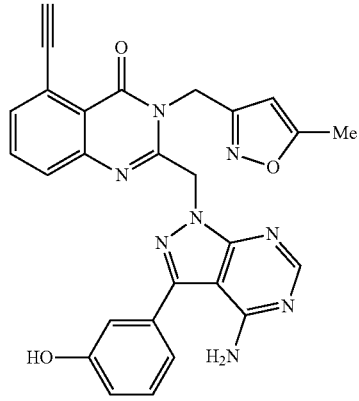 [SMILES: C#Cc1cccc2nc(Cn3nc(-c4cccc(O)c4)c4c(N)ncnc43)n(Cc3cc(C)on3)c(=O)c12] | 2-((4-Amino-3-(3-hydroxyphenyl)-1H-pyrazolo[3,4-d]pyrimidin-1-yl)methyl)-5-ethynyl-3-((5-methylisoxazol-3-yl)methyl)quinazolin-4(3H)-one. R$^t$ 3.33 min; m/z 505 (M + H)$^+$ (ES$^+$); $^1$H NMR (500 MHz, DMSO-d$_6$) δ: 2.26 (3H, s), 4.46 (1H, s), 5.37 (2H, s), 5.83 (2H, s), 5.92 (1H, s), 6.86 (1H, dd), 6.98-7.07 (2H, m), 7.33 (1H, t), 7.50 (1H, d), 7.61-7.68 (1H, m), 7.74 (1H, t), 8.25 (1H, s), 9.69 (1H, s). |

TABLE 2-continued

| Example No. | Structure | Name and Analytical Data |
|---|---|---|
| 32 | 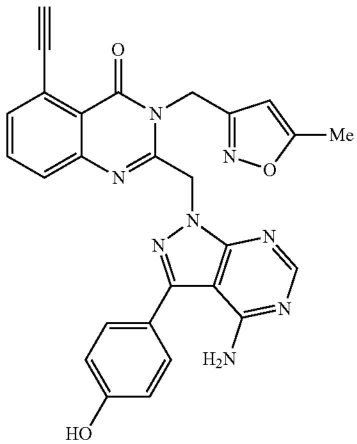 [SMILES: C#Cc1cccc2nc(Cn3nc(-c4ccc(O)cc4)c4c(N)ncnc43)n(Cc3cc(C)on3)c(=O)c12] | 2-((4-Amino-3-(4-hydroxyphenyl)-1H-pyrazolo[3,4-d]pyrimidin-1-yl)methyl)-5-ethynyl-3-((5-methyl isoxazol-3-yl)methyl)quinazolin-4(3H)-one. <br> $R^t$ 3.25 min; m/z 505 (M + H)$^+$ (ES$^+$); <br> $^1$H NMR (500 MHz, DMSO-d$_6$) δ: 2.25 (3H, s), 4.45 (1H, s), 5.37 (2H, s), 5.80 (2H, s), 5.92 (1H, s), 6.90 (2H, d), 7.41 (2H, d), 7.50 (1H, d), 7.62-7.68 (1H, m), 7.70-7.80 (1H, m), 8.22 (1H, s), 9.77 (1H, br s). |
| 33 | 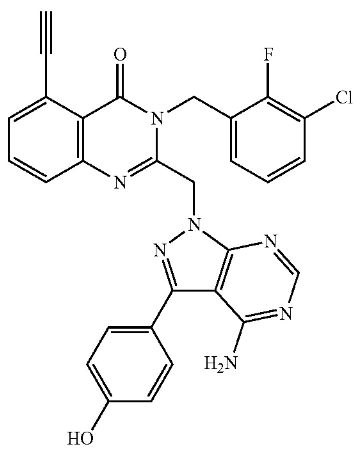 [SMILES: C#Cc1cccc2nc(Cn3nc(-c4ccc(O)cc4)c4c(N)ncnc43)n(Cc3cccc(Cl)c3F)c(=O)c12] | 2-((4-Amino-3-(4-hydroxyphenyl)-1H-pyrazolo[3,4-d]pyrimidin-1-yl)methyl)-3-(3-chloro-2-fluorobenzyl)-5-ethynylquinazolin-4(3H)-one. <br> $R^t$ 3.60 min; m/z 552/554 (M + H)$^+$ (ES$^+$); <br> $^1$H NMR (500 MHz, DMSO-d$_6$) δ: 4.42 (1H, s), 5.34 (2H, s), 5.76 (2H, s), 6.24 (1H, t), 6.61-6.74 (1H, m), 6.87 (2H, d), 7.22 (1H, t), 7.32 (2H, d), 7.66-7.75 (2H, m), 7.81-7.89 (1H, m), 8.19 (1H, s), 9.76 (1H, br s). |
| 34 | 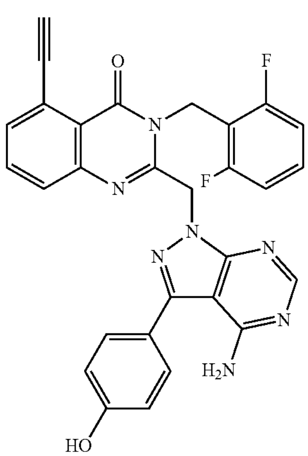 [SMILES: C#Cc1cccc2nc(Cn3nc(-c4ccc(O)cc4)c4c(N)ncnc43)n(Cc3c(F)cccc3F)c(=O)c12] | 2-((4-Amino-3-(4-hydroxyphenyl)-1H-pyrazolo[3,4-d]pyrimidin-1-yl)methyl)-3-(2,6-difluorobenzyl)-5-ethynylquinazolin-4(3H)-one. <br> $R^t$ 3.52 min; m/z 536 (M + H)$^+$ (ES$^+$); <br> $^1$H NMR (500 MHz, DMSO-d$_6$) δ: 4.42 (1H, s), 5.41 (2H, s), 5.86 (2H, s), 6.84-6.92 (4H, m), 7.20-7.31 (1H, m), 7.39 (2H, d), 7.49 (1H, d), 7.63 (1H, d), 7.72 (1H, t), 8.21 (1H, s), 9.79 (1H, br s). |

TABLE 2-continued

| Example No. | Structure | Name and Analytical Data |
|---|---|---|
| 35 | 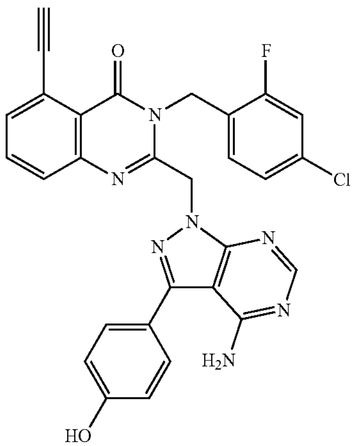 [SMILES: C#Cc1cccc2nc(Cn3nc(-c4ccc(O)cc4)c4c(N)ncnc43)n(Cc3ccc(Cl)cc3F)c(=O)c12] | 2-((4-Amino-3-(4-hydroxyphenyl)-1H-pyrazolo[3,4-d]pyrimidin-1-yl)methyl)-3-(4-chloro-2-fluorobenzyl)-5-ethynylquinazolin-4(3H)-one.<br>R$^t$ 3.59 min; m/z 552/554 (M + H)$^+$ (ES$^+$);<br>$^1$H NMR (500 MHz, DMSO-d$_6$) δ: 4.44 (1H, s), 5.32 (2H, s), 5.77 (2H, s), 6.33-6.39 (1H, m), 6.87 (2H, d), 6.97 (1H, t), 7.11-7.19 (1H, m), 7.35 (2H, d), 7.67-7.73 (2H, m), 7.82 (1H, t), 8.18 (1H, s), 9.77 (1H, br s). |
| 36 | 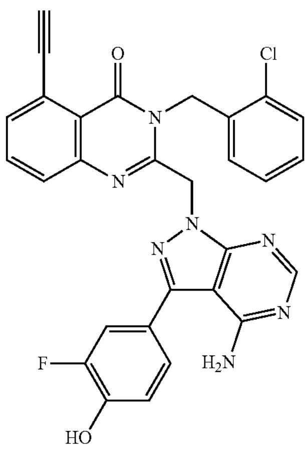 [SMILES: C#Cc1cccc2nc(Cn3nc(-c4ccc(O)c(F)c4)c4c(N)ncnc43)n(Cc3ccccc3Cl)c(=O)c12] | 2-((4-Amino-3-(3-fluoro-4-hydroxyphenyl)-1H-pyrazolo[3,4-d]pyrimidin-1-yl)methyl)-3-(2-chloro benzyl)-5-ethynylquinazolin-4(3H)-one.<br>R$^t$ 3.72 min; m/z 552/554 (M + H)$^+$ (ES$^+$);<br>$^1$H NMR (500 MHz, DMSO-d$_6$) δ: 4.46 (1H, s), 5.35 (2H, s), 5.42 (2H, s), 6.88 (1H, d), 7.20 (1H, t), 7.31 (1H, t), 7.35-7.43 (3H, m), 7.51 (1H, d), 7.73 (1H, d), 7.77 (1H, d), 7.85 (1H, t), 8.21 (1H, s), 13.57 (1H, br s). |
| 37 | 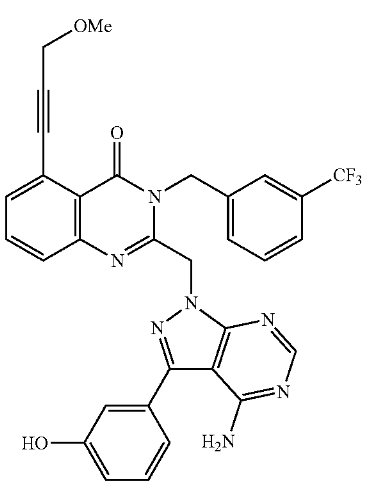 [SMILES: COCC#Cc1cccc2nc(Cn3nc(-c4cccc(O)c4)c4c(N)ncnc43)n(Cc3cccc(C(F)(F)F)c3)c(=O)c12] | 2-((4-Amino-3-(3-hydroxyphenyl)-1H-pyrazolo[3,4-d]pyrimidin-1-yl)methyl)-5-(3-methoxyprop-1-ynyl)-3-(3-(trifluoromethyl)benzyl)quinazolin-4(3H)-one.<br>R$^t$ 4.22 min; m/z 612 (M + H)$^+$ (ES$^+$);<br>$^1$H NMR (500 MHz, DMSO-d$_6$) δ: 3.32 (3H, s), 4.33 (2H, s), 5.45 (2H, s), 5.75 (2H, s), 6.81-6.86 (1H, m), 6.87-6.94 (3H, m), 7.21-7.26 (2H, m), 7.29 (1H, t), 7.43 (1H, d), 7.64 (2H, t), 7.79 (1H, t), 8.24 (1H, br s), 9.68 (1H, s). |

| Example No. | Structure | Name and Analytical Data |
|---|---|---|
| 38 | 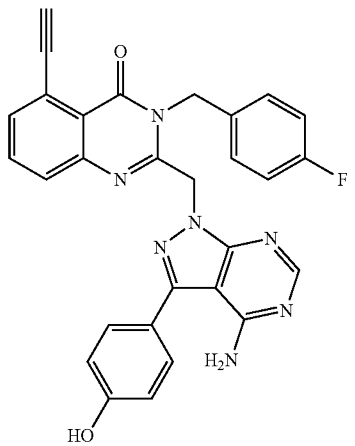 [SMILES: C#Cc1cccc2nc(Cn3nc(-c4ccc(O)cc4)c4c(N)ncnc43)n(Cc3ccc(F)cc3)c(=O)c12] | 2-((4-Amino-3-(4-hydroxyphenyl)-1H-pyrazolo[3,4-d]pyrimidin-1-yl)methyl)-5-ethynyl-3-(4-fluorobenzyl)quinazolin-4(3H)-one.<br>R$^t$ 3.47 min; m/z 518 (M + H)$^+$ (ES$^+$);<br>$^1$H NMR (500 MHz, DMSO-d$_6$) δ: 4.45 (1H, s), 5.34 (2H, s), 5.71 (2H, s), 6.80-6.90 (6H, m), 7.34 (2H, d), 7.55-7.62 (1H, m), 7.67 (1H, dd), 7.77 (1H, t), 8.21 (1H, s), 9.79 (1H, s). |
| 39 | 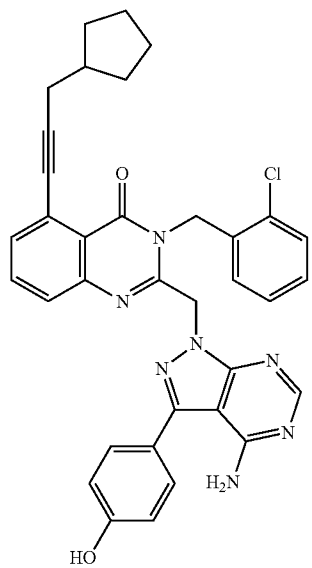 [SMILES: Nc1ncnc2c1c(-c1ccc(O)cc1)nn2Cc1nc2cccc(C#CCC3CCCC3)c2c(=O)n1Cc1ccccc1Cl] | 2-((4-Amino-3-(4-hydroxyphenyl)-1H-pyrazolo[3,4-d]pyrimidin-1-yl)methyl)-3-(2-chlorobenzyl)-5-(3-cyclopentylprop-1-ynyl)quinazolin-4(3H)-one.<br>R$^t$ 4.66 min; m/z 616/618 (M + H)$^+$ (ES$^+$);<br>$^1$H NMR (500 MHz, DMSO-d$_6$) δ: 1.21-1.34 (2H, m), 1.41-1.50 (2H, m), 1.51-1.61 (2H, m), 1.68-1.77 (2H, m), 1.99-2.10 (1H, m), 2.41 (2H, d), 5.27 (2H, s), 5.73 (2H, s), 6.15 (1H, d), 6.77 (1H, t), 6.87 (2H, d), 6.99-7.05 (1H, m), 7.11 (1H, d), 7.32 (2H, d), 7.58 (1H, d), 7.64-7.70 (1H, m), 7.75-7.82 (1H, m), 8.16 (1H, br s), 9.77 (1H, s). |
| 40 | 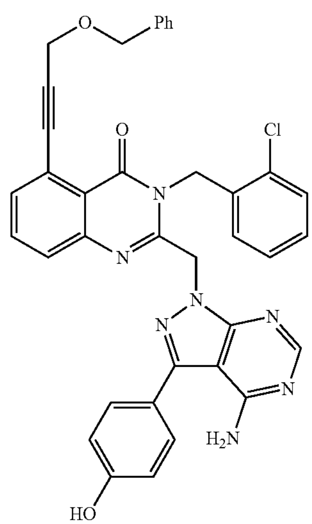 [SMILES: Nc1ncnc2c1c(-c1ccc(O)cc1)nn2Cc1nc2cccc(C#CCOCc3ccccc3)c2c(=O)n1Cc1ccccc1Cl] | 2-((4-Amino-3-(4-hydroxyphenyl)-1H-pyrazolo[3,4-d]pyrimidin-1-yl)methyl)-5-(3-(benzyloxy)prop-1-ynyl)-3-(2-chlorobenzyl)quinazolin-4(3H)-one.<br>R$^t$ 4.25 min; m/z 654/656 (M + H)$^+$ (ES$^+$);<br>$^1$H NMR (500 MHz, DMSO-d$_6$) δ: 4.41 (2H, s), 4.60 (2H, s), 5.31 (2H, s), 5.76 (2H, s), 6.17 (1H, d), 6.76 (1H, t), 6.87 (2H, d), 6.99-7.05 (1H, m), 7.13 (1H, d), 7.25 (5H, s), 7.32 (2H, d), 7.67 (1H, d), 7.75 (1H, d), 7.81-7.87 (1H, m), 8.16 (1H, s), 9.77 (1H, s). |

TABLE 2-continued

| Example No. | Structure | Name and Analytical Data |
|---|---|---|
| 41 | 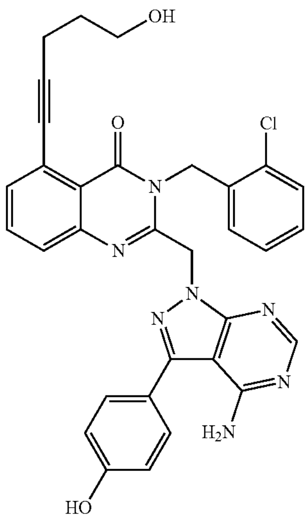 [SMILES: Nc1ncnc2c1c(-c1ccc(O)cc1)nn2Cc1nc2cccc(C#CCCCO)c2c(=O)n1Cc1ccccc1Cl] | 2-((4-Amino-3-(4-hydroxyphenyl)-1H-pyrazolo[3,4-d]pyrimidin-1-yl)methyl)-3-(2-chlorobenzyl)-5-(5-hydroxypent-1-ynyl)quinazolin-4(3H)-one.<br>R$^t$ 3.37 min; m/z 592/594 (M + H)$^+$ (ES$^+$);<br>$^1$H NMR (500 MHz, DMSO-d$_6$) δ: 1.65 (2H, quin), 2.44 (2H, t), 3.48 (2H, q), 4.48 (1H, t), 5.28 (2H, s), 5.72 (2H, s), 6.14 (1H, d), 6.77 (1H, t), 6.87 (2H, d), 7.02 (1H, t), 7.11 (1H, d), 7.32 (2H, d), 7.59 (1H, d), 7.64-7.69 (1H, m), 7.79 (1H, t), 8.16 (1H, s), 9.77 (1H, s). |
| 42 | 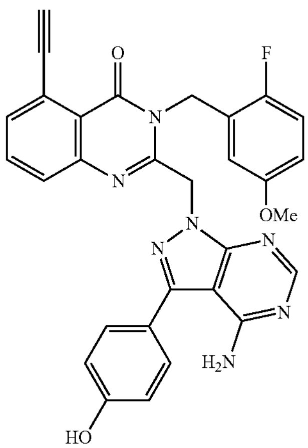 [SMILES: C#Cc1cccc2nc(Cn3nc(-c4ccc(O)cc4)c4c(N)ncnc43)n(Cc3cc(OC)ccc3F)c(=O)c12] | 2-((4-Amino-3-(4-hydroxyphenyl)-1H-pyrazolo[3,4-d]pyrimidin-1-yl)methyl)-5-ethynyl-3-(2-fluoro-5-methoxybenzyl)quinazolin-4(3H)-one.<br>R$^t$ 3.47 min; m/z 548 (M + H)$^+$ (ES$^+$);<br>$^1$H NMR (500 MHz, DMSO-d$_6$) δ: 3.38 (3H, s), 4.44 (1H, s), 5.31 (2H, s), 5.76 (2H, s), 5.78 (1H, dd), 6.59-6.64 (1H, m), 6.83 (1H, t), 6.87 (2H, d), 7.31 (2H, m), 7.65-7.71 (2H, m), 7.77-7.84 (1H, m), 8.17 (1H, s), 9.77 (1H, s). |
| 43 | 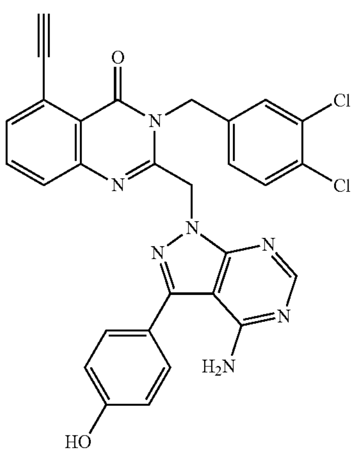 [SMILES: C#Cc1cccc2nc(Cn3nc(-c4ccc(O)cc4)c4c(N)ncnc43)n(Cc3ccc(Cl)c(Cl)c3)c(=O)c12] | 2-((4-Amino-3-(4-hydroxyphenyl)-1H-pyrazolo[3,4-d]pyrimidin-1-yl)methyl)-3-(3,4-dichlorobenzyl)-5-ethynylquinazolin-4(3H)-one.<br>R$^t$ 3.73 min; m/z 568/570 (M + H)$^+$ (ES$^+$);<br>$^1$H NMR (500 MHz, DMSO-d$_6$) δ: 4.45 (1H, s), 5.30 (2H, s), 5.72 (2H, s), 6.61 (1H, dd), 6.87 (2H, d), 6.90-6.95 (1H, m), 7.19 (1H, d), 7.30 (2H, d), 7.65-7.72 (2H, m), 7.77-7.84 (1H, m), 8.23 (1H, s), 9.78 (1H, br s). |

| Example No. | Structure | Name and Analytical Data |
| --- | --- | --- |
| 44 | 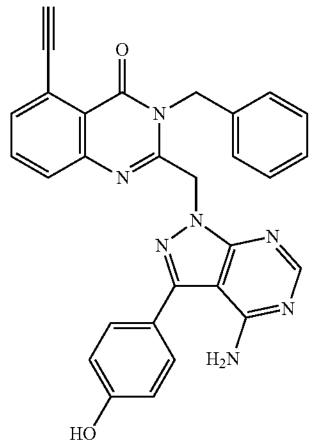 [SMILES: C#Cc1cccc2nc(Cn3nc(-c4ccc(O)cc4)c4c(N)ncnc43)n(Cc3ccccc3)c(=O)c12] | 2-((4-Amino-3-(4-hydroxyphenyl)-1H-pyrazolo[3,4-d]pyrimidin-1-yl)methyl)-3-benzyl-5-ethynylquinazolin-4(3H)-one.<br>$R^t$ 3.39 min; m/z 500 (M + H)$^+$ (ES$^+$);<br>$^1$H NMR (500 MHz, DMSO-d$_6$) δ: 4.45 (1H, s), 5.38 (2H, s), 5.70 (2H, s), 6.83 (2H, d), 6.88 (2H, d), 7.06-7.14 (3H, m), 7.34 (2H, d), 7.55 (1H, d), 7.64-7.68 (1H, m), 7.73-7.79 (1H, m), 8.19 (1H, s), 9.77 (1H, s). |
| 45 | 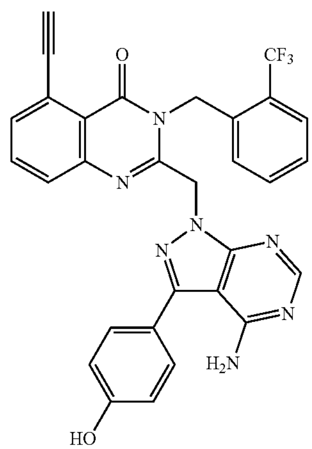 [SMILES: C#Cc1cccc2nc(Cn3nc(-c4ccc(O)cc4)c4c(N)ncnc43)n(Cc3ccccc3C(F)(F)F)c(=O)c12] | 2-((4-Amino-3-(4-hydroxyphenyl)-1H-pyrazolo[3,4-d]pyrimidin-1-yl)methyl)-5-ethynyl-3-(2-trifluoromethyl benzyl)quinazolin-4(3H)-one.<br>$R^t$ 3.74 min; m/z 568 (M + H)$^+$ (ES$^+$);<br>$^1$H NMR (500 MHz, DMSO-d$_6$) δ: 4.42 (1H, s), 5.47 (2H, s), 5.74 (2H, s), 6.37 (1H, d), 6.88 (2H, d), 7.11 (1H, t), 7.25 (1H, t), 7.34 (2H, d), 7.50 (1H, d), 7.69 (1H, d), 7.71-7.75 (1H, m), 7.83 (1H, t), 8.09 (1H, s), 9.80 (1H, br s). |
| 46 | 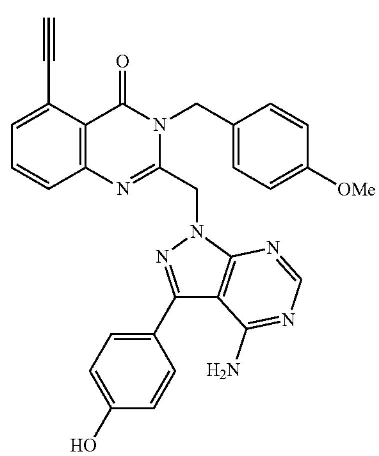 [SMILES: C#Cc1cccc2nc(Cn3nc(-c4ccc(O)cc4)c4c(N)ncnc43)n(Cc3ccc(OC)cc3)c(=O)c12] | 2-((4-Amino-3-(4-hydroxyphenyl)-1H-pyrazolo[3,4-d]pyrimidin-1-yl)methyl)-5-ethynyl-3-(4-methoxy benzyl)quinazolin-4(3H)-one.<br>$R^t$ 3.39 min; m/z 530 (M + H)$^+$ (ES$^+$);<br>$^1$H NMR (500 MHz, DMSO-d$_6$) δ: 3.65 (3H, s), 4.46 (1H, s), 5.31 (2H, s), 5.71 (2H, s), 6.68 (2H, d), 6.81 (2H, d), 6.88 (2H, d), 7.35 (2H, d), 7.48-7.55 (1H, m), 7.63-7.68 (1H, m), 7.71-7.78 (1H, m), 8.21 (1H, s), 9.78 (1H, s). |

TABLE 2-continued

| Example No. | Structure | Name and Analytical Data |
|---|---|---|
| 47 | 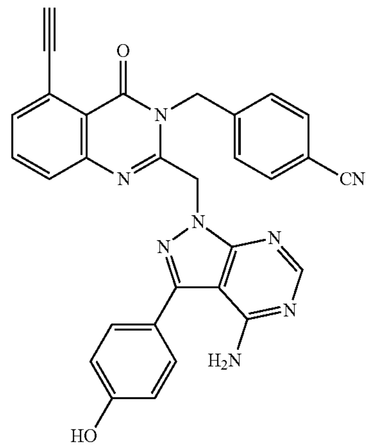 [SMILES: C#Cc1cccc2nc(Cn3nc(-c4ccc(O)cc4)c4c(N)ncnc43)n(Cc3ccc(C#N)cc3)c(=O)c12] | 4-((2-((4-Amino-3-(4-hydroxyphenyl)-1H-pyrazolo[3,4-d]pyrimidin-1-yl)methyl)-5-ethynyl-4-oxoquinazolin-3(4H)-yl)methyl)benzonitrile.<br>R$^t$ 3.37 min; m/z 525 (M + H)$^+$ (ES$^+$);<br>$^1$H NMR (500 MHz, DMSO-d$_6$) δ: 4.44 (1H, s), 5.38 (2H, s), 5.71 (2H, s), 6.79 (2H, d), 6.87 (2H, d), 7.30 (2H, d), 7.37 (2H, d), 7.64-7.75 (2H, m), 7.78-7.88 (1H, m), 8.21 (1H, s), 9.80 (1H, br s). |
| 48 | 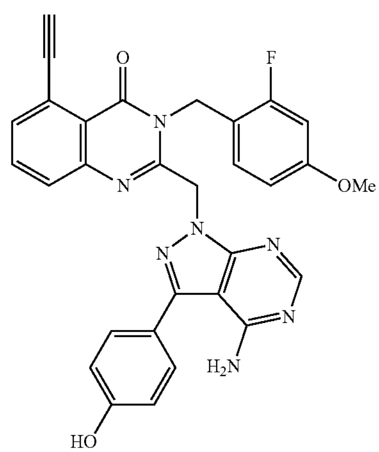 [SMILES: C#Cc1cccc2nc(Cn3nc(-c4ccc(O)cc4)c4c(N)ncnc43)n(Cc3ccc(OC)cc3F)c(=O)c12] | 2-((4-Amino-3-(4-hydroxyphenyl)-1H-pyrazolo[3,4-d]pyrimidin-1-yl)methyl)-5-ethynyl-3-(2-fluoro-4-methoxybenzyl)quinazolin-4(3H)-one.<br>R$^t$ 3.50 min; m/z 548 (M + H)$^+$ (ES$^+$);<br>$^1$H NMR (500 MHz, DMSO-d$_6$) δ: 3.62 (3H, s) 4.44 (1H, s) 5.25 (2H, s) 5.75 (2H, s) 6.27-6.35 (2H, m) 6.49-6.56 (1H, m) 6.88 (2H, d) 7.33 (2H, d) 7.60-7.70 (2H, m) 7.75-7.83 (1H, m) 8.19 (1H, s) 9.80 (1H, br s). |
| 49 | 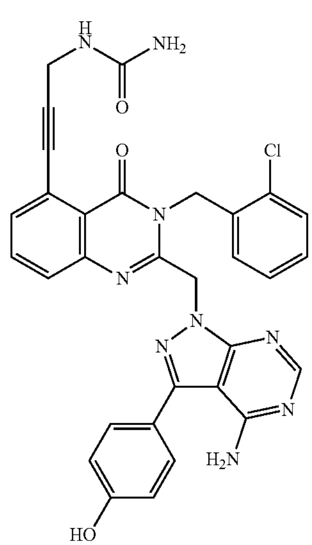 [SMILES: NC(=O)NCC#Cc1cccc2nc(Cn3nc(-c4ccc(O)cc4)c4c(N)ncnc43)n(Cc3ccccc3Cl)c(=O)c12] | 1-(3-(2-((4-Amino-3-(4-hydroxyphenyl)-1H-pyrazolo[3,4-d]pyrimidin-1-yl)methyl)-3-(2-chloro benzyl)-4-oxo-3,4-dihydroquinazolin-5-yl)prop-2-ynyl)urea.<br>R$^t$ 3.02 min; m/z 606/608 (M + H)$^+$ (ES$^+$);<br>$^1$H NMR (500 MHz, DMSO-d$_6$) δ: 4.02 (2H, d), 5.28 (2H, s), 5.58 (2H, s), 5.74 (2H, br s), 6.13 (1H, d), 6.27-6.33 (1H, m), 6.72-6.79 (1H, m), 6.87 (2H, d), 6.99-7.05 (1H, m), 7.08-7.13 (1H, m), 7.31 (2H, d), 7.59-7.64 (1H, m), 7.72 (1H, d), 7.82 (1H, t), 8.16 (1H, br s), 9.77 (1H, s). |

| Example No. | Structure | Name and Analytical Data |
|---|---|---|
| 50 | 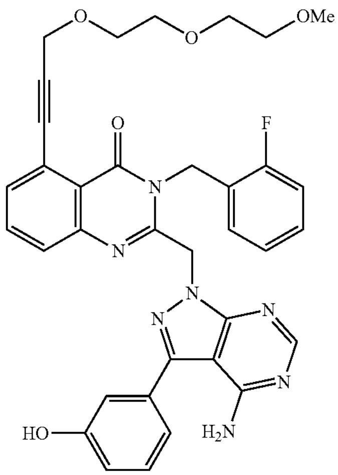 [SMILES: COCCOCCOCC#Cc1cccc2nc(Cn3nc(-c4cccc(O)c4)c4c(N)ncnc43)n(Cc3ccccc3F)c(=O)c12] | 2-((4-Amino-3-(3-hydroxyphenyl)-1H-pyrazolo[3,4-d]pyrimidin-1-yl)methyl)-3-(2-fluorobenzyl)-5-(3-(2-(2-methoxyethoxy)ethoxy)prop-1-ynyl)quinazolin-4(3H)-one.<br>$R^t$ 3.58 min; m/z 650 (M + H)$^+$ (ES$^+$);<br>$^1$H NMR (500 MHz, DMSO-d$_6$) δ: 3.19 (3H, s), 3.37-3.39 (2H, m), 3.46 (2H, dd), 3.51 (2H, dd), 3.63 (2H, dd), 4.39 (2H, s), 5.35 (2H, s), 5.78 (2H, s), 6.29-6.36 (1H, m), 6.69-6.75 (1H, m), 6.82-6.86 (1H, m), 6.86-6.95 (3H, m), 7.05-7.12 (1H, m), 7.30 (1H, t), 7.64-7.69 (2H, m), 7.78-7.83 (1H, m), 8.20 (1H, s), 9.68 (1H, s). |
| 51 | 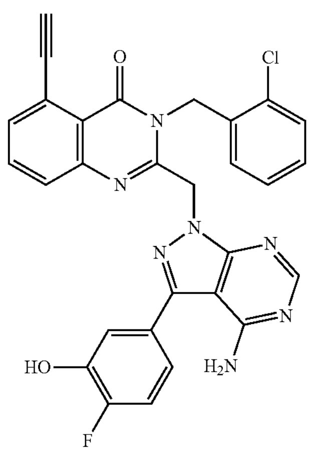 [SMILES: C#Cc1cccc2nc(Cn3nc(-c4ccc(F)c(O)c4)c4c(N)ncnc43)n(Cc3ccccc3Cl)c(=O)c12] | 2-((4-Amino-3-(4-fluoro-3-hydroxyphenyl)-1H-pyrazolo[3,4-d]pyrimidin-1-yl)methyl)-3-(2-chlorobenzyl)-5-ethynylquinazolin-4(3H)-one.<br>$R^t$ 3.79 min; m/z 552/554 (M + H)$^+$ (ES$^+$);<br>$^1$H NMR (500 MHz, DMSO-d$_6$) δ: 4.46 (1H, s), 5.35 (2H, s), 5.38 (2H, s), 6.89 (1H, d), 7.13-7.35 (4H, m), 7.45-7.53 (2H, m), 7.67-7.73 (2H, d), 7.78-7.85 (1H, m), 8.21 (1H, s), 13.59 (1H, s). |
| 52 | 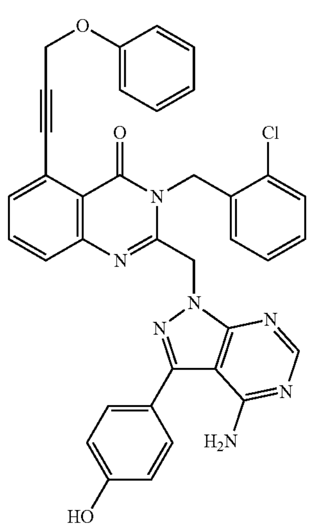 [SMILES: Nc1ncnc2c1c(-c1ccc(O)cc1)nn2Cc1nc2cccc(C#CCOc3ccccc3)c2c(=O)n1Cc1ccccc1Cl] | 2-((4-Amino-3-(4-hydroxyphenyl)-1H-pyrazolo[3,4-d]pyrimidin-1-yl)methyl)-3-(2-chlorobenzyl)-5-(3-phenoxyprop-1-ynyl)quinazolin-4(3H)-one.<br>$R^t$ 4.25 min; m/z 640/642 (M + H)$^+$ (ES$^+$);<br>$^1$H NMR (500 MHz, DMSO-d$_6$) δ: 5.00 (2H, s), 5.30 (2H, s), 5.75 (2H, s), 6.15 (1H, d), 6.76 (1H, t), 6.87 (2H, d), 6.92 (1H, t), 7.00-7.06 (3H, m), 7.12 (1H, d), 7.21-7.27 (2H, m), 7.32 (2H, d), 7.62 (1H, d), 7.71-7.78 (1H, m), 7.83 (1H, t), 8.15 (1H, s), 9.78 (1H, br s). |

| Example No. | Structure | Name and Analytical Data |
|---|---|---|
| 53 | 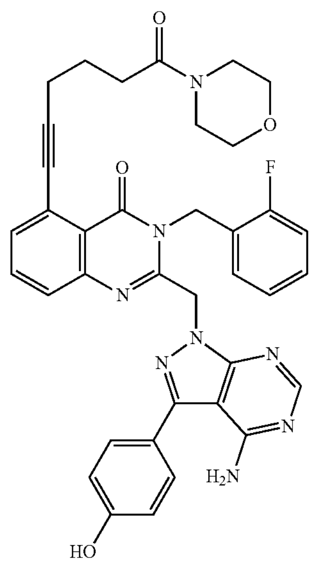 [SMILES: Nc1ncnc2c1c(-c1ccc(O)cc1)nn2Cc1nc2cccc(C#CCCCC(=O)N3CCOCC3)c2c(=O)n1Cc1ccccc1F] | 2-((4-Amino-3-(4-hydroxyphenyl)-1H-pyrazolo[3,4-d]pyrimidin-1-yl)methyl)-3-(2-fluorobenzyl)-5-(6-morpholino-6-oxohex-1-yn-1-yl)quinazolin-4(3H)-one R$^t$ 3.60 min; m/z 673 (M + H)$^+$ (ES$^+$); $^1$H NMR (500 MHz, DMSO-d$_6$) δ: 1.68-1.76 (2H, m), 2.45-2.48 (2H, m), 2.53-2.58 (2H, m), 3.27 (2H, d), 3.30-3.33 (4H, m), 3.41-3.49 (2H, m), 5.34 (2H, s), 5.74 (2H, s), 6.30 (1H, t), 6.70 (1H, t), 6.82-6.91 (3H, m), 7.07 (1H, q), 7.32 (2H, d), 7.62 (1H, d), 7.59 (1H, d), 7.74-7.81 (1H, m), 8.18 (1H, s), 9.76 (1H, s). |
| 54 | 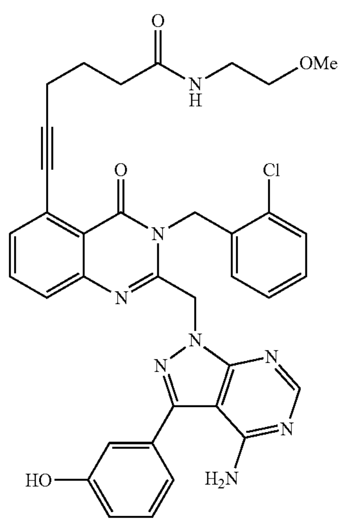 [SMILES: COCCNC(=O)CCCC#Cc1cccc2nc(Cn3nc(-c4cccc(O)c4)c4c(N)ncnc43)n(Cc3ccccc3Cl)c(=O)c12] | 6-(2-((4-Amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N-(2-methoxyethyl)hex-5-ynamide. R$^t$ 3.59 min; m/z 677/679 (M + H)$^+$ (ES$^+$); 1H NMR (500 MHz, DMSO-d$_6$) δ: 1.71 (2H, quin), 2.21 (2H, t), 2.39 (2H, t), 3.13 (2H, q), 3.18 (3H, s), 3.23-3.27 (2H, m), 5.29 (2H, s), 5.75 (2H, s), 6.14 (1H, d), 6.78 (1H, t), 6.81-6.86 (1H, m), 6.89-6.94 (2H, m), 7.03 (1H, t), 7.12 (1H, d), 7.26-7.33 (1H, m), 7.62 (1H, d), 7.68 (1H, d), 7.76-7.86 (2H, m), 8.18 (1H, br s), 9.69 (1H, s). |
| 55 | 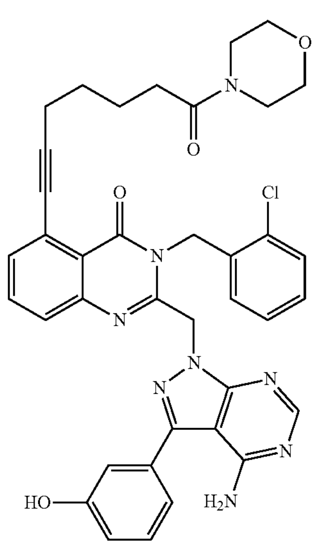 [SMILES: Nc1ncnc2c1c(-c1cccc(O)c1)nn2Cc1nc2cccc(C#CCCCCC(=O)N3CCOCC3)c2c(=O)n1Cc1ccccc1Cl] | 2-((4-Amino-3-(3-hydroxyphenyl)-1H-pyrazolo[3,4-d]pyrimidin-1-yl)methyl)-3-(2-chlorobenzyl)-5-(7-morpholino-7-oxohept-1-yn-1-yl)quinazolin-4(3H)-one. R$^t$ 3.75 min; m/z 703/705 (M + H)$^+$ (ES$^+$); 1H NMR (500 MHz, DMSO-d$_6$) δ: 1.49-1.56 (2H, m), 1.56-1.65 (2H, m), 2.29 (2H, t), 2.42 (2H, t), 3.37-3.43 (4 H, m), 3.45-3.53 (4 H, m), 5.28 (2H, s), 5.75 (2H, br s), 6.13 (1H, d), 6.78 (1H, t), 6.81-6.87 (1H, m), 6.89-6.95 (2H, m), 7.03 (1H, t), 7.12 (1H, d), 7.30 (1H, t), 7.58 (1H, d), 7.67 (1H, d), 7.79 (1H, t), 8.21 (1H, br s), 9.68 (1H, s). |

TABLE 2-continued

| Example No. | Structure | Name and Analytical Data |
|---|---|---|
| 56 | 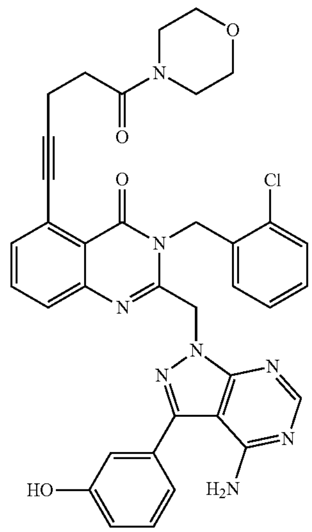 [SMILES: Nc1ncnc2c1c(-c1cccc(O)c1)nn2Cc1nc2cccc(C#CCCC(=O)N3CCOCC3)c2c(=O)n1Cc1ccccc1Cl] | 2-((4-Amino-3-(3-hydroxyphenyl)-1H-pyrazolo[3,4-d]pyrimidin-1-yl)methyl)-3-(2-chlorobenzyl)-5-(5-morpholino-5-oxohept-1-yn-1-yl)quinazolin-4(3H)-one. R$^t$ 3.54 min; m/z 675/677 (M + H)+ (ES)+; $^1$H NMR (500 MHz, DMSO-d$_6$) δ: 2.56-2.67 (4 H, m), 3.37-3.14 (4 H, m), 3.43-3.50 (4 H, m), 5.28 (2H, s), 5.75 (2H, s), 6.12 (1H, d), 6.77 (1H, t), 6.81-6.86 (1H, m), 6.89-6.95 (2H, m), 7.03 (1H, t), 7.12 (1H, d), 7.30 (1H, t), 7.57 (1H, d), 7.68 (1H, d), 7.80 (1H, t), 8.18 (1H, br s), 9.68 (1H, s). |
| 57 | 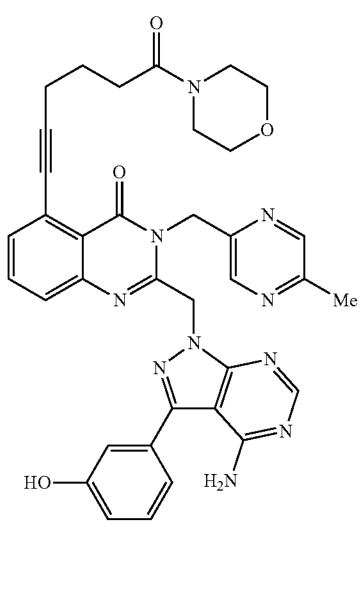 [SMILES: Cc1cnc(Cn2c(Cn3nc(-c4cccc(O)c4)c4c(N)ncnc43)nc3cccc(C#CCCCC(=O)N4CCOCC4)c3c2=O)cn1] | 2-((4-Amino-3-(3-hydroxyphenyl)-1H-pyrazolo[3,4-d]pyrimidin-1-yl)methyl)-3-((5-methylpyrazin-2-yl)methyl)-5-(6-morpholino-5-oxohex-1-yn-1-yl)quinazolin-4(3H)-one. R$^t$ 3.31 min; m/z 671 (M + H)$^+$ (ES$^+$); $^1$H NMR (500 MHz, DMSO-d$_6$) δ: 1.72 (2H, quin), 2.35 (3H, s), 2.45-2.48 (2H, m), 2.54 (2H, br s), 3.25-3.29 (2H, m), 3.31-3.36 (4 H, m), 3.43-3.49 (2H, m), 5.46 (2H, s), 5.81 (2H, s), 6.86 (1H, dd), 6.91-6.98 (2H, m), 7.32 (1H, t), 7.53-7.57 (2H, m), 7.69-7.77 (1H, m), 8.08 (1H, s), 8.11 (1H, s), 8.23 (1H, br s), 9.71 (1H, s). |

TABLE 2-continued

| Example No. | Structure | Name and Analytical Data |
|---|---|---|
| 58 | 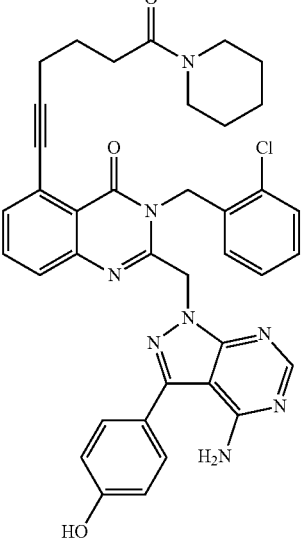 | 2-((4-Amino-3-(4-hydroxyphenyl)-1H-pyrazolo[3,4-d]pyrimidin-1-yl)methyl)-3-(2-chlorobenzyl)-5-(6-oxo-6-(piperidin-1-yl)hex-1-yn-1-yl)quinazolin-4(3H)-one. R$^t$ 4.08 min; m/z 687/689 (M + H)$^+$ (ES$^+$); $^1$H NMR (500 MHz, DMSO-d$_6$) δ: 1.14-1.23 (2H, m), 1.25-1.34 (2H, m), 1.37-1.46 (2H, m), 1.67 (2H, quin), 2.43-2.47 (2H, m), 2.52-2.55 (2H, m), 3.07-3.15 (2H, m), 3.24-3.30 (2H, m), 5.27 (2H, s), 5.72 (2H, s), 6.14 (1H, d), 6.76 (1H, t), 6.86 (2H, d), 7.01 (1H, t), 7.09 (1H, d), 7.31 (2H, d), 7.59 (1H, d), 7.68 (1H, d), 7.79 (1H, t), 8.16 (1H, s), 9.76 (1H, s). |
| 59 | 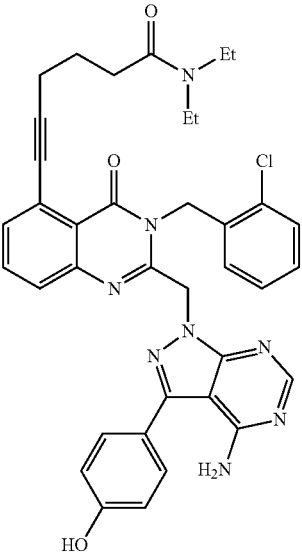 [SMILES: CCN(CC)C(=O)CCCC#Cc1cccc2nc(Cn3nc(-c4ccc(O)cc4)c4c(N)ncnc43)n(Cc3ccccc3Cl)c(=O)c12] | 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-diethylhex-5-ynamide. R$^t$ 4.01 min; m/z 675/677 (M + H)$^+$ (ES$^+$); $^1$H NMR (500 MHz, DMSO-d$_6$) δ: 0.85 (3H, t), 0.89 (3H, t), 1.69 (2H, quin), 2.44-2.48 (2H, m), 2.52-2.53 (2H, m), 3.04 (2H, q), 3.14 (2H, q), 5.27 (2H, s), 5.73 (2H, s), 6.14 (1H, d), 6.75 (1H, t), 6.87 (2H, d), 7.01 (1H, t), 7.09 (1H, d), 7.31 (2H, d), 7.60 (1H, d), 7.68 (1H, d), 7.80 (1H, t), 8.15 (1H, s), 9.77 (1H, br s). |
| 60 | 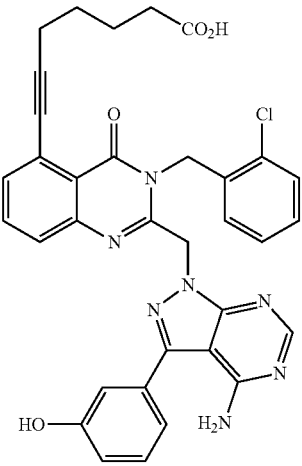 [SMILES: Nc1ncnc2c1c(-c1cccc(O)c1)nn2Cc1nc2cccc(C#CCCCCC(=O)O)c2c(=O)n1Cc1ccccc1Cl] | 7-(2-((4-Amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)hept-6-ynoic acid. R$^t$ 3.80 min; m/z 634/636 (M + H)$^+$ (ES$^+$); $^1$H NMR (500 MHz, DMSO-d$_6$) δ: 1.47-1.56 (2H, m), 1.60 (2H, quin), 2.20 (2H, t), 2.41 (2H, t), 5.28 (2H, s), 5.75 (2H, s), 6.13 (1H, d), 6.78 (1H, t), 6.83 (1H, dd), 6.90-6.94 (2H, m), 7.03 (1H, t), 7.12 (1H, d), 7.30 (1H, t), 7.59 (1H, d), 7.64-7.69 (1H, m), 7.76-7.82 (1H, m), 8.17 (1H, s). |

TABLE 2-continued

| Example No. | Structure | Name and Analytical Data |
|---|---|---|
| 61 | 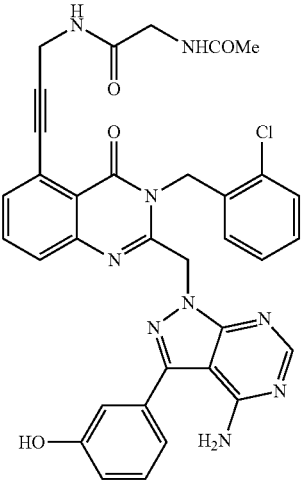 | 2-Acetamido-N-(3-(2-((4-amino-3-(3-hydroxyphenyl)-1H-pyrazolo[3,4-d]pyrimidin-1-yl)methyl)-3-(2-chloro benzyl)-4-oxo-3,4-dihydroquinazolin-5-yl)prop-2-yn-1-yl)acetamide.<br>R$^t$ 3.25 min; m/z 663/665 (M + H)$^+$ (ES$^+$);<br>$^1$H NMR (500 MHz, DMSO-d$_6$) δ: 1.82 (3H, s), 3.65 (2H, d), 4.11 (2H, d), 5.29 (2H, s), 5.76 (2H, s), 6.12 (1H, d), 6.77 (1H, t), 6.81-6.86 (1H, m), 6.89-6.94 (2H, m), 7.03 (1H, t), 7.12 (1H, d), 7.26-7.32 (1H, m), 7.62 (1H, d), 7.72 (1H, d), 7.83 (1H, t), 8.11 (1H, t), 8.17 (1H, s), 8.37 (1H, t), 9.69 (1H, br s). |
| 62 | 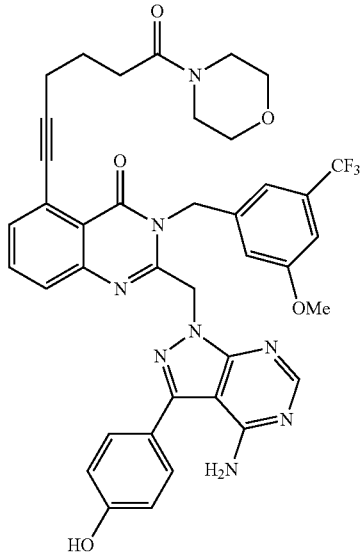 [SMILES: COc1cc(Cn2c(Cn3nc(-c4ccc(O)cc4)c4c(N)ncnc43)nc3cccc(C#CCCCC(=O)N4CCOCC4)c3c2=O)cc(C(F)(F)F)c1] | 2-((4-Amino-3-(4-hydroxyphenyl)-1H-pyrazolo[3,4-d]pyrimidin-1-yl)methyl)-3-(3-methoxy-5-(trifluoromethyl)benzyl)-5-(6-morpholino-6-oxohex-1-yn-1-yl)quinazolin-4(3H)-one.<br>R$^t$ 3.74 min; m/z 753/755 (M + H)$^+$ (ES$^+$);<br>$^1$H NMR (500 MHz, DMSO-d$_6$) δ: 1.73 (2H, quin), 2.47-2.49 (2H, m), 2.53-2.56 (2H, m), 3.22-3.28 (2H, m), 3.28-3.31 (2H, m), 3.33-3.34 (2H, m), 3.41-3.46 (2H, m), 3.58 (3H, s), 5.39 (2H, br s), 5.71 (2H, br s), 6.36 (1H, s), 6.68 (1H, s), 6.86 (2H, d), 6.91 (1H, s), 7.27 (2H, d), 7.59 (2H, d), 7.72-7.82 (1H, m), 8.21 (1H, br s), 9.77 (1H, s). |
| 63 | 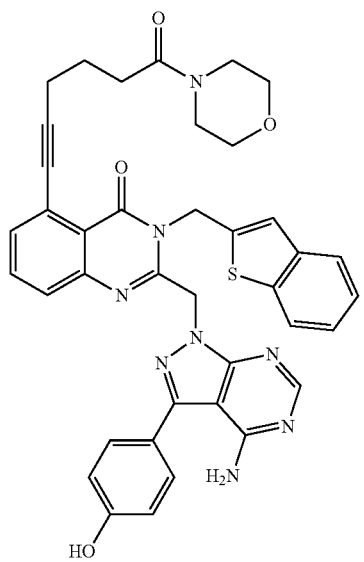 [SMILES: Nc1ncnc2c1c(-c1ccc(O)cc1)nn2Cc1nc2cccc(C#CCCCC(=O)N3CCOCC3)c2c(=O)n1Cc1cc2ccccc2s1] | 2-((4-Amino-3-(4-hydroxyphenyl)-1H-pyrazolo[3,4-d]pyrimidin-1-yl)methyl)-3-(benzo[b]thiophen-2-ylmethyl)-5-(6-morpholino-6-oxohex-1-yn-1-yl)quinazolin-4(3H)-one.<br>R$^t$ 3.68 min; m/z 711 (M + H)$^+$ (ES$^+$);<br>$^1$H NMR (500 MHz, DMSO-d$_6$) δ: 1.78 (2H, quin), 2.54-2.56 (2H, m), 2.60-2.63 (2H, m), 3.43-3.59 (8H, m), 5.62 (2H, s), 5.83 (2H, s), 6.82 (2H, d), 7.05 (1H, s), 7.20 (2H, d), 7.27-7.32 (2H, m), 7.41 (1H, d), 7.57 (1H, d), 7.61-7.66 (1H, m), 7.67-7.73 (1H, m), 7.80-7.86 (1H, m), 8.24 (1H, br s), 9.76 (1H, s). |

TABLE 2-continued

| Example No. | Structure | Name and Analytical Data |
|---|---|---|
| 64 | 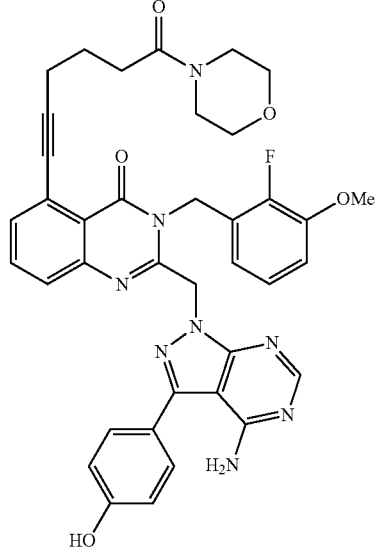 [SMILES: COc1cccc(Cn2c(Cn3nc(-c4ccc(O)cc4)c4c(N)ncnc43)nc3cccc(C#CCCCC(=O)N4CCOCC4)c3c2=O)c1F] | 2-((4-Amino-3-(4-hydroxyphenyl)-1H-pyrazolo[3,4-d]pyrimidin-1-yl)methyl)-3-(2-fluoro-3-methoxybenzyl)-5-(6-morpholino-6-oxohex-1-yn-1-yl)quinazolin-4(3H)-one.<br>$R^t$ 3.47 min; m/z 703 (M + H)$^+$ (ES$^+$);<br>$^1$H NMR (500 MHz, DMSO-d$_6$) δ: 1.71 (2H, quin), 2.44-2.49 (2H, m), 2.54 (2H, t), 3.20-3.35 (6H, m), 3.42-3.46 (2H, m), 3.73 (3H, s), 5.33 (2H, br s), 5.69-5.76 (2H, m), 5.80 (1H, t), 6.61 (1H, t), 6.82 (1H, t), 6.87 (2H, d), 7.33 (2H, d), 7.61 (1H, d), 7.58 (1H, d), 7.71-7.81 (1H, m), 8.26 (1H, br s), 9.78 (1H, s). |
| 65 | 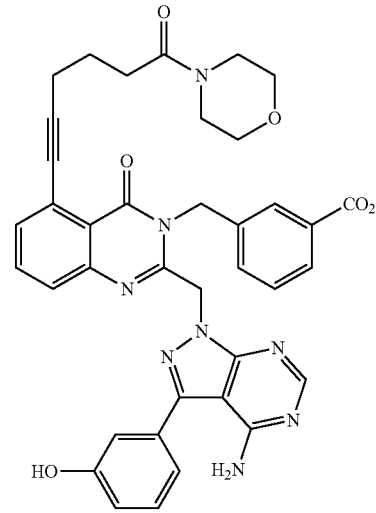 | Methyl 3-((2-((4-amino-3-(3-hyroxyphenyl)-1H-pyrazolo[3,4-d]pyrimidin-1-yl)methyl)-5-(6-morpholino-6-oxohex-1-yn-1-yl)-4-oxoquinazolin-3(4H)-yl)methyl)benzoate.<br>$R^t$ 4.44 min; m/z 713 (M + H)$^+$ (ES$^+$);<br>$^1$H NMR (500 MHz, DMSO-d$_6$) δ: 1.73 (2H, quin), 2.44-2.59 (4H, m), 3.25 (4H, s), 3.30-3.34 (2H, m), 3.40-3.43 (2H, m), 3.69 (3H, s), 5.39 (2H, br s), 5.73 (2H, br s), 6.79-6.86 (3H, m), 6.90 (1H, d), 7.11 (1H, t), 7.19 (1H, s), 7.26 (1H, t), 7.57-7.66 (3H, m), 7.75-7.82 (1H, m), 8.22 (1H, br s), 9.67 (1H, s). |
| 66 | 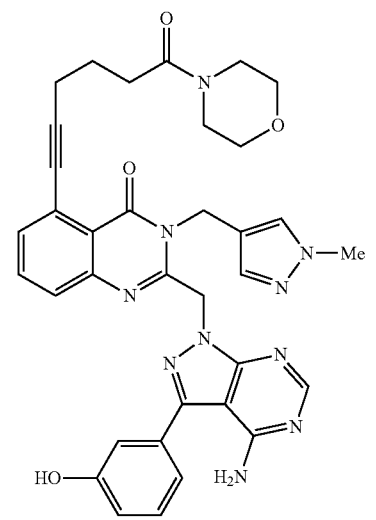 [SMILES: Cn1cc(Cn2c(Cn3nc(-c4cccc(O)c4)c4c(N)ncnc43)nc3cccc(C#CCCCC(=O)N4CCOCC4)c3c2=O)cn1] | 2-((4-Amino-3-(3-hydroxyphenyl)-1H-pyrazolo[3,4-d]pyrimidin-1-yl)methyl)-3-((1-methyl-1H-pyrazolo-4-yl)methyl-5-(6-morpholino-6-oxohex-1-yn-1-yl)quinazolin-4(3H)-one.<br>$R^t$ 4.47 min; m/z 659 (M + H)$^+$ (ES$^+$);<br>$^1$H NMR (500 MHz, DMSO-d$_6$) δ: 1.80 (2H, quin), 2.54-2.57 (2H, m), 2.65-2.68 (2H, m), 3.38-3.43 (4H, m), 3.47-3.55 (4H, m), 3.71 (3H, s), 5.18 (2H, s), 5.81 (2H, s), 6.86 (1H, dd), 7.00-7.07 (2H, m), 7.24 (1H, s), 7.29-7.36 (2H, m), 7.49-7.54 (2H, m), 7.61-7.67 (1H, m), 8.26 (1H, s), 9.70 (1H, s). |

| Example No. | Structure | Name and Analytical Data |
|---|---|---|
| 67 | 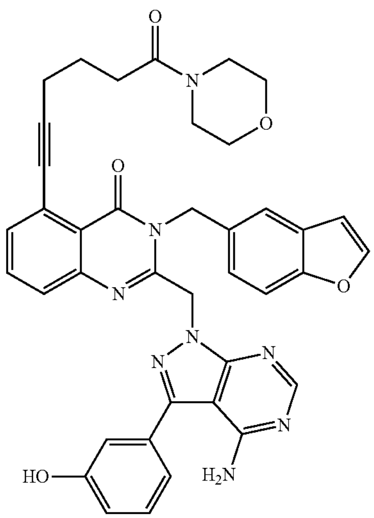 [SMILES: Nc1ncnc2c1c(-c1cccc(O)c1)nn2Cc1nc2cccc(C#CCCCC(=O)N3CCOCC3)c2c(=O)n1Cc1ccc2occc2c1] | 2-((4-Amino-3-(3-hydroxyphenyl)-1H-pyrazolo[3,4-d]pyrimidin-1-yl)methyl)-3-(benzofuran-5-ylmethyl)-5-(6-morpholino-6-oxohex-1-yn-1-yl)quinazolin-4(3H)-one.<br>R$^t$ 4.46 min; m/z 695 (M + H)$^+$ (ES$^+$);<br>$^1$H NMR (500 MHz, DMSO-d$_6$) δ: 1.75 (2H, quin), 2.51-2.55 (2H, m), 2.58 (2H, t), 3.29 (4H, dd), 3.40-3.58 (4H, m), 5.49 (2H, br s), 5.73 (2H, s), 6.74-6.78 (1H, m), 6.80-6.87 (2H, m), 6.87-6.95 (2H, m), 7.11 (1H, s), 7.27 (1H, t), 7.37 (1H, d), 7.44 (1H, d), 7.57 (1H, d), 7.68-7.74 (1H, m), 7.89 (1H, d), 8.21 (1H, s), 9.68 (1H, br s). |
| 68 | 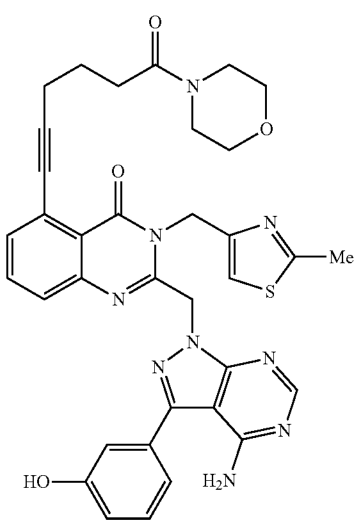 [SMILES: Cc1nc(Cn2c(Cn3nc(-c4cccc(O)c4)c4c(N)ncnc43)nc3cccc(C#CCCCC(=O)N4CCOCC4)c3c2=O)cs1] | 2-((4-Amino-3-(3-hydroxyphenyl)-1H-pyrazolo[3,4-d]pyrimidin-1-yl)methyl)-3-((2-methylthiazol-4-yl)methyl)-5-(6-morpholino-6-oxohex-1-yn-1-yl)quinazolin-4(3H)-one.<br>R$^t$ 4.42 min; m/z 676 (M + H)$^+$ (ES$^+$);<br>$^1$H NMR (500 MHz, DMSO-d$_6$) δ: 1.75 (2H, quin), 2.46 (3H, s), 2.57-2.62 (4H, m), 3.37-3.60 (8H, m), 5.36 (2H, s), 5.87 (2H, s), 6.80 (1H, s), 6.82-6.87 (1H, m), 6.98-7.04 (2H, m), 7.28-7.34 (1H, m), 7.48 (1H, d), 7.53-7.57 (1H, m), 7.68-7.73 (1H, m), 8.26 (1H, br s), 9.69 (1H, s). |
| 69 | 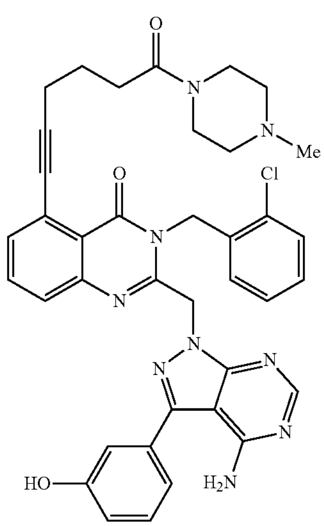 [SMILES: CN1CCN(C(=O)CCCC#Cc2cccc3nc(Cn4nc(-c5cccc(O)c5)c5c(N)ncnc54)n(Cc4ccccc4Cl)c(=O)c23)CC1] | 2-((4-Amino-3-(3-hydroxyphenyl)-1H-pyrazolo[3,4-d]pyrimidin-1-yl)methyl)-3-(2-chlorobenzyl)-5-(6-(4-methylpiperazin-1-yl)-6-oxohex-1-yn-1-yl)quinazolin-4(3H)-one.<br>R$^t$ 4.38 min; m/z 702/704 (M + H)$^+$ (ES$^+$);<br>$^1$H NMR (500 MHz, DMSO-d$_6$) δ: 1.71 (2H, quin), 1.91-2.34 (7H, m), 2.44-2.48 (2H, m), 2.48-2.49 (2H, m), 3.22-3.30 (2H, m), 3.32-3.34 (2H, m), 5.30 (2H, s), 5.75 (2H, s), 6.17 (1H, d), 6.80 (1H, t), 6.84 (1H, dd), 6.90-6.95 (2H, m), 7.05 (1H, t), 7.12 (1H, d), 7.30 (1H, t), 6.71 (1H, d), 7.68 (1H, d), 7.80 (1H, t), 8.18 (1H, s), 9.68 (1H, s). |

TABLE 2-continued

| Example No. | Structure | Name and Analytical Data |
|---|---|---|
| 70 | 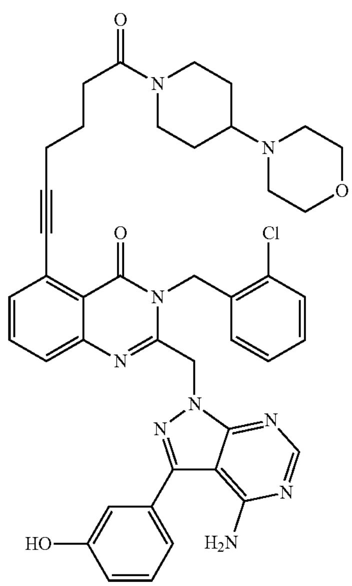 [SMILES: Nc1ncnc2c1c(-c1cccc(O)c1)nn2Cc1nc2cccc(C#CCCCC(=O)N3CCC(N4CCOCC4)CC3)c2c(=O)n1Cc1ccccc1Cl] | 2-((4-Amino-3-(3-hydroxyphenyl)-1H-pyrazolo[3,4-d]pyrimidin-1-yl)methyl)-3-(2-chlorobenzyl)-5-(6-(4-morpholinopiperidin-1-yl)-6-oxohex-1-yn-1-yl)quinazolin-4(3H)-one.<br>R$^t$ 4.43 min; m/z 772/774 (M + H)$^+$ (ES$^+$);<br>$^1$H NMR (500 MHz, DMSO-d$_6$) δ: 1.13 (2H, br s), 1.52 (1H, br s), 1.63-1.76 (3H, m), 2.04-2.80 (11H, m), 3.56 (4H, br s), 3.79 (1H, d), 4.33 (1H, d), 5.29 (2H, s), 5.76 (2H, br s), 6.16 (1H, d), 6.79 (1H, t), 6.82-6.87 (1H, m), 6.89-6.94 (2H, m), 7.05 (1H, t), 7.13 (1H, d), 7.30 (1H, t), 7.60 (1H, d), 7.69 (1H, d), 7.80 (1H, t), 8.21 (1H, br s), 9.69 (1H, s). |
| 71 | 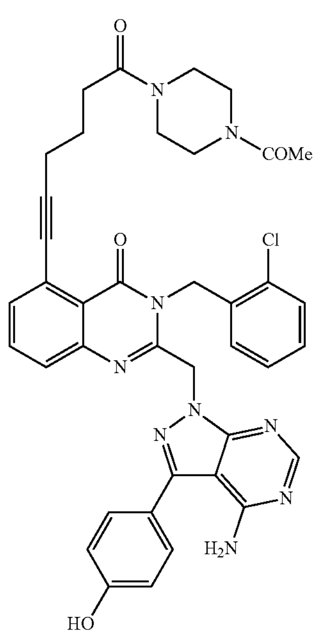 | 5-(6-(4-Acetylpiperazin-1-yl)-6-oxohex-1-yn-1-yl)-2-((4-amino-3-(4-hydroxyphenyl)-1H-pyrazolo[3,4-d]pyrimidin-1-yl)methyl-3-(2-chlorobenzyl)quinazolin-4(3H)-one.<br>R$^t$ 4.32 min; m/z 730/732 (M + H)$^+$ (ES$^+$);<br>$^1$H NMR (500 MHz, DMSO-d$_6$) δ: 1.72 (2H, t), 1.99 (3H, d), 2.53-2.54 (2H, m), 2.55-2.59 (2H, m), 3.16-3.33 (8H, m), 5.28 (2H, d), 5.73 (2H, br s), 6.09-6.21 (1H, m), 6.77 (1H, dt), 6.87 (2H, d), 6.96-7.05 (1H, m), 7.06-7.12 (1H, m), 7.32 (2H, d), 7.61 (1H, d), 7.69 (1H, d), 7.77-7.85 (1H, m), 8.18 (1H, br s), 9.78 (1H, s). |

| Example No. | Structure | Name and Analytical Data |
| --- | --- | --- |
| 72 | 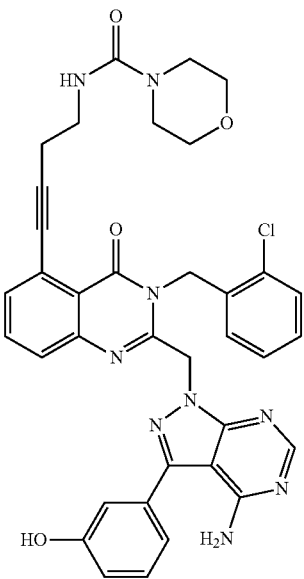 [SMILES: Nc1ncnc2c1c(-c1cccc(O)c1)nn2Cc1nc2cccc(C#CCCNC(=O)N3CCOCC3)c2c(=O)n1Cc1ccccc1Cl] | N-(4-(2-((4-Amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)but-3-yn-1-yl)morpholine-4-carboxamide.<br>$R^t$ 4.92 min; m/z 690/692 (M + H)$^+$ (ES$^+$);<br>$^1$H NMR (500 MHz, DMSO-d$_6$) δ: 2.52-2.56 (2H, m), 3.09-3.19 (4H, m), 3.21-3.28 (2H, m), 3.40-3.45 (4H, m), 5.30 (2H, s), 5.76 (2H, br s), 6.16 (1H, d), 6.60 (1H, t), 6.79 (1H, t), 6.84 (1H, dd), 6.90-6.95 (2H, m), 7.05 (1H, t), 7.13 (1H, d), 7.30 (1H, t), 7.63 (1H, d), 7.69 (1H, d), 7.82 (1H, t), 8.18 (1H, s), 9.69 (1H, s). |
| 73 | 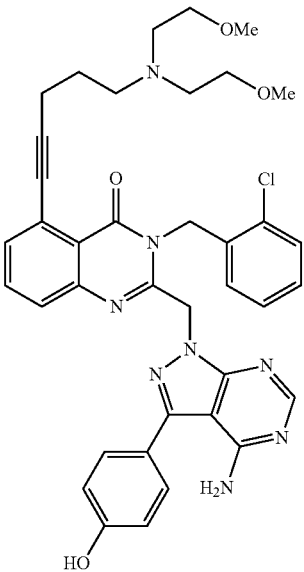 [SMILES: COCCN(CCCC#Cc1cccc2nc(Cn3nc(-c4ccc(O)cc4)c4c(N)ncnc43)n(Cc3ccccc3Cl)c(=O)c12)CCOC] | 2-((4-Amino-3-(4-hydroxyphenyl)-1H-pyrazolo[3,4-d]pyrimidin-1-yl)methyl)-5-(5-(bis(2-methoxyethyl)amino)pent-1-ynyl)-3-(2-chlorobenzyl)quinazolin-4(3H)-one.<br>$R^t$ 1.42 min; m/z 707/709 (M + H)$^+$ (ES$^+$) (Method D);<br>$^1$H NMR (400 MHz, DMSO-d$_6$) δ: 1.59 (2H, quin), 2.42 (2H, t), 2.53-2.59 (6H, overlapping m), 3.15 (6H, s), 3.30 (4H, m), 5.29 (2H, s), 5.73 (2H, s), 6.17 (1H, d), 6.78 (1H, m), 6.88 (2H, d), 7.03 (1H, m), 7.12 (1H, dd), 7.33 (2H, d), 7.56 (1H, dd), 7.66 (1H, dd), 7.79 (1H, m), 8.16 (1H, s), 9.78 (1H, s). |

TABLE 2-continued

| Example No. | Structure | Name and Analytical Data |
|---|---|---|
| 74 | 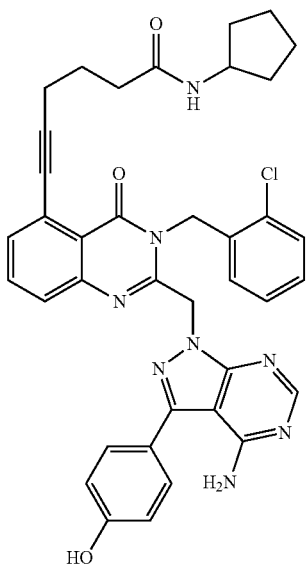 [SMILES: Nc1ncnc2c1c(-c1ccc(O)cc1)nn2Cc1nc2cccc(C#CCCCC(=O)NC3CCCC3)c2c(=O)n1Cc1ccccc1Cl] | 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-cyclopentylhex-5-ynamide.<br>$R^t$ 1.99 min; m/z 687/689 (M + H)$^+$ (ES$^+$) (Method D);<br>$^1$H NMR (400 MHz, DMSO-d$_6$) δ: 1.25 (2H, m), 1.44 (2H, m), 1.53 (2H, m), 1.69-1.76 (4H, overlapping m), 2.17 (2H, t), 2.39 (2H, t), 3.93 (1H, m), 5.29 (2H, s), 5.74 (2H, s), 6.15 (1H, d), 6.78 (1H, t), 6.88 (2H, d), 7.03 (1H, t), 7.12 (1H, dd), 7.32 (2H, d), 7.62 (1H, dd), 7.67-7.70 (2H, overlapping m), 7.81 (1H, t), 8.16 (1H, s), 9.78 (1H, br s). |
| 75 | 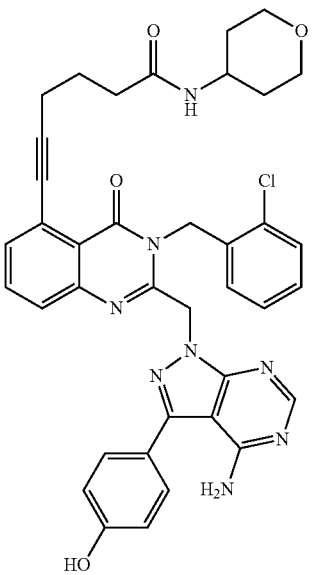 | 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-(tetrahydro-2H-pyran-4-yl)hex-5-ynamide.<br>$R^t$ 1.76 min; m/z 703/705 (M + H)$^+$ (ES$^+$) (Method D);<br>$^1$H NMR (400 MHz, DMSO) δ: 1.22-1.32 (2H, overlapping m), 1.58-1.62 (2H, overlapping m), 1.73 (2H, quin), 2.19 (2H, t), 2.40 (2H, t), 3.24-3.28 (2H, overlapping m), 3.66-3.77 (3H, overlapping m), 5.29 (2H, s), 5.73 (2H, s), 6.17 (1H, d), 6.78 (1H, t), 6.87 (2H, d), 7.02 (1H, t), 7.11 (1H, dd), 7.33 (2H, d), 7.69 (1H, dd), 7.67-7.70 (2H, overlapping m), 7.80 (1H, t), 8.15 (1H, s), 9.74 (1H, s). |

TABLE 2-continued

| Example No. | Structure | Name and Analytical Data |
|---|---|---|
| 76 | 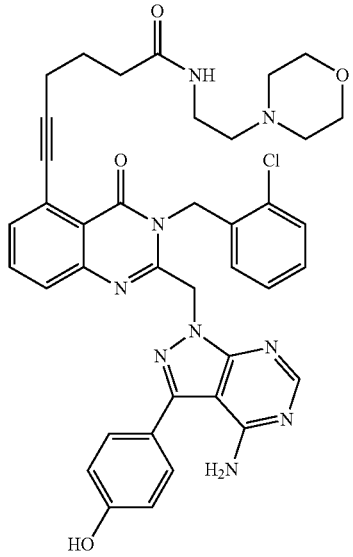 [SMILES: Nc1ncnc2c1c(-c1ccc(O)cc1)nn2Cc1nc2cccc(C#CCCCC(=O)NCCN3CCOCC3)c2c(=O)n1Cc1ccccc1Cl] | 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-(2-morpholinoethyl)hex-5-ynamide.<br>R$^t$ 1.45 min; m/z 732/734 (M + H)$^+$ (ES$^+$) (Method D); $^1$H NMR (400 MHz, DMSO) δ: 1.72 (2H, m), 2.18-2.24 (4H, overlapping m), 2.29 (4H, m), 2.42 (2H, t), 3.08 (2H, q), 3.49 (4H, t), 5.28 (2H, s), 5.73 (2H, s), 6.15 (1H, d), 6.76 (1H, t), 6.87 (2H, d), 7.02 (1H, t), 7.11 (1H, d), 7.32 (2H, d), 7.61 (1H, dd), 7.65-7.69 (2H, overlapping m), 7.80 (1H, t), 8.15 (1H, s), 9.77 (1H, s). |
| 77 | 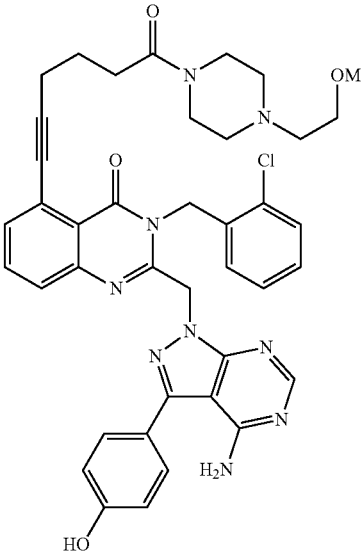 | 2-((4-Amino-3-(4-hydroxyphenyl)-1H-pyrazolo[3,4-d]pyrimidin-1-yl)methyl)-3-(2-chlorobenzyl)-5-(6-(4-(2-methoxyethyl)piperazin-1-yl)-6-oxohex-1-ynyl)quinazolin-4(3H)-one.<br>R$^t$ 1.33 min; m/z 746/748 (M + H)$^+$ (ES$^+$) (Method D); $^1$H NMR (400 MHz, DMSO) δ: 1.78 (2H, quin), 2.31 (4H, m), 2.45-2.50 (6H, m), 3.26 (3H, s), 3.36 (4H, m), 3.43 (2H, t), 5.41 (2H, s), 5.67 (2H, s), 6.27 (2H, br s), 6.48 (1H, d), 6.90-6.97 (3H, overlapping m), 7.12 (1H, m), 7.24 (1H, dd), 7.37 (2H, d), 7.54-7.57 (2H, overlapping m), 7.73 (1H, t), 8.17 (1H, s), 9.37 (1H, s). |

TABLE 2-continued

| Example No. | Structure | Name and Analytical Data |
|---|---|---|
| 78 | 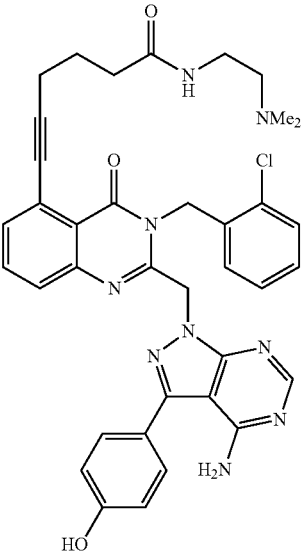 [SMILES: CN(C)CCNC(=O)CCCC#Cc1cccc2nc(Cn3nc(-c4ccc(O)cc4)c4c(N)ncnc43)n(Cc3ccccc3Cl)c(=O)c12] | 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-(2-(dimethylamino)ethyl)hex-5-ynamide.<br>R$^t$ 1.37 min; m/z 690/692 (M + H)$^+$ (ES$^+$) (Method D);<br>$^1$H NMR (400 MHz, DMSO) δ: 1.70 (2H, quin), 2.07 (6H, s), 2.16-2.21 (4H, overlapping m), 2.39 (2H, t), 3.05 (2H, q), 5.28 (2H, s), 5.73 (2H, s), 6.15 (1H, d), 6.77 (1H, t), 6.87 (2H, d), 7.01 (1H, t), 7.11 (1H, m), 7.31 (2H, d), 7.60-7.69 (3H, overlapping m), 7.79 (1H, t), 8.15 (1H, s), 9.79 (1H, s). |
| 79 | 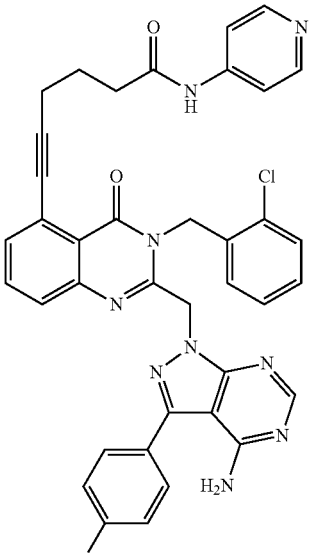 | 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-(pyridin-4-yl)hex-5-ynamide.<br>R$^t$ 1.40 min; m/z 696/698 (M + H)$^+$ (ES$^+$) (Method D);<br>$^1$H NMR (400 MHz, DMSO) δ: 1.83 (2H, m), 2.50-2.53 (4H, overlapping m), 5.29 (2H, s), 5.73 (2H, s), 6.17 (1H, d), 6.77 (1H, t), 6.87 (2H, d), 7.00 (1H, t), 7.10 (1H, d), 7.32 (2H, d), 7.51 (2H, br s), 7.60 (1H, dd), 7.67 (1H, dd), 7.77 (1H, t), 8.15 (1H, s), 8.37 (2H, br s), 9.75 (1H, s), 10.22 (1H, s). |

TABLE 2-continued

| Example No. | Structure | Name and Analytical Data |
| --- | --- | --- |
| 80 | 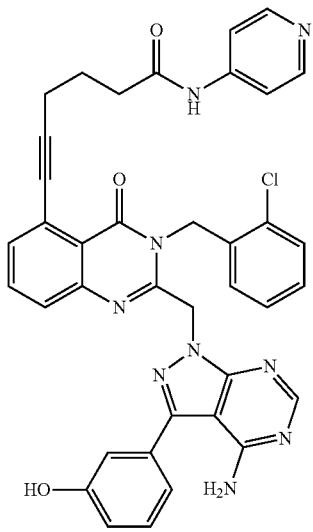 [SMILES: Nc1ncnc2c1c(-c1cccc(O)c1)nn2Cc1nc2cccc(C#CCCCC(=O)Nc3ccncc3)c2c(=O)n1Cc1ccccc1Cl] | 6-(2-((4-Amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N-(pyridin-4-yl)hex-5-ynamide. $R^t$ 1.42 min; m/z 696/698 (M + H)$^+$ (ES$^+$) (Method D); $^1$H NMR (400 MHz, DMSO-d$_6$) δ: 1.84 (2H, quintet), 5.31 (2H, s), 5.76 (2H, s), 6.17 (1H, d), 6.79 (2H, dt), 6.85 (1H, ddd), 6.92-6.94 (2H, overlapping m), 7.03 (1H, td), 7.12 (1H, dd), 7.31 (1H, t), 7.51 (2H, dd), 7.62 (1H, dd), 7.67 (1H, dd), 7.78 (1H dd), 8.18 (1H, br s), 8.37 (2 H dd), 9.66 (1H, br s), 10.22 (1H, br s). |
| 81 | 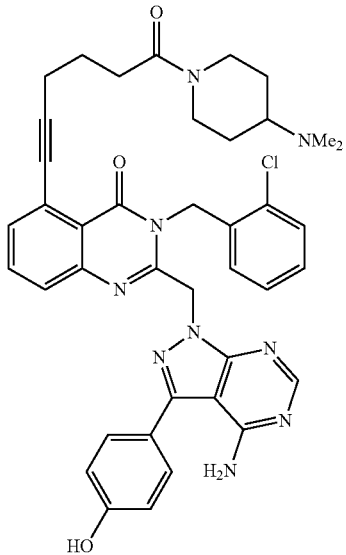 [SMILES: CN(C)C1CCN(C(=O)CCCC#Cc2cccc3nc(Cn4nc(-c5ccc(O)cc5)c5c(N)ncnc54)n(Cc4ccccc4Cl)c(=O)c23)CC1] | 2-((4-Amino-3-(4-hydroxyphenyl)-1H-pyrazolo[3,4-d]pyrimidin-1-yl)methyl)-3-(2-chlorobenzyl)-5-(6-(4-(dimethylamino)piperidin-1-yl)-6-oxohex-1-ynyl)quinazolin-4(3H)-one. $R^t$ 1.34 min; m/z 730/732 (M + H)$^+$ (ES$^+$) (Method D); $^1$H NMR (400 MHz, DMSO) δ: 1.01-1.09 (2H, overlapping m), 1.14-1.24 (4H, overlapping m), 1.61-1.66 (2H, overlapping m), 1.78 (2H, quin), 2.15 (6H, s), 2.17-2.25 (2H, overlapping m), 2.48-2.55 (4H, overlapping m), 5.41 (2H, s), 5.67 (2H, s), 6.27 (2H, br s), 6.48 (1H, d), 6.90-6.97 (3H, overlapping m), 7.12 (1H, m), 7.24 (1H, d), 7.37 (2H, d), 7.54-7.57 (2H, overlapping m), 7.73 (1H, t), 8.17 (1H, s), 9.37 (1H, br s). |

TABLE 2-continued

| Example No. | Structure | Name and Analytical Data |
|---|---|---|
| 82 | 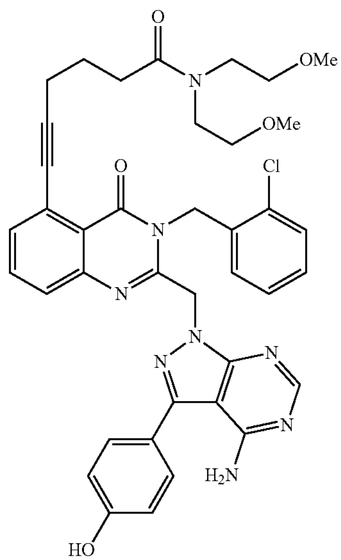 [SMILES: COCCN(CCOC)C(=O)CCCC#Cc1cccc2nc(Cn3nc(-c4ccc(O)cc4)c4c(N)ncnc43)n(Cc3ccccc3Cl)c(=O)c12] | 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide.<br>R$^t$ 1.89 min; m/z 735/737 (M + H)$^+$ (ES$^+$) (Method D); $^1$H NMR (400 MHz, DMSO) δ: 1.70 (2H, quin), 2.45 (2H, t), 2.55 (2H, t), 3.11 (3H, s), 3.18 (3H, s), 3.24-3.35 (8H, overlapping m), 5.28 (2H, s), 5.73 (2H, s), 6.20 (1H, d), 6.79 (1H, t), 6.88 (2H, d), 7.03 (1H, t), 7.13 (1H, d), 7.33 (2H, d), 7.60 (1H, d), 7.67 (1H, d), 7.80 (1H, t), 8.19 (1H, s), 9.75 (1H, s). |
| 83 | 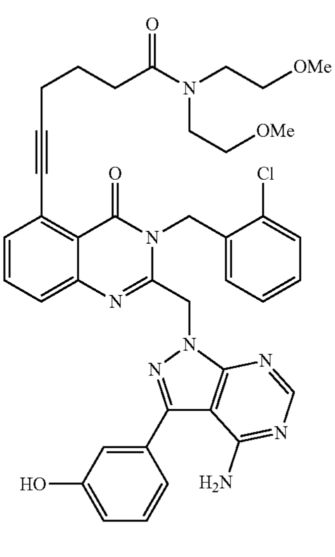 [SMILES: COCCN(CCOC)C(=O)CCCC#Cc1cccc2nc(Cn3nc(-c4cccc(O)c4)c4c(N)ncnc43)n(Cc3ccccc3Cl)c(=O)c12] | 6-(2-((4-Amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-bis(2-methoxyethyl)hex-5-ynamide.<br>R$^t$ 1.92 min; m/z 735/737 (M + H)$^+$ (ES$^+$) (Method D); $^1$H NMR (400 MHz, DMSO-d$_6$) δ: 1.70 (2H, quin), 2.46 (2H, t), 2.55 (2H, t), 3.12 (3H, s), 3.19 (3H, s), 3.26 (2H, overlapping m), 3.31 (4H, m, partially obscured by HOD peak), 3.35 (2H, q), 5.30 (2H, s), 5.76 (2H, s), 6.18 (1H, dd), 6.80 (1H, dt), 6.85 (1H, ddd), 6.92-6.94 (2H, overlapping m), 7.05 (1H, td), 7.13 (1H, dd), 7.31 (1H, t), 7.61 (1H, dd), 7.68 (1H, dd), 7.81 (1H, dd), 8.18 (1H, br s), 9.65 (1H, br s). |

TABLE 2-continued

| Example No. | Structure | Name and Analytical Data |
|---|---|---|
| 84 | 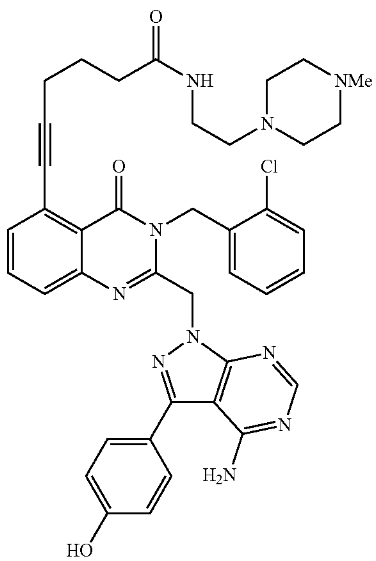 [SMILES: CN1CCN(CCNC(=O)CCCC#Cc2cccc3nc(Cn4nc(-c5ccc(O)cc5)c5c(N)ncnc54)n(Cc4ccccc4Cl)c(=O)c23)CC1] | 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-(2-(4-methylpiperazin-1-yl)ethyl)hex-5-ynamide.<br>R$^t$ 1.34 min; m/z 745/747 (M + H)$^+$ (ES$^+$) (Method D);<br>$^1$H NMR (400 MHz, 100° C., DMSO-d$_6$) δ: 1.79 (2H, quin), 2.12 (3H, s), 2.22-2.35 (10H, overlapping m), 2.44-2.50 (4H, overlapping m), 3.12 (2H, q), 5.42 (2H, s), 5.68 (2H, s), 6.28 (2H, s), 6.49 (1H, d), 6.90-6.97 (3H, overlapping m), 7.13 (1H, m), 7.18 (1H, br s), 7.24 (1H, d), 7.37 (2H, d), 7.55-7.58 (2H, overlapping m), 7.74 (1H, t), 8.17 (1H, s), 9.37 (1H, br s). |
| 85 | 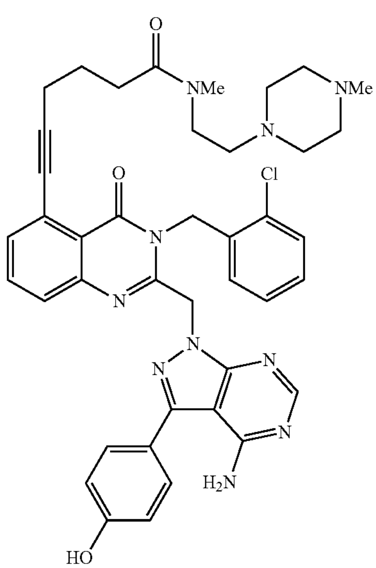 [SMILES: CN1CCN(CCN(C)C(=O)CCCC#Cc2cccc3nc(Cn4nc(-c5ccc(O)cc5)c5c(N)ncnc54)n(Cc4ccccc4Cl)c(=O)c23)CC1] | 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-methyl-N-(2-(4-methyl piperazin-1-yl)ethyl)hex-5-ynamide.<br>R$^t$ 1.40 min; m/z 759/761 (M + H)$^+$ (ES$^+$) (Method D);<br>$^1$H VT NMR (400 MHz, 100° C., DMSO-d$_6$) δ: 1.79 (2H, quin), 2.12 (3H, s), 2.25 (4H, bs), 2.33-2.36 (6H, overlapping m), 2.79 (3H, s), 3.29 (2H, t), 5.41 (2H, s), 5.68 (2H, s), 6.27 (2H, s), 6.46 (1H, d), 6.89-6.96 (3H, overlapping m), 7.02 (1H, m), 7.11 (1H, t), 7.24 (1H, dd), 7.37 (2H, d), 7.56 (2H, d), 7.73 (1H, t), 8.17 (1H, s). |

TABLE 2-continued

| Example No. | Structure | Name and Analytical Data |
|---|---|---|
| 86 | 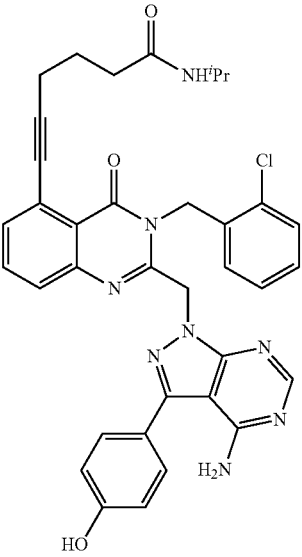 | 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-isopropylhex-5-ynamide. R$^t$ 1.87 min; m/z 661/663 (M + H)$^+$ (ES$^+$) (Method D); $^1$H NMR (400 MHz, DMSO) δ: 0.94-0.95 (6H, d), 1.72 (2H, m), 2.16 (2H, t), 2.39 (2H, t), 3.78 (1H, m), 5.29 (2H, s), 5.73 (2H, s), 6.17 (1H, d), 6.78 (1H, t), 6.87 (2H, d), 7.02 (1H, t), 7.11 (1H, d), 7.32 (2H, d), 7.55 (1H, d), 7.61 (1H, dd), 7.67 (1H, dd), 7.80 (1H, t), 8.15 (1H, s). |
| 87 | 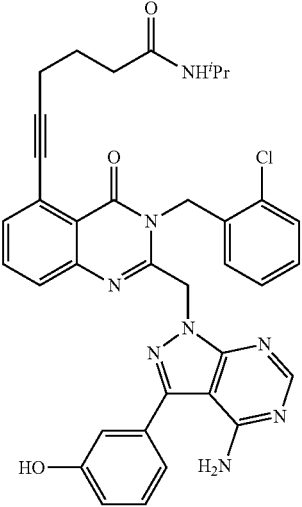 | 6-(2-((4-Amino-3-(3-hydroxyphenyl)-1H-pyrazolo[3,4-d]pyrimidin-1-yl)methyl)-3-(2-chlorobenzyl)-4-oxo-3,4-dihydroquinazolin-5-yl)-N-isopropylhex-5-ynamide. R$^t$ 1.91 min; m/z 661/663 (M + H)$^+$ (ES$^+$) (Method D); $^1$H NMR (400 MHz, DMSO-d$_6$) δ: 0.96 (6H, d), 1.72 (2H, quin), 2.17 (2H, t), 2.40 (2H, t), 3.79 (1H, septuplet), 5.31 (2H, s), 5.76 (2H, s), 6.17 (1H, d), 6.80 (1H, dt), 6.83 (1H, ddd), 6.92-6.94 (2H, m), 7.04 (1H, td), 7.14 (1H, dd), 7.31 (1H, t), 7.55 (1H, d), 7.63 (1H, dd), 7.69 (1H, dd), 7.81 (1H, dd), 8.18 (1H, br s), 9.66 (1H, br s). |

TABLE 2-continued

| Example No. | Structure | Name and Analytical Data |
| --- | --- | --- |
| 88 | 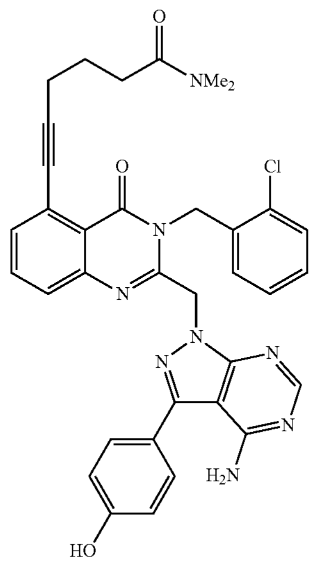 [SMILES: CN(C)C(=O)CCCC#Cc1cccc2nc(Cn3nc(-c4ccc(O)cc4)c4c(N)ncnc43)n(Cc3ccccc3Cl)c(=O)c12] | 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N,N-dimethylhex-5-ynamide. R$^t$ 1.80 min; m/z 647/649 (M + H)$^+$ (ES$^+$) (Method D); $^1$H NMR (400 MHz, DMSO) δ: 1.75 (2H, quin), 2.47-2.50 (4H, overlapping m), 2.75 (6H, br s), 5.36 (2H, s), 5.71 (2H, s), 6.33-6.37 (3H, overlapping m), 6.86-6.92 (3H, overlapping m), 7.08 (1H, t), 7.20 (1H, d), 7.36 (2H, d), 7.57-7.62 (2H, overlapping m), 7.77 (1H, t), 8.17 (1H, s), 9.53 (1H, s). |
| 89 | 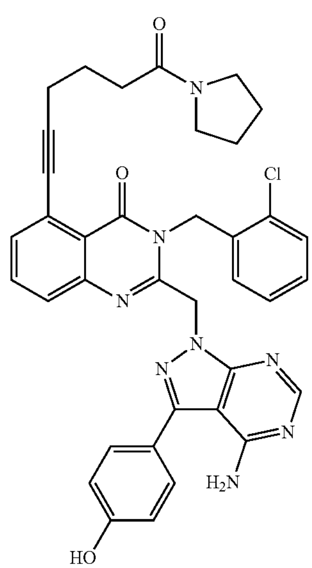 [SMILES: Nc1ncnc2c1c(-c1ccc(O)cc1)nn2Cc1nc2cccc(C#CCCCC(=O)N3CCCC3)c2c(=O)n1Cc1ccccc1Cl] | 2-((4-Amino-3-(4-hydroxyphenyl)-1H-pyrazolo[3,4-d]pyrimidin-1-yl)methyl)-3-(2-chlorobenzyl)-5-(6-oxo-6-(pyrrolidin-1-yl)hex-1-yn-1-yl)quinazolin-4(3H)-one. R$^t$ 1.86 min; m/z 673/675 (M + H)$^+$ (ES$^+$) (Method D); $^1$H NMR (400 MHz, DMSO) δ: 1.70-1.79 (6H, overlapping m), 2.43-2.50 (4H, m, partially obscured by DMSO peak), 3.23-3.4 (4H, m, partially obscured by HOD peak), 5.37 (2H, s), 5.71 (2H, s), 6.38 (1H, m), 6.55 (2H, br s), 6.90-6.92 (3H, overlapping m), 7.09 (1H, t), 7.21 (1H, d), 7.36 (2H, d), 7.59 (2H, t), 7.76 (1H, t), 8.20 (1H, s). |

TABLE 2-continued

| Example No. | Structure | Name and Analytical Data |
|---|---|---|
| 90 | 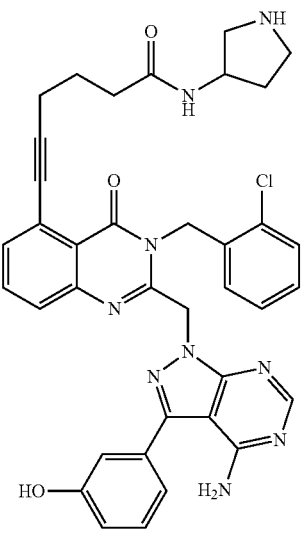 [SMILES: Nc1ncnc2c1c(-c1cccc(O)c1)nn2Cc1nc2cccc(C#CCCCC(=O)NC3CCNC3)c2c(=O)n1Cc1ccccc1Cl] | 6-(2-((4-Amino-3-(4-hydroxyphenyl)-1H-pyrazolo[3,4-d]pyrimidin-1-yl)methyl)-3-(2-chlorobenzyl)-4-oxo-3,4-dihydroquinazolin-5-yl)-N-(pyrrolidin-3-yl)hex-5-ynamide.<br>R$^t$ 1.28 min; m/z 688/690 (M + H)$^+$ (ES$^+$) (Method D);<br>$^1$H NMR (400 MHz, DMSO) δ: 1.41 (1H, m), 1.72 (2H, quin), 1.83 (1H, m), 1.94 (1H, m), 2.16-2.20 (2H, overlapping m), 2.38-2.50 (4H, overlapping m), 2.69-2.88 (2H, overlapping m), 4.02 (1H, m), 5.29 (2H, s), 5.73 (2H, s), 6.17 (1H, d), 6.78 (1H, m), 6.87 (2H, d), 7.02 (1H, m), 7.12 (1H, m), 7.32 (2H, d), 7.61 (1H, d), 7.67 (1H, dd), 7.76-7.81 (2H, overlapping m), 8.15 (1H, s). |
| 91 | 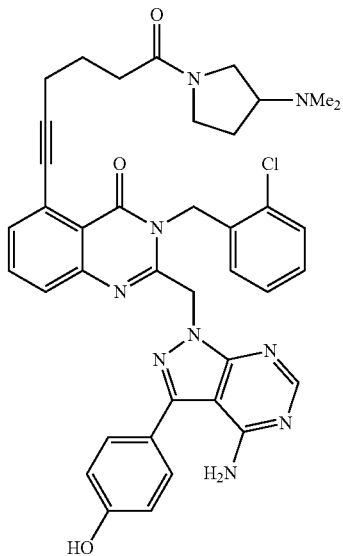 [SMILES: CN(C)C1CCN(C(=O)CCCC#Cc2cccc3nc(Cn4nc(-c5ccc(O)cc5)c5c(N)ncnc54)n(Cc4ccccc4Cl)c(=O)c23)C1] | 2-((4-Amino-3-(4-hydroxyphenyl)-1H-pyrazolo[3,4-d]pyrimidin-1-yl)methyl)-3-(2-chlorobenzyl)-5-(6-(3-(dimethylamino)pyrrolidin-1-yl)-6-oxohex-1-ynyl)quinazolin-4(3H)-one.<br>R$^t$ 1.41 min; m/z 716/718 (M + H)$^+$ (ES$^+$) (Method D);<br>$^1$H NMR (400 MHz, DMSO) δ: 1.72 (2H, quin), 2.11 (6H, d), 2.37-2.47 (4H, overlapping m), 2.86-2.96 (2H, overlapping m), 3.11-3.17 (2H, overlapping m), 3.41-3.58 (3H, overlapping m), 5.30 (2H, s), 5.71 (2H, s), 6.24 (1H, m), 6.82 (1H, m), 6.88 (2H, d), 7.04 (1H, m), 7.14 (1H, m), 7.33 (2H, d), 7.52 (2H, overlapping m), 7.78 (1H, m), 8.16 (1H, s), 9.69 (1H, s). |

TABLE 2-continued

| Example No. | Structure | Name and Analytical Data |
|---|---|---|
| 92 | 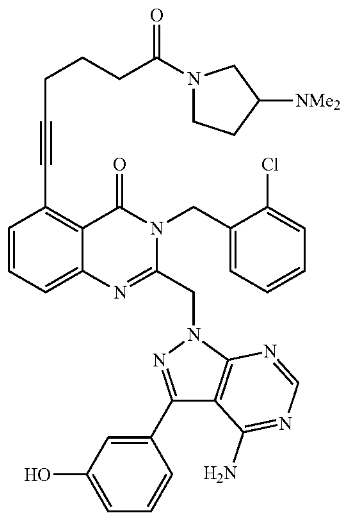 [SMILES: CN(C)C1CCN(C(=O)CCCC#Cc2cccc3nc(Cn4nc(-c5cccc(O)c5)c5c(N)ncnc54)n(Cc4ccccc4Cl)c(=O)c23)C1] | 2-((4-Amino-3-(3-hydroxyphenyl)-1H-pyrazolo[3,4-d]pyrimidin-1-yl)methyl)-3-(2-chlorobenzyl)-5-(6-(3-(dimethylamino)pyrrolidin-1-yl)-6-oxohex-1-ynyl)quinazolin-4(3H)-one.<br>R$^t$ 1.34 min; m/z 716/718 (M + H)$^+$ (ES$^+$) (Method D); $^1$H NMR (400 MHz, DMSO-d$_6$) δ: 1.55 (2H, br m), 1.72 (2H, m), 1.82 (1H, br m), 1.93 (1H, br m), 2.13 (6H, br s), 2.19 (1H, br s), 2.93 (2H, q), 3.15 (2H, m), 3.43 (1H, m), 3.55 (1H, m), 5.31 (2H, d), 5.75 (2H, s), 6.19 (1H, dd), 6.81 (1H, br t), 6.85 (1H, m), 6.92-6.95 (2H, overlapping m), 7.05 (1H, td), 7.13 (1H, dd), 7.31 (1H, t), 7.62 (1H, m), 7.67 (1H, m), 7.80 (1H, dt), 8.18 (1H, s), 9.66 (1H, br s). |
| 93 | 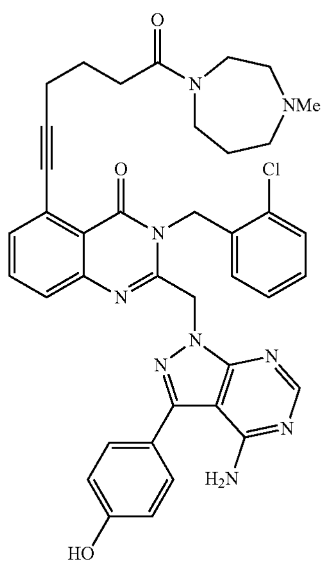 [SMILES: CN1CCCN(C(=O)CCCC#Cc2cccc3nc(Cn4nc(-c5ccc(O)cc5)c5c(N)ncnc54)n(Cc4ccccc4Cl)c(=O)c23)CC1] | 2-((4-Amino-3-(4-hydroxyphenyl)-1H-pyrazolo[3,4-d]pyrimidin-1-yl)methyl)-3-(2-chlorobenzyl)-5-(6-(4-methyl-1,4-diazepan-1-yl)-6-oxohex-1-ynyl)quinazolin-4(3H)-one.<br>R$^t$ 1.35 min; m/z 719/718 (M + H)$^+$ (ES$^+$) (Method D); $^1$H NMR (400 MHz, DMSO) δ: 1.66 (2H, br s), 1.80 (2H, quin), 2.21 (3H, s), 2.42-2.53 (8H, overlapping m), 3.41 (4H, br s), 5.41 (2H, s), 5.67 (2H, s), 6.26 (2H, br s), 6.47 (1H, d), 6.90-6.97 (3H, overlapping m), 7.11 (1H, m), 7.24 (1H, dd), 7.37 (2H, d), 7.55-7.57 (2H, overlapping m), 7.73 (1H, t), 8.17 (1H, s), 9.37 (1H, br s). |
| 94 | 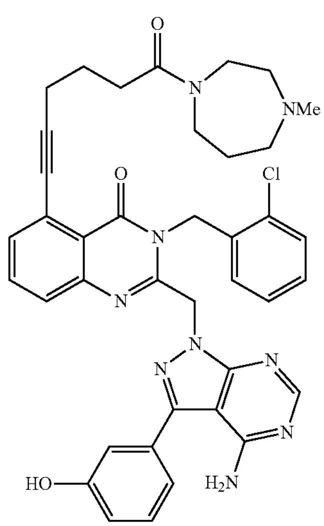 [SMILES: CN1CCCN(C(=O)CCCC#Cc2cccc3nc(Cn4nc(-c5cccc(O)c5)c5c(N)ncnc54)n(Cc4ccccc4Cl)c(=O)c23)CC1] | 2-((4-Amino-3-(3-hydroxyphenyl)-1H-pyrazolo[3,4-d]pyrimidin-1-yl)methyl)-3-(2-chlorobenzyl)-5-(6-(4-methyl-1,4-diazepan-1-yl)-6-oxohex-1-ynyl)quinazolin-4(3H)-one.<br>R$^t$ 1.36 min; m/z 716/718 (M + H)$^+$ (ES$^+$) (Method D); $^1$H NMR (400 MHz, DMSO-d$_6$) δ: 1.57 (1H, m), 1.61-1.73 (3H, overlapping m), 2.15 (3H, d), 2.27-2.45 (5H, overlapping m), 3.26 (2H, m), 3.37 (2H, m), 5.29 (2H, s), 5.75 (2H, s), 6.15 (1H, d), 6.79 (1H, dt), 6.83 (1H ddd), 6.92-6.93 (2H, overlapping m), 7.04 (1H, td), 7.12 (1H, dd), 7.30 (1H, t), 7.62 (1H, dd), 7.68 (1H, dd), 7.81 (1H, dd), 8.18 (1H, br s), 9.69 (1H, br s). |

TABLE 2-continued

| Example No. | Structure | Name and Analytical Data |
|---|---|---|
| 95 | (structure) | 2-((4-Amino-3-(4-hydroxy-3-methoxyphenyl)-1H-pyrazolo[3,4-d]pyrimidin-1-yl)methyl)-3-(2-chloro benzyl)-5-(6-morpholino-6-oxohex-1-ynyl)quinazolin-4(3H)-one. $R^t$ 1.78 min; m/z 719/721 $(M + H)^+$ $(ES^+)$ (Method D); $^1$H NMR (400 MHz, DMSO-$d_6$) δ: 1.71 (2H, quin), 2.46-2.55 (4H, overlapping m, partially obscured by DMSO signal), 3.23 (2H, m), 3.33 (4H, m, partially obscured by HOD signal), 3.45 (2H, m), 3.82 (3H, s), 5.30 (2H, s), 5.74 (2H, s), 6.18 (1H, dd), 6.81 (1H, td), 6.86-6.92 (2H, overlapping m), 6.97 (1H, d), 7.05 (1H, td), 7.14 (1H, dd), 7.61 (1H, dd), 7.68 (1H, dd), 7.81 (1H, dd), 8.17 (1H, br s), 9.35 (1H, br s) . . . |

Stereochemical Analysis of Compound Examples by Chiral, Stationary Phase HPLC

A common structural feature shared by many quinazolinone-based compounds that have been reported previously as potent PI3K inhibitors, is the presence of an aromatic nucleus bonded directly to N-3 of the bicyclic system (see for example WO 2001/081346 and WO 2008/127226). Depending upon the exact nature of the aryl substituent, this motif can give rise to sterically compressed bi-aryls, in which the rotational degree of freedom around the N-3 to C-aryl single bond is dramatically reduced. Compelling evidence has been obtained that in the case of compounds incorporating an ortho-substituted benzene ring, bond rotation can be so hindered as to give rise to discrete confomers. For example, chiral stationary phase HPLC analysis of PIK294 (Example 'S3' from WO 2008/127226) indicates that the compound exists as readily separable, non-superimposable stereoisomers, that is as a 1:1 mixture of enantiomeric atropisomers (FIG. 1).

This assignment was confirmed by the separation of a sample of PIK294, using chiral stationary phase preparative HPLC, into its discrete atropisomers (FIG. 2). As expected these enantiomeric compounds exhibited identical proton NMR spectra (data not shown) and, at both ambient and elevated temperatures, showed no detectable signs of interconversion over several days, indicating that the discrete rotational isomers have indefinitely long half lives under physiological conditions. The presence of stable atropisomers was also demonstrated for two additional N-3 aryl quinazolinones: the mercaptopurine derivative 20 (Example D-026 from WO 2001/081346) and a second pyrazolopyrimidine, analogue 21, revealing that this is a generic structural feature of this chemotype (FIG. 3).

In contrast, over twenty compounds, selected from the exemplified structures disclosed above (Examples 1, 9, 10, 11, 12, 13, 14, 15, 16, 17, 18, 19, 20, 21, 22, 23, 24, 25, 31, 32, 33, 34, and 38) were screened using chiral stationary phase HPLC (16 different conditions) and no evidence for atropisomerism was observed. The stereochemical implications of atropisomerism have been described recently as 'a lurking menace with the potential to significantly increase the cost of pharmaceutical research and development if ignored.' (Claydon, J. et al., Angew. Chem. Int. Ed., 2009, 48, 6398-6401).

The additional complexity and consequences for drug development resulting from atropisomerism are analogous to those arising from other sources of molecular isomerism such as the presence of a stereogenic centre. This property renders molecules such as 20 and 21 (FIG. 3) both chiral, and unless resolved, a racemic mixture; the components of which could possess different pharmacological and toxicological profiles. This feature is likely to significantly increase downstream development costs for such molecules, and the absence of atropisomerism in the compounds disclosed herein is therefore a highly desirable and advantageous property.

Enzyme Inhibition Assay

PI3 kinases catalyse the phosphorylation of phosphatidylinositol 4,5-biphosphate (PIP2) to phosphatidylinositol 3,4,5-triphosphate (PIP3) in the presence of ATP and $Mg^{2+}$ ions. The PIP3 product can be detected by displacement of biotin-PIP3 from energy transfer complexes consisting of europium labelled anti-GST monoclonal antibody, a GST-tagged Pleckstrin homology (PH) domain, biotinylated PIP3 and streptavidin-allophycocyanin (APC) by the time-resolved fluorescence resonance energy transfer (TR-FRET) (HTRF® PI3K enzyme assay, Millipore). Excitation (330 nm) of europium in the complex results in an energy transfer to the APC and a fluorescent emission at 665 nm although europium itself emits at its characteristic 620 nm. The PIP3 product formed by PI3K activity displaces biotin-PIP3 from the complex and results in a loss of energy transfer (decreasing signal).

The compound to be tested was added, at the desired final concentrations, to a mixture of PIP2 substrate and recombinant PI3 kinase α, δ or γ enzymes (Millipore), and the mixture incubated for 2 hr at RT. Following this incubation period, ATP (20 μM) was added to the enzyme/compound/PIP2 substrate mixture and the resulting mixture was incubated for 30 min at RT. A stopping solution containing biotinylated PIP3 and the detection mix containing the GST tagged GRP1 pleckstrin homology (PH) domain and fluorophores were then added and the mixture was incubated at RT for 15-18 hr, prior to detection in a fluorescence microplate reader (Varioskan® Flash, ThermoFisher Scientific).

The results were calculated according to the formula: APC signal (emission at 665 nm)/europium signal:(emission at 620 nm)×$10^4$. The percentage inhibition of each reaction was calculated relative to DMSO treated control, and the 50% inhibitory concentration ($IC_{50}$ value) then calculated from the concentration-response curve (Table 3 and Table 4).

PI3Kδ Cell Based Assay

As a means of assessing PI3K δ activation in response to stimuli, the phosphorylation status of the protein, Akt, a downstream product of $PI3K_\delta$, signaling was determined.

Human monocytic cells (U937 cells), were differentiated to macrophage-type cells by incubation with phorbol myristate acetate (PMA; 100 ng/mL) for 48 to 72 hr. Cells were then pre-incubated with either the test compound or vehicle for 2 hr and were then stimulated briefly by exposure to $H_2O_2$ (10 mM; 5-7 min) and the reaction stopped by replacing the media with 4% formaldehyde solution. Endogenous peroxide activity and formaldehyde were inactivated by incubating with quenching buffer (0.1% sodium azide, 1% $H_2O_2$ in PBS with 0.1% Triton X-100) for 20 min. The cells were washed with buffer (PBS containing 0.1% Triton X-100) and were incubated with blocking solution (1% BSA in PBS) for 1 hr and were then re-washed with buffer and incubated overnight with either anti-pAkt antibody or anti-pan-Akt antibody (both from Cell Signaling Technology). After washing with buffer (PBS containing 0.1% Triton X-100), cells were incubated with an HRP-conjugated secondary antibody (Dako) and the resultant signal was determined colorimetrically (OD: 450 nm with a reference wavelength of 655 nm) using TMB substrate (substrate reagent pack supplied by R&D Systems, Inc.).

This reaction was stopped by addition of 100 µL of 1N $H_2SO_4$ solution. Cells were then washed with buffer (PBS containing 0.1% Triton X-100) and 100 µL of 5% crystal violet solution was applied for 30 min. After washing with buffer (PBS containing 0.1% Triton X-100) 100 µL of 1% SDS was added to each well and the plates were shaken lightly for 1 hr prior to measuring the absorbance at 595 nm (Varioskan® Flash, Thermo-Fisher Scientific). The measured $OD_{450-655}$ readings were corrected for cell number by dividing the $OD_{450-655}$ by the $OD_{595}$ readings. The ratio of pAkt signal to total Akt signal was used to quantitate the extent of PI3K δ activation. The percentage inhibition for each well was calculated relative to a 10 µg/mL standard control (LY294002) set to 100% inhibition versus $H_2O_2$-only controls as 0% inhibition. The $IC_{50}$ values were calculated from the concentration-response curves generated by the serial dilutions of the test compounds (Table 3 and Table 4).

MTT Assay

PMA-differentiated U937 cells were pre-incubated with compound for 4 hr in 5% FCS or 10% FCS for 24 hr. The supernatant was replaced with 200 µL of new media and 10 µL of MTT stock solution (5 mg/ml) added to each well. After 1 hr incubation, the media were removed, 200 µL of DMSO added to each well and the plates were shaken lightly for 1 hr prior to reading the absorbance at 550 nm. The percentage loss of cell viability was calculated for each well relative to vehicle (0.5% DMSO)-treatment (Table 3).

TABLE 3

In Vitro Screening Data: Kinase Isozyme and Cellular Activity Ranges for Exemplified Compounds

| Test Cmpd Example | PI3 Kinase Inhibition $IC_{50}$ values at stated Isozyme [a] | | | Cellular Activity $IC_{50}$ values ($H_2O_2$ induced pAkt [b] | Cell Viability MTT Assay in D-U937 cells [c] | |
|---|---|---|---|---|---|---|
| | δ | γ | α | D-U937 Cells | at 4 hr | at 24 hr |
| 1 | ++ | + | + | ++ | − | − |
| 2 | ++ | + | − | ++ | − | − |
| 3 | ++ | ++ | ++ | ++ | − | − |
| 4 | ++ | ++ | ++ | ++ | − | − |
| 5 | ++ | ++ | ++ | ++ | − | − |
| 6 | ++ | + | + | ++ | − | − |
| 7 | ++ | + | + | ++ | − | − |
| 8 | ++ | + | + | ++ | − | − |
| 9 | ++ | + | + | ++ | − | − |
| 10 | ++ | + | + | ++ | − | − |
| 11 | ++ | + | + | ++ | − | − |
| 12 | ++ | + | + | ++ | + | − |
| 13 | ++ | + | + | ++ | − | − |
| 14 | ++ | + | + | ++ | − | − |
| 15 | ++ | + | − | ++ | − | − |
| 16 | ++ | + | + | ++ | − | − |
| 17 | ++ | − | + | ++ | − | − |
| 18 | ++ | + | + | ++ | − | − |
| 19 | ++ | + | + | ++ | − | − |
| 20 | ++ | + | + | ++ | − | − |
| 21 | ++ | + | + | ++ | − | − |
| 22 | ++ | + | + | ++ | − | − |
| 23 | ++ | + | + | ++ | − | − |
| 24 | ++ | + | + | ++ | − | − |
| 25 | ++ | + | + | ++ | − | − |
| 26 | ++ | + | + | ++ | − | − |
| 27 | ++ | + | + | ++ | − | − |
| 28 | ++ | + | + | ++ | − | − |
| 29 | ++ | + | + | ++ | − | − |
| 30 | ++ | + | + | ++ | − | − |
| 31 | ++ | + | + | ++ | − | − |
| 32 | ++ | + | + | ++ | − | − |
| 33 | ++ | + | + | ++ | − | − |
| 34 | ++ | + | + | ++ | − | − |
| 35 | ++ | + | + | ++ | − | − |
| 36 | ++ | − | + | ++ | − | − |
| 37 | ++ | − | + | ++ | − | − |
| 38 | ++ | + | + | ++ | − | − |
| 39 | ++ | + | ++ | ++ | − | − |
| 40 | ++ | + | + | ++ | − | − |
| 41 | ++ | + | + | ++ | − | − |
| 42 | ++ | + | + | ++ | − | − |
| 43 | ++ | + | + | ++ | − | − |
| 44 | ++ | + | − | ++ | − | − |
| 45 | ++ | + | + | ++ | − | − |
| 46 | ++ | + | + | ++ | − | − |
| 47 | ++ | + | + | ++ | − | − |
| 48 | ++ | + | + | ++ | − | − |
| 49 | ++ | + | + | ++ | − | − |
| 50 | ++ | + | + | ++ | − | − |
| 51 | ++ | + | + | ++ | − | − |
| 52 | ++ | ++ | + | ++ | − | − |
| 53 | ++ | ++ | ++ | ++ | − | − |
| 54 | ++ | ++ | ++ | ++ | − | − |
| 55 | ++ | ++ | + | ++ | − | − |
| 56 | ++ | ++ | ++ | ++ | − | − |
| 57 | ++ | ++ | + | ++ | − | − |
| 58 | ++ | ++ | + | ++ | − | − |
| 59 | ++ | ++ | + | ++ | − | − |
| 60 | ++ | ++ | + | ++ | − | − |
| 61 | ++ | ++ | + | ++ | − | − |
| 62 | ++ | ++ | + | ++ | − | − |
| 63 | ++ | ++ | + | ++ | − | − |
| 64 | ++ | ++ | + | ++ | − | − |
| 65 | ++ | ++ | + | ++ | − | − |
| 66 | ++ | ++ | + | ++ | − | + |
| 67 | ++ | ++ | + | ++ | − | − |
| 68 | ++ | ++ | + | ++ | − | − |
| 69 | ++ | ++ | + | ++ | + | − |
| 70 | ++ | ++ | + | ++ | − | − |
| 71 | ++ | ++ | + | ++ | − | − |

TABLE 3-continued

In Vitro Screening Data: Kinase Isozyme and Cellular Activity Ranges for Exemplified Compounds

| Test Cmpd Example | PI3 Kinase Inhibition IC$_{50}$ values at stated Isozyme [a] | | | Cellular Activity IC$_{50}$ values (H$_2$O$_2$ induced pAkt [b] | Cell Viability MTT Assay in D-U937 cells [c] | |
|---|---|---|---|---|---|---|
| | δ | γ | α | D-U937 Cells | at 4 hr | at 24 hr |
| 72 | ++ | ++ | + | ++ | − | − |
| 73 | ++ | ++ | + | ++ | − | − |
| 74 | ++ | ND | ND | ND | − | − |
| 75 | ++ | ++ | + | ++ | − | − |
| 76 | ++ | ++ | + | ++ | − | − |
| 77 | ++ | ++ | + | ++ | − | − |
| 78 | ++ | ++ | + | ++ | − | − |
| 79 | ++ | + | + | ++ | − | − |
| 80 | ++ | ND | ND | + | − | − |
| 81 | ++ | + | + | ++ | − | − |
| 82 | ++ | ++ | + | ++ | − | − |
| 83 | ++ | ND | ND | ++ | − | − |
| 84 | ++ | ND | ND | ++ | − | − |
| 85 | ++ | ND | ND | ++ | − | − |
| 86 | ++ | ++ | ++ | ++ | − | − |
| 87 | ++ | ND | ND | ++ | − | − |
| 88 | ++ | ++ | + | ++ | − | − |
| 89 | ++ | ++ | − | ++ | − | − |
| 90 | ++ | ++ | + | ++ | − | − |
| 91 | ++ | ++ | + | ++ | − | − |
| 92 | ++ | ND | ND | + | − | − |
| 93 | ++ | ++ | + | ++ | − | − |
| 94 | + | ND | ND | + | − | − |
| 95 | ++ | ++ | + | ++ | − | − |

[a] ++ IC$_{50}$ < 50 nM, + IC$_{50}$ < 1000 nM, − >1000 nM.
[b] ++ IC$_{50}$ < 10 nM; + IC$_{50}$ < 1000 nM;
[c] − <30%; + >30%.
ND: not done

TABLE 4

In Vitro Screening Data: Kinase Isozyme and Cellular Activity Values for Selected Exemplified Compounds

| Test Cmpd Example | PI3 Kinase Inhibition IC$_{50}$ values at stated Isozyme (nM) | | | Cellular Activity IC$_{50}$ values (H$_2$O$_2$ induced pAkt (nM) |
|---|---|---|---|---|
| | δ | γ | α | D-U937 Cells |
| 1 | 7 | 234 | 199 | 1.1 |
| 4 | 12 | 20 | 17 | 1.8 |
| 5 | 20 | 16 | 20 | 0.58 |
| 15 | 4 | 289 | 1966 | 0.57 |
| 37 | 12 | 1613 | 474 | 0.33 |
| 86 | 36 | 22 | 27 | 0.41 |
| 89 | 3 | 47 | 1486 | 0.2 | and stained using a DiffQuik stain system (Dade Behring). Cells were counted using oil immersion microscopy.

The results for the compound of Example 1 are shown in FIG. 4. The upper panel reveals the effect on BAL neutrophil numbers following the administration of Example 1 when the compound was dosed 2 hr before LPS challenge. The lower panel shows the results of a time course experiment on the inhibition of BAL neutrophilia by Example 1 when the compound is administered at different time points prior to endotoxin challenge. Data for neutrophil numbers is reported as total and differential number (test substance relative to vehicle) of cells per mL of BALF, mean±S.E.M. (n=8).

The profiles of two additional compounds: the carboxylic acid derivative, Example 4, and the mopholine amide, Example 5, were determined in this model of pulmonary inflammation. Treatment of the animals with the test compounds 2 hr before challenge with endotoxin, produced a comparable and dose dependent inhibition of the evoked inflammatory response as determined by the measurement of neutrophil influx into the lung (Table 5).

TABLE 5

The effect of escalating doses of compound Example 4 and Example 5 on the inhibition of LPS induced neutophilia in mouse lung

| Test Compound | % Inhibition of neutrophils in BAL at the dose indicated (mg/mL) | | |
|---|---|---|---|
| Example No. | (0.05) | (0.2) | (1.0) |
| 4 | 3.2 | 47.2 | 64.6 |
| 5 | 4.8 | 37.7 | 58.5 |

LPS-Induced Neutrophilia in the Mouse: Determination of Effect and Duration of Action Non-fasted mice were dosed by the intra-tracheal route with either vehicle, or the test substance at the time points ("pre-dose") indicated with respect to the start of LPS treatment. At T=0, mice were placed into an exposure chamber and exposed to LPS. Eight hr after LPS challenge, animals were anesthetized, the trachea cannulated and BALF extracted by infusing and withdrawing 1 mL of PBS into the lungs via a tracheal catheter. Total and differential white cell counts in the BALF samples were measured using a Neubaur haemocytometer. Cytospin smears of the BALF samples were prepared by centrifugation at 200 rpm for 5 min at RT However, by increasing the period between drug treatment and the subsequent LPS challenge from 2 to 8 hr it was possible to distinguish a difference in the duration of action of the two compounds when administered at the same dose. Under these test conditions the level of anti-inflammatory activity of compound Example 5 was still over half of its original value, as determined 2 hr after drug treatment, at the 8 hr time point. (Table 6). In contrast, under the same conditions, the remaining anti-inflammatory effect of compound Example 4 was reduced by 90%, to an insignificant level (<5% inhibition), demonstrating that its pharmacological activity is much less sustained.

TABLE 6

Comparison the activities of compounds Example 4 and Example 5 to inhibit an evoked (LPS) inflammatory response in mouse lung 2 and 8 hr after administration

| Test Compound Example No. | % Inhibition at 0.2 mg/mL dose at time indicated (hr) | | % Reduction of inhibition at 8 hr compared with 2 hr |
|---|---|---|---|
| | (2) | (8) | |
| 4 | 47.2 | 12.9 | 73 |
| 5 | 37.7 | 21.2 | 44 |

Cigarette Smoke Model

A/J mice (males, 5 weeks old) were exposed to cigarette smoke (4% cigarette smoke, diluted with compressed air) for 30 min/day for 11 days using a Tobacco Smoke Inhalation Experiment System for small animals (Model SIS-CS; Sibata Scientific Technology, Tokyo, Japan). Test substances were given intra-nasally (35 μL of solution in 50% DMSO/PBS) and therapeutically twice daily for 3 days after the final cigarette smoke exposure. Twelve hr after the last dosing, animals were anesthetized, the trachea cannulated and bronchoalveolar lavage fluid (BALF) was collected. The numbers of alveolar macrophages and neutrophils were determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

The results for the compound of Example 1 are shown in FIG. 5 for neutrophils (upper panel) and for activated alveolar macrophages (lower panel). The cigarette smoke model used for this study is reported to be a corticosteroid refractory system, [To, Y. et al., *Am. J. Respir. Crit. Care Med.*, 2010, 182:897-904; Medicherla, S. et al., *J. Pharmacol. Exp. Ther.* 2008, 324:921-9] and the data reveal that dexamethasone (0.3-10 mg/kg, p.o.) was inactive. The results obtained for Example 1 demonstrate that the compound possesses anti-inflammatory activity when administered as a monotherapy. Moreover, when Example 1 was co-administered with fluticasone propionate, at a dose which lacks effect as monotherapy, a marked enhancement of anti-inflammatory activity was detected. Data for cell numbers are shown as the mean±SEM.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

The invention claimed is:

1. A method for treating asthma in a subject in need thereof comprising administering an effective amount of the compound

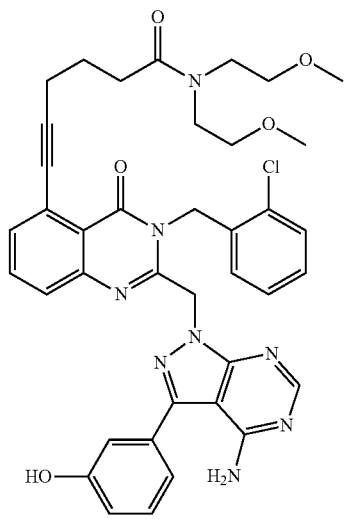 [SMILES: COCCN(CCOC)C(=O)CCCC#Cc1cccc2nc(Cn3nc(-c4cccc(O)c4)c4c(N)ncnc43)n(Cc3ccccc3Cl)c(=O)c12]

or a pharmaceutically acceptable salt thereof, including all stereoisomers, tautomers and isotopic derivatives thereof.

* * * * *